US012643895B2

(12) United States Patent
Pfaffenrot et al.

(10) Patent No.: US 12,643,895 B2
(45) **Date of Patent: *Jun. 2, 2026**

(54) HETEROARYL-SUBSTITUTED PYRAZOLO-PYRIDINE PROTEIN KINASE INHIBITORS FOR PROMOTING LIVER REGENERATION OR REDUCING OR PREVENTING HEPATOCYTE DEATH

(71) Applicant: HepaRegeniX GmbH, Tübingen (DE)

(72) Inventors: Bent Pfaffenrot, Tübingen (DE); Roland Selig, Ismaning (DE); Stefan Laufer, Tübingen (DE); Wolfgang Albrecht, Ulm (DE)

(73) Assignee: HEPAREGENIX GMBH, Tübingen (DE)

( * ) Notice: Subject to any disclaimer, the term of this patent is extended or adjusted under 35 U.S.C. 154(b) by 1128 days.

This patent is subject to a terminal disclaimer.

(21) Appl. No.: 17/630,105

(22) PCT Filed: Jul. 27, 2020

(86) PCT No.: PCT/EP2020/071090

§ 371 (c)(1),
(2) Date: Jan. 25, 2022

(87) PCT Pub. No.: WO2021/018820

PCT Pub. Date: Feb. 4, 2021

(65) Prior Publication Data

US 2022/0340561 A1 Oct. 27, 2022

(30) Foreign Application Priority Data

Jul. 29, 2019 (EP) .................................... 19188876
Apr. 30, 2020 (EP) .................................... 20172253

(51) Int. Cl.
*C07D 471/04* (2006.01)

(52) U.S. Cl.
CPC .................................. *C07D 471/04* (2013.01)

(58) Field of Classification Search
CPC .................................................... C07D 471/04
See application file for complete search history.

(56) References Cited

U.S. PATENT DOCUMENTS

| | | | |
|---|---|---|---|
| 6,514,981 | B1 | 2/2003 | Tang et al. |
| 11,040,027 | B2 | 6/2021 | Albrecht et al. |
| 11,731,968 | B2 | 8/2023 | Juchum et al. |
| 11,858,927 | B2 | 1/2024 | Praefke et al. |
| 11,912,701 | B2 | 2/2024 | Albrecht et al. |
| 12,466,826 | B2 | 11/2025 | Selig et al. |
| 2020/0399241 | A1 | 12/2020 | Scheidt et al. |
| 2021/0078995 | A1 | 3/2021 | Praefke et al. |
| 2021/0261545 | A1 | 8/2021 | Juchum et al. |
| 2022/0281864 | A1 | 9/2022 | Albrecht et al. |
| 2023/0088395 | A1 | 3/2023 | Selig et al. |

FOREIGN PATENT DOCUMENTS

| | | | |
|---|---|---|---|
| CA | 3075477 | A1 | 2/2019 |
| CN | 112778311 | A | 5/2021 |
| CN | 113072497 | A | 7/2021 |
| EP | 2161271 | A1 | 3/2010 |
| EP | 2508607 | A1 | 10/2012 |
| FR | 2876377 | A1 | 4/2006 |
| JP | 2006282745 | A | 10/2006 |
| RU | 2678455 | C1 | 1/2019 |
| WO | 2003035621 | A1 | 5/2003 |
| WO | 2003037898 | A1 | 5/2003 |
| WO | 2004058764 | A1 | 7/2004 |
| WO | 2007002325 | A1 | 1/2007 |
| WO | 2007002433 | A1 | 1/2007 |
| WO | 2007013896 | A2 | 2/2007 |
| WO | 2008063888 | A2 | 5/2008 |
| WO | 2008064255 | A2 | 5/2008 |
| WO | 2008064265 | A2 | 5/2008 |
| WO | 2008079903 | A1 | 7/2008 |
| WO | 2008079906 | A1 | 7/2008 |
| WO | 2010104945 | A1 | 9/2010 |
| WO | 2010111527 | A1 | 9/2010 |
| WO | 2010129567 | A1 | 11/2010 |
| WO | 2010129570 | A1 | 11/2010 |
| WO | 2011047432 | A1 | 4/2011 |
| WO | 2011079133 | A2 | 6/2011 |
| WO | 2012109075 | A1 | 8/2012 |
| WO | 2012129562 | A2 | 9/2012 |
| WO | 2012135631 | A1 | 10/2012 |

(Continued)

OTHER PUBLICATIONS

Leonov et al, machine translation of RU 2678455, pub. Jan. 29, 2019, p. 1-17. (Year: 2019).*
Patani et al, Bioisosterism: A Rational Approach in Drug Design, 1996, Chem. Rev. 96, 8, 3147-3176. (Year: 1996).*
Brahim, P. , "Case History: Vemurafenib, a Potent, Selective, and First-in-Class Inhibitor of Mutant BRAF for the Treatment of Metastatic Melanoma", Annual Reports in Medicinal Chemistry 48(26), 435-449 (2013).
Wermuth, C. , et al., "Molecular Variation Based on Isosteric Replacements", The Practice of Medicinal Chemistry 13, 203-237 (1996).
U.S. Appl. No. 16/965,912, 2021-0078995.
U.S. Appl. No. 17/254,071, 2021-0261545.
U.S. Appl. No. 17/260,519, 2022-0281864.
U.S. Appl. No. 16/478,006, U.S. Pat. No. 11,040,027.
U.S. Appl. No. 17/792,685.

(Continued)

*Primary Examiner* — Adam C Milligan
*Assistant Examiner* — Karen Cheng
(74) *Attorney, Agent, or Firm* — Viksnins Harris Padys Malen LLP

(57) ABSTRACT

The invention relates to pyrazolo-pyridine compounds which inhibit mitogen-activated protein kinase kinase 4 (MKK4) and in particular, selectively inhibit MKK4 over protein kinases JNK1 and MKK7. The compounds are useful for promoting liver regeneration or reducing or preventing hepatocyte death. They are further useful for treating osteoarthritis or rheumatoid arthritis, or CNS-related diseases.

22 Claims, No Drawings

(56) References Cited

FOREIGN PATENT DOCUMENTS

| | | | |
|---|---|---|---|
| WO | 2012136859 | A1 | 10/2012 |
| WO | 2013032951 | A1 | 3/2013 |
| WO | 2014035846 | A2 | 3/2014 |
| WO | 2014047648 | A1 | 3/2014 |
| WO | 2014194127 | A1 | 12/2014 |
| WO | 2017066193 | A1 | 4/2017 |
| WO | 2018134254 | A1 | 7/2018 |
| WO | 2019031990 | A1 | 2/2019 |
| WO | 2019149738 | A1 | 8/2019 |
| WO | 2019243315 | A1 | 12/2019 |
| WO | 2020016243 | A1 | 1/2020 |
| WO | 2020051207 | A2 | 3/2020 |
| WO | 2020123675 | A1 | 6/2020 |
| WO | 2021144287 | A1 | 7/2021 |

OTHER PUBLICATIONS

Asaoka, Y , "Diverse physiological functions of JNK signaling networks during early embryogenesis", Comparative Physiology and Biochemistry 30 (2), 59-67 (2013). [English Abstract].

Chem Abstract , Registry No. 1246614-25-4, 1 page (Oct. 20, 2010).

Deibler, K , et al., "A Chemical Probe Strategy for Interrogating Inhibitor Selectivity Across the MEK Kinase Family", ACS Chem Biol 12, 1245-1256, Supporting Information, 82 pages (2017).

Deibler, K , et al., "Synthesis and Biological Evaluation of 3-Arylindazoles as Selective MEK4 Inhibitors", ChemMedChem 14, 615-620 (2019).

Erion, M , et al., "Liver-Targeted Drug Delivery Using HepDirect1 Prodrugs", Journal of Pharmacology and Experimental Therapeutics 312(2), 554-560 (2005).

Grueninger, F , et al., "Novel screening cascade identifies MKK4 as key kinase regulating Tau phosphorylation at Ser422", Mol Cell Biochem 357, 199-207 (2011).

Hu, G , et al., "MicroRNA-145 attenuates TNF-α-driven cartilage matrix degradation in osteoarthritis via direct suppression of MKK4", Cell Death and Disease 8, e3140, 13 pages (2017).

Kim, D , et al., "Novel Small Molecule Raf Kinase Inhibitors for Targeted Cancer Therapeutics", Arch Pharm Res 35(4), 605-612 (2012).

Krishna, S , et al., "A Fluorescence-Based Thermal Shift Assay Identifies Inhibitors of Mitogen Activated Protein Kinase Kinase 4", PLoS One 8(12), e81504, 11 pages (2013).

Merriam-Webster , "Prevent", https:/www.merriam-webster.com/dictionary/prevent, 2022.

Ogura, M , et al., "Prenylated quinolinecarboxylic acid derivative prevents neuronal cell death through inhibition of MKK4", Biochemical Pharmacology 1-37, doi: https://doi.org/10.1016/j.bcp.2018.10.008 (2018).

Patent Cooperation Treaty , Search Report and Written Opinion for PCT/EP2020/071090, 12 pages, dated Oct. 9, 2020.

Schneider, C , et al., "Synthesis of 6-Substituted Pyrido[2,3-b]indoles by Electrophilic Substitution", Synlett 14, 2237-2241 (2007).

Vin, H , et al., "BRAF inhibitors suppress apoptosis through off-target inhibition of JNK signaling", eLife 2, e00969, DOI: 10.755/4/eLife.00969, 1-25 (2013).

Vin, H , et al., "BRAF inhibitors suppress apoptosis through off-target inhibition of JNK signaling", eLife 2, e00969, DOI: 10.7554/eLife.00969, 1-25, Supporting Information—Figures and Supplements (2013).

Wadsworth, A , et al., "A review of the synthesis of a-carbolines", European Journal of Medicinal Chemistry 97, 816-829 (2015).

Willenbring, H. , et al., "A Therapy for Liver Failure Found in the JNK Yard", Cell 153, 283-284 (2013).

Wuestefeld, T , et al., "A Direct in Vivo RNAi Screen Identifies MKK4 as a Key Regulator of Liver Regeneration", Cell 153, 389-401 (2013).

U.S. Appl. No. 17/792,685, 2023-0088395.

Pubchem , "Vemurafenib", CID No. 42611257, 54 pages (Create date: Jun. 22, 2009).

* cited by examiner

HETEROARYL-SUBSTITUTED PYRAZOLO-PYRIDINE PROTEIN KINASE INHIBITORS FOR PROMOTING LIVER REGENERATION OR REDUCING OR PREVENTING HEPATOCYTE DEATH

CROSS-REFERENCE TO RELATED APPLICATIONS

This application claims the benefit of priority of EP Application Serial No. 19188876.7, filed Jul. 29, 2019 and EP Application Serial No. 20172253.5 filed Apr. 30, 2020.

The present invention relates to heteroaryl-substituted pyrazolo-pyridine protein kinase inhibitors which inhibit mitogen-activated protein kinase kinase 4 (MKK4) and in particular, selectively inhibit MKK4 over protein kinases JNK1 and MKK7.

BACKGROUND OF THE INVENTION

Liver diseases may be caused by infection, injury, exposure to toxic compounds, like alcohol or drugs, autoimmune processes, genetic defects, and other factors. Liver has a remarkable regenerative capacity which, however, may be impaired in disease state and may therefore be insufficient to compensate for the loss of hepatocytes and organ function.

WO 2007/002433 describes compounds which are protein kinase inhibitors useful to treat diseases and conditions associated with aberrant activity of protein kinases. These compounds are inhibitors of Raf protein kinase, in particular B-Raf and c-Raf and mutations thereof and are therefore useful for cancer treatment. Further, they are said to inhibit a large variety of other protein kinases, among them c-Jun N-terminal kinases (JNK) and in particular JNK1. WO 2007/002325 has a similar disclosure and WO 2012/109075 and WO 2014/194127 disclose modified compounds having Raf protein kinase inhibiting activity. H. Vin et al. refer to two compounds of WO 2007/002433 as B-Raf inhibitors that suppress apoptosis through off-target inhibition of JNK signaling. WO 2010/111527 describes pyrazolo[3,4-b]pyridine compounds which are protein kinase inhibitors useful to treat a Raf protein kinase mediated disease or condition, like cancer. Further, they are said to inhibit a large variety of other protein kinases, among them c-Jun N-terminal kinases (JNK) and in particular JNK1. WO 2012/136859 discloses some compounds which are described as inhibitors of mitogen-activated protein kinase 4 (MKK4) and as being useful in the treatment of liver failure, for the protection of hepatocytes against apoptosis and for the regeneration of hepatocytes. Wuestefeld et al. (Cell 153:389-401, 2013) and Willebring et al. (Cell 153:283-284) describe a functional genetic approach for the identification of gene targets that can be exploited to increase the regenerative capacity of hepatocytes. In particular, Wuestefeld et al. identify protein kinase MKK4 as a key regulator of liver regeneration and report that MKK4 suppression increased hepatocyte regeneration via compensatory upregulation of MKK7 and a JNK1-dependent activation of ATF2 and ELK1.

On the basis of the findings of the prior art it has been concluded that MKK4 and JNK1 inhibitors could be useful to treat JNK1-mediated diseases. However, despite the recognition that inhibition of JNK1 could be beneficial for treatment of liver diseases, no clinical studies have been performed. WO 2018/134254 discloses pyrrolo-pyridine compounds that are protein kinase inhibitors for promoting liver regeneration or reducing or preventing hepatocyte death.

SUMMARY OF THE INVENTION

The problem underlying the invention was to provide compounds that are useful MKK4 inhibitors, in particular MKK4 inhibitors which selectively inhibit MKK4 over MKK7 and JNK1. A further problem was to provide compounds that are MKK4 inhibitors which selectively inhibit MKK4 over MKK7 and JNK1, which are useful for treating liver diseases and especially for promoting liver regeneration or reducing or preventing hepatocyte death.

This problem was solved by providing the compounds of formula (I).

Thus, the invention relates to the following embodiments:

1. A compound having formula (I)

(I)

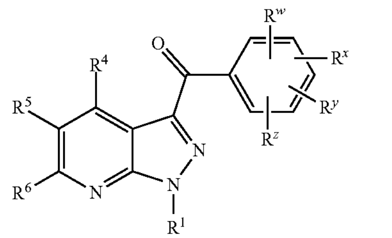

and the pharmaceutically acceptable salts, prodrugs, biologically active metabolites, solvates and stereoisomers thereof, wherein the variables in formula (I) have the meanings as follows:

$R^1$ is H or alkyl $R^4$ is H or alkyl;

$R^5$ is selected from a) pyrimidinyl which is substituted with 1 or 2 substituents independently selected from cycloalkyl, alkyl, —$COOR^{10}$, —OH, alkylsulfanyl, alkylsulfinyl, alkylsulfonyl, tetrazolyl, CN, halogen, alkoxy, —($NR^{10}$=)S(=O)-alkyl [S-alkylsulfonimidoyl], and

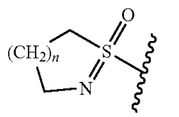

and b1) pyridyl which is substituted with 1 or 2 substituents independently selected from alkyl and halogen and which is optionally further substituted with a group selected from —OH, alkoxy, CN, —$COOR^{10}$, $CF_3$, —($NR^{10}$=)S(=O)-alkyl and

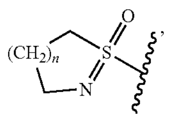

and b2) pyridyl substituted with —$COOR^{10}$ and further substituted with —OH, CN, or $CF_3$;

$R^6$ is H or alkyl;

$R^w$ is —$NR^{10}SO_2R^{12}$;

$R^x$ is H, halogen or alkyl;

$R^y$ is H, halogen or alkyl;

$R^z$ is H, halogen or alkyl;

wherein one or two or three of $R^x$, $R^y$ or $R^z$ are halogen, and the other(s) of $R^x$, $R^y$ and $R^z$ is H or alkyl;

$R^{10}$ at each occurrence is independently H or alkyl;

$R^{12}$ is H, alkyl or phenylalkyl; and n is 1 or 2.

2. The compound and the pharmaceutically acceptable salts, prodrugs, solvates and optical isomers thereof, of embodiment 1, wherein $R^1$ is H.

3. The compound and the pharmaceutically acceptable salts, prodrugs, solvates and optical isomers thereof, of embodiment 1 or 2, wherein 2 or 3 of $R^x$, $R^y$ or $R^z$ are halogen.

4. The compound and the pharmaceutically acceptable salts, prodrugs, solvates and optical isomers thereof, of any one of embodiments 1 to 3, wherein the halogen atom or halogen atoms of $R^x$, $R^y$ or $R^z$ are independently F or Cl, in particular F.

5. The compound and the pharmaceutically acceptable salts, prodrugs, solvates and optical isomers thereof, of any one of the preceding embodiments, wherein $R^4$ and $R^6$ are H.

6. The compound and the pharmaceutically acceptable salts, prodrugs, solvates and optical isomers thereof, of embodiment 6, wherein $R^5$ is pyrimidinyl substituted with 1 or 2 substituents independently selected from cycloalkyl, alkyl, —$COOR^{10}$, alkoxy, OH, alkylsulfanyl, alkylsulfinyl, alkylsulfonyl, halogen, CN, and tetrazolyl.

7. The compound and the pharmaceutically acceptable salts, prodrugs, solvates and optical isomers thereof, of embodiment 6, wherein $R^5$ is pyrimidinyl substituted with 1 or 2 substituents independently selected from cycloalkyl, alkyl, alkoxy, OH, alkylsulfanyl, alkylsulfinyl, alkylsulfonyl, halogen, CN, and tetrazolyl.

8. The compound and the pharmaceutically acceptable salts, prodrugs, solvates and optical isomers thereof, of embodiment 7, wherein $R^5$ is pyrimidinyl substituted with 1 or 2 substituents independently selected from cycloalkyl, alkoxy, OH, alkylsulfanyl, alkylsulfinyl, alkylsulfonyl, halogen, CN, and tetrazolyl.

9. The compound and the pharmaceutically acceptable salts, prodrugs, solvates and optical isomers thereof, of embodiment 8, wherein $R^5$ is pyrimidinyl substituted with 1 or 2 substituents independently selected from cycloalkyl, alkoxy, OH, alkylsulfanyl, halogen, CN, and tetrazolyl.

10. The compound and the pharmaceutically acceptable salts, prodrugs, solvates and optical isomers thereof, of embodiment 9, wherein $R^5$ is pyrimidinyl substituted with 1 or 2 substituents independently selected from cycloalkyl, alkoxy, —OH, halogen and alkylsulfanyl.

11. The compound and the pharmaceutically acceptable salts, prodrugs, solvates and optical isomers thereof, of any one of embodiments 1 to 5, wherein $R^5$ is pyrimidinyl substituted with a group selected from cycloalkyl, alkyl, —$COOR^{10}$, alkoxy, OH, alkylsulfanyl, alkylsulfinyl and alkylsulfonyl, and further substituted with a group selected from halogen, CN, tetrazolyl, —($NR^{10}$═)S(═O)-alkyl and

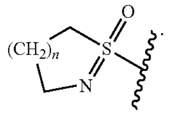

12. The compound and the pharmaceutically acceptable salts, prodrugs, solvates and optical isomers thereof, of embodiment 7, wherein $R^5$ is pyrimidinyl substituted with a group selected from cycloalkyl, alkyl, alkoxy, —OH and alkylsulfanyl and further substituted with a group selected from alkyl, alkoxy, and alkylsulfanyl.

13. The compound and the pharmaceutically acceptable salts, prodrugs, solvates and optical isomers thereof, of embodiment 12, wherein $R^5$ is pyrimidinyl substituted with a group selected from cycloalkyl, alkoxy, —OH and alkylsulfanyl and further substituted with a group selected from alkyl, alkoxy, and alkylsulfanyl.

14. The compound and the pharmaceutically acceptable salts, prodrugs, solvates and optical isomers thereof, of any one of embodiments 1 to 5, wherein $R^5$ is pyrimidinyl which is substituted with a cycloalkyl group and which is optionally further substituted with a group selected from cycloalkyl, alkyl, —$COOR^{10}$, —OH, alkylsulfanyl, alkylsulfinyl, alkylsulfonyl, tetrazolyl, CN, halogen, alkoxy, —($NR^{10}$═)S(═O)-alkyl [S-alkylsulfonimidoyl], and

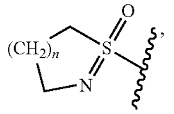

15. The compound and the pharmaceutically acceptable salts, prodrugs, solvates and optical isomers thereof, of embodiment 14, wherein $R^5$ is pyrimidinyl which is substituted with a cycloalkyl group and which is optionally further substituted with a group selected from cycloalkyl, alkyl, —$COOR^{10}$, —OH, alkylsulfanyl, alkylsulfinyl, alkylsulfonyl, tetrazolyl, CN, halogen, and alkoxy.

16. The compound and the pharmaceutically acceptable salts, prodrugs, solvates and optical isomers thereof, of embodiment 15, wherein $R^5$ is pyrimidinyl which is substituted with a cycloalkyl group and which is optionally further substituted with a group selected from cycloalkyl, alkyl, —$COOR^{10}$, —OH, alkylsulfanyl, tetrazolyl, CN, halogen, and alkoxy.

17. The compound and the pharmaceutically acceptable salts, prodrugs, solvates and optical isomers thereof, of embodiment 16, wherein $R^5$ is pyrimidinyl which is substituted with a cycloalkyl group and which is optionally further substituted with a group selected from alkyl, —$COOR^{10}$, —OH, alkylsulfanyl, CN, halogen, and alkoxy.

18. The compound and the pharmaceutically acceptable salts, prodrugs, solvates and optical isomers thereof, of any one of the preceding embodiments, wherein $R^5$ is pyrimidinyl substituted in 2-position.

19. The compound and the pharmaceutically acceptable salts, prodrugs, solvates and optical isomers thereof, of any one of embodiments 1 to 5, wherein $R^5$ is pyrid-3-yl (the pyridyl group is bonded in 3-position to the pyrazolopyridine group) substituted with —$COOR^{10}$ in 2-position and further substituted with —OH, CN or $CF_3$.

20. The compound and the pharmaceutically acceptable salts, prodrugs, solvates and optical isomers thereof, of any one of embodiments 1 to 5, wherein $R^5$ is pyridyl-4-yl (the pyridyl group is bonded in 4-position to the pyrazolopyridine group) substituted with alkyl or halogen in 3-position.

21. The compound and the pharmaceutically acceptable salts, prodrugs, solvates and optical isomers thereof, of any one of the preceding embodiments, wherein $R^{10}$ is H or alkyl, in particular H.

22. The compound and the pharmaceutically acceptable salts, prodrugs, solvates and optical isomers thereof, of any one of the preceding embodiments, wherein $R^{12}$ is alkyl or phenylalkyl.

23. The compound and the pharmaceutically acceptable salts, prodrugs, solvates and optical isomers thereof, of embodiment 22, wherein $R^{12}$ is $C_1$-$C_3$-alkyl or benzyl.

24. The compound and the pharmaceutically acceptable salts, prodrugs, solvates and optical isomers thereof, of any one of the preceding embodiments having formula (Ia)

(Ia)

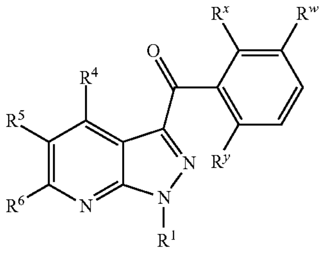

wherein $R^x$ is halogen;

$R^y$ is halogen; and $R^1$, $R^4$, $R^5$, $R^6$, and $R^w$ are as defined any one of the preceding embodiments.

25. The compound and the pharmaceutically acceptable salts, prodrugs, solvates and optical isomers thereof, of any one of embodiments 1 to 23 having formula (Ib)

(Ib)

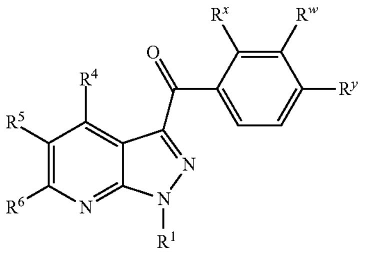

wherein $R^x$ is halogen;

$R^y$ is halogen; and $R^1$, $R^4$, $R^5$, $R^6$, and $R^w$ are as defined any one of embodiments 1 to 15.

26. The compound and the pharmaceutically acceptable salts, prodrugs, solvates and optical isomers thereof, of any one of embodiments 1 to 23 having formula (Ic)

(Ic)

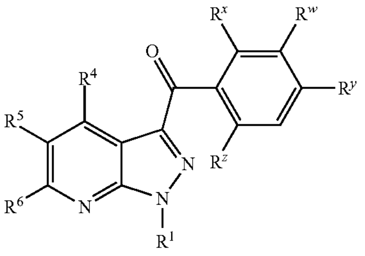

wherein $R^x$ is halogen;

$R^y$ is halogen;

$R^z$ is halogen; and $R^1$, $R^4$, $R^5$, $R^6$, and $R^w$ are as defined any one of embodiments 1 to 15.

27. The compound and the pharmaceutically acceptable salts, prodrugs, solvates and optical isomers thereof, of any one of embodiments 24 to 26, wherein $R^x$, $R^y$ and $R^z$ (if present) are F or Cl, in particular F.

DETAILED DESCRIPTION OF THE INVENTION

In an embodiment, the invention relates to a compound of the formula I and the pharmaceutically acceptable salts, prodrugs, esters, solvates and optical isomers thereof, wherein $R^1$, $R^4$ to $R^6$, $R^w$, $R^x$, $R^y$ and $R^z$ are as defined above in any combination.

In a further embodiment, the invention relates to a compound of formula (Ia), (Ib), and (Ic) and the pharmaceutically acceptable salts, prodrugs, esters, solvates and optical isomers thereof, wherein the variables are as defined in the embodiments above.

In a further embodiment, at least two of $R^x$, $R^y$ or $R^z$ are halogen, and the other of $R^x$, $R^y$ and $R^z$ is H, halogen or alkyl, in particular alkyl or halogen. Halogen is preferably F or Cl and in particular F.

In a further embodiment, $R^1$, $R^4$ and $R^6$ are H.

In a further embodiment, $R^{12}$ is methyl, ethyl or propyl.

In an embodiment, the invention relates to MKK4 inhibitors of formula (I) and (Ia) to (Ic) and the pharmaceutically acceptable salts, prodrugs, solvates and optical isomers thereof, and in particular to MKK4 inhibitors which selectively inhibit protein kinase MKK4 over protein kinases JNK1 and MKK7.

Further, the invention also relates to the compounds of the invention for use in inhibiting protein kinase MKK4 and in particular for use in selectively inhibiting protein kinase MKK4 over protein kinases JNK1 and MKK7.

Further, the invention also relates to said compounds for use in promoting liver regeneration or reducing or preventing hepatocyte death and, at the same time, increasing hepatocyte proliferation.

The invention also includes the pharmaceutically acceptable salts of the compounds mentioned above. The pharmaceutically acceptable salts are especially acid or base addition salts with pharmaceutically acceptable acids or bases. Examples of suitable pharmaceutically acceptable organic and inorganic acids are hydrochloric acid, hydrobromic acid, phosphoric acid, sulfuric acid, sulfamic acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966. Examples of suitable pharmaceutically acceptable organic and inorganic bases are alkali metal hydroxides, such as sodium hydroxide or potassium hydroxide, alkaline earth metal hydroxides such as calcium or magnesium hydroxide, ammonium hydroxide, organic nitrogen bases such as dimethylamine, trimethylamine, ethanolamine, diethanolamine, triethanolamine, choline, 2-amino-2-hydroxymethyl-propane-1,3-diol, meglumine, procaine etc. L-arginine, L-lysine, ethylenediamine, or hydroxyethylpyrrolidine.

The invention also includes any tautomeric, crystal and polymorphic form of the compounds and salts of the present invention and mixtures thereof.

The invention also includes solvates such as hydrates.

The compounds of the invention may contain one or more chiral centers, and exist in different optically active forms such enantiomers and diastereomers.

As used herein, the term "pro-drug" refers to an agent which is converted into the parent drug in vivo by some physiological chemical process. An example, without limitation, of a pro-drug would be a compound of the present invention in the form of an ester.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue. Exemplary pro-drugs include, but are not limited to, compounds with carboxylic acid substituents wherein the free hydrogen is replaced by ($C_1$-$C_4$)alkyl, ($C_1$-$C_{12}$)alkanoyloxy-methyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyl-oxy)ethyl having from 4 to 7 carbon atoms, 1-methyl-1-(alkoxycarbonyloxy)-ethyl having from 5 to 8 carbon atoms, N-(alkoxycarbonyl) aminomethyl having from 3 to 9 carbon atoms, 1-(N-(alkoxycarbonyl)amino)ethyl having from 4 to 10 carbon atoms, 3-phthalidyl, 4-crotono-lactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)-alkylcarbamoyl-($C_1$-$C_2$)alkyl and piperidino-, pyrrolidino- or morpholino($C_2$-$C_3$)alkyl. Other exemplary pro-drugs release an alcohol of Formula (I) wherein the free hydrogen of the hydroxyl substituent (e.g., R group contains hydroxyl) is replaced by ($C_1$-$C_6$)alkanoyloxy-methyl, 1-(($C_1$-$C_6$)alkanoyloxy)-ethyl, 1-methyl-1-(($C_1$-$C_6$)alkanoyloxy)ethyl, ($C_1$-$C_{12}$)alkoxy-carbonyloxy-methyl, N—($C_1$-$C_6$)-alkoxy-carbonylaminomethyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1$-$C_5)alkyl)_2$ or glycosyl (the radical resulting from detachment of the hydroxyl of the hemiacetal of a carbohydrate).

The expression MKK4 inhibitor means that the kinase activity of MKK4 is inhibited with an $IC_{50}$ of <10 μmol/l, preferably <1 μmol/l, and in particular <0.5 μmol/l. The expression "selectively inhibit protein kinase MKK4 over protein kinases JNK1 and MKK7" as used herein means that the ratio of MKK7 inhibiting activity to MKK4 inhibiting activity or the ratio of JNK1 inhibiting activity to MKK4 inhibiting activity, expressed as either percent of control or Kd, is ≥10, as measured with KINOMEscan™.

The expression "promoting liver regeneration or reducing or preventing hepatocyte death" as used herein means an increase in the relative number of proliferating hepatocytes by at least 30%, preferably at least 50%, as compared to the number of proliferating cells at the beginning of therapy. In particular, the expression means an increase by ≥100% when compared to the number of proliferating cells at the beginning of therapy. In this context, the experimental determination and quantification will be performed using standard methods, e.g. the quantification of the protein Ki67, which is strictly associated with cell proliferation. For quantification of proliferating hepatocytes in a tissue slide, several immunohistochemical standard methods are available, which use a primary anti-Ki67 antibody followed by visualization of anti-Ki67-binding by using, for example, a horseradish peroxidase conjugated secondary antibody. The amount of peroxidase activity, which is visualized by enzymatic conversion of chromogenic substrates, correlates with the amount of Ki67 protein and the number of proliferating cells.

In the experiments described below, hepatocyte proliferation was quantified by Ki67-staining using the primary polyclonal rabbit anti-Ki67 antibody from Abcam (article no. ab15580, Abcam, Cambridge, USA) and the fluorophore tetramethylrhodamine containing secondary goat polyclonal antibody from Invitrogen (article no. 16101, Invitrogen/ThermoFisher). Based on data obtained from several pre-clinical mouse models it was found that shRNA (small hairpin RNA) mediated suppression of MKK4 in a chronic $CCl_4$ (carbon tetrachloride) mediated liver damage mouse model increased hepatocyte proliferation from 13% to 27% (compared to a control shRNA) and was associated with decreased liver damage (transaminases) and decreased liver fibrosis. According to the definition in the previous chapter, the relative increase of proliferating cells was 108%. In a model of alcohol induced steatohepatitis (ASH), shRNA mediated silencing of MKK4 resulted in a hepatocyte proliferation rate of 4% as compared to 2% when a control shRNA was used (relative increase: 100%). The duplication of hepatocyte proliferation was associated with decreased steatosis (fat deposition) and decreased liver damage as measured by transaminases. Along the same lines, shRNA mediated MKK4 silencing increased hepatocyte proliferation from 16% (control shRNA) to 33% (relative increase: 106%) in a model of partial hepatectomy (48 hrs after surgical removal of two thirds of the liver). Again, increased hepatocyte proliferation was associated with improved liver regeneration and a faster restoration of liver mass. In conclusion, these studies validate MKK4 as a therapeutic target for treatment of acute and chronic liver diseases. Furthermore, WO 2018/134254 discloses new compounds, which inhibit MKK4 selectively over MKK7 and JNK1. In experimental in vitro and in vivo models of liver regeneration, these compounds were effective in the prevention of acute liver failure induced by administration of a Jo2 antibody and induced the proliferation of isolated primary mouse hepatocytes.

The new compounds disclosed in the present application are potent MKK4 inhibitors with selectivity against MKK7 and JNK1 and therefore, in analogy to the compounds disclosed in WO 2018/134254 can be used for treatment of liver disease and for promoting liver regeneration or reducing or preventing hepatocyte death.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine or chlorine and preferably fluorine.

Alkyl is a straight-chain or branched alkyl group which is preferably a $C_1$-$C_6$-alkyl group, i.e. an alkyl group having from 1 to 6 carbon atoms, and more preferably a $C_1$-$C_4$-alkyl group and in particular a $C_1$-$C_3$-alkyl group. Examples of an alkyl group are methyl, ethyl, n-propyl, iso-propyl, n-butyl, 2-butyl, iso-butyl, tert-butyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The definition of alkyl is likewise applicable to any group which includes an alkyl group, such as alkoxy, alkylsulfinyl, phenylalkyl, etc.

Haloalkyl is a halogenated alkyl group as defined above, wherein at least one, e.g. 1, 2, 3, 4 or all of the hydrogen atoms are replaced by 1, 2, 3, 4 or a corresponding number of identical or different halogen atoms, such as trifluoromethyl, chloromethyl, bromomethyl, difluoromethyl, fluoromethyl, difluoroethyl, etc. Particular examples include the fluorinated $C_1$-$C_4$ alkyl groups as defined, such as trifluoromethyl, difluoromethyl, fluoromethyl, or difluoroethyl.

Cycloalkyl is a cycloaliphatic radical which is preferably $C_3$-$C_8$-cycloalkyl, i.e. a cycloalkyl group having from 3 to 8 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

The compounds of the invention can be prepared as disclosed in WO 2010/111527 which is incorporated herein in its entirety by reference or according to analogous procedures. The acid or base addition salts are prepared in a customary manner by mixing the free base with a corresponding acid or by mixing the free acid with the desired base. Optionally, the reaction is carried out in solution in an organic solvent, for example a lower alcohol, such as MeOH, ethanol or propanol, an ether, such as methyl tert-butyl ether or diisopropyl ether, a ketone, such as acetone or methyl ethyl ketone, or an ester, such as EtOAc.

The compounds of the invention are useful for promoting liver regeneration or reducing or preventing hepatocyte death and, at the same time, increasing hepatocyte proliferation. The compounds are therefore useful in treating, modulating, improving or preventing diseases which involve acute or chronic damages to the liver that may be caused by infection, injury, exposure to toxic compounds, an abnormal build-up of normal substances in the blood, an autoimmune process, a genetic defect or unknown causes.

Such liver diseases comprise all diseases where increased liver regeneration and reduction or prevention of hepatocyte death may be helpful to achieve a potential therapeutic effect, i.e. partial or complete restoration of liver functions. Such diseases comprise acute and chronic or acute on chronic liver diseases such as acute and chronic viral hepatitis like hepatitis B, C, E, hepatitis caused by Epstein-Barr virus, cytomegalovirus, herpes simplex virus and other viruses, all types of autoimmune hepatitis, primary sclerosing hepatitis, alcoholic hepatitis;

metabolic liver diseases such as metabolic syndrome, fatty liver like non-alcoholic fatty liver (NAFL), non-alcoholic steatohepatitis (NASH), alcoholic steatohepatitis (ASH), Morbus Wilson, Hemochromatosis, alpha1-antitrypsin deficiency, glycogen storage diseases;

all types of liver cirrhosis, such as primary biliary cirrhosis, ethyl toxic liver cirrhosis, cryptogenic cirrhosis;

acute (fulminant) or chronic liver failure such as toxic liver failure like acetaminophen (paracetamol) induced liver failure, alpha-amanitin induced liver failure, drug induced hepatotoxicity, liver failure caused, for example, by antibiotics, nonsteroidal anti-inflammatory drugs and anticonvulsants, acute liver failure induced by herbal supplements (kava, ephedra, skullcap, pennyroyal etc), liver disease and failure due to vascular diseases such as Budd-Chiari syndrome, acute liver failure of unknown origin, chronic liver disease due to right heart failure;

galactosemia, cystic fibrosis, porphyria, hepatic ischemia perfusion injury, small for size syndrome after liver transplantation, primary sclerosing cholangitis or hepatic encephalopathy.

For promoting liver regeneration or reducing or preventing hepatocyte death the compounds of the invention are administered to a patient in need thereof in a therapeutically effective amount. Various diagnostic methods are available to detect the presence of a liver disease. Blood levels of alanine aminotransferase (ALT) and aspartate aminotransferase (AST), above clinically accepted normal ranges, are known to be indicative of on-going liver damage. Blood bilirubin levels or other liver enzymes may be used as detection or diagnostic criteria. Routine monitoring of liver disease patients for blood levels of ALT and AST is used to measure progress of the liver disease while on medical treatment. Reduction of elevated ALT and AST levels to within the accepted normal range is taken as clinical evidence reflecting a reduction in the severity of the patients' liver damage. Commercial assays such as FibroTest/FibroSURE, HepaScore®, FibroMeter or Cirrhometer evaluate the combined results of five and more biochemical parameters for the detection of liver steatosis, fibrosis and cirrhosis. Furthermore, non-invasive, innovative physical imaging techniques such as magnetic resonance imaging, sonography and, in particular, elastography techniques are available to detect and monitor the status and progression of liver diseases.

It has further been found that shRNA mediated MKK4 suppression attenuate TNF-$\alpha$-driven cartilage matrix degradation in osteoarthritis (Cell Death and Disease (2017) 8, e3140). Therefore, inhibition of the activity of MKK4 using the compounds of the invention are further useful for treating osteoarthritis and rheumatoid arthritis.

Furthermore, MKK4 inhibitors may also be useful for treatment of neurodegenerative diseases such as Alzheimer's disease and Parkinson's disease. Grueninger et al. found that in human neuroblastoma cells, MKK4 plays a key role in the phosphorylation of Tau protein at serine 422 which promotes Tau aggregation (Mol Cell Biochem (2011) 357: 199-207). Inhibitors of Tau phosphorylation which prevents the aggregation of Tau are being considered useful for prevention or treatment of Alzheimer's disease.

Recently, a MKK4 inhibitor has been described with potent neuroprotective effects in vitro and in vivo. In hippocampal cultures, the incubation with an MKK4-inhibitor prevented glutamate-induced cell death and caspase-3 activation, and also inhibited N-Methyl-4-phenylpyridinium iodide- and amyloid β1-42-induced cell death in SH-SY5Y cells. The same compound also alleviated 1-methyl-4-phenyl-1,2,3,6-tetrahydropyridine-induced degeneration of nigrostriatal dopaminergic neurons in mice (Biochemical Pharmacology (2018), Vol. 162, April 2019, 109-122; doi: https://doi.org/10.1016/j.bcp.2018.10.008).

The compounds of the invention are customarily administered in the form of pharmaceutical compositions which comprise at least one compound according to the invention, optionally together with an inert carrier (e.g. a pharmaceutically acceptable excipient) and, where appropriate, other drugs. These compositions can, for example, be administered orally, rectally, transdermally, subcutaneously, intraperitoneally, intravenously, intramuscularly or intranasally.

Examples of suitable pharmaceutical compositions are solid medicinal forms, such as powders, granules, tablets, in particular film tablets, lozenges, sachets, cachets, sugar-coated tablets, capsules, such as hard gelatin capsules and soft gelatin capsules, or suppositories, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resins; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], $4^{th}$ edition, Aulendorf: ECV-Editio-Cantor-Verlag, 1996.

The compounds of the invention may also be suitable for combination with other therapeutic agents. The invention therefore further relates to a combination comprising a compound of the invention with one or more further therapeutic agents, in particular for use in promoting liver regeneration or reducing or preventing hepatocyte death. The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of the invention and at least one further therapeutic agent are within the scope of the current invention. In one embodiment of adjunctive therapeutic administration as described herein, a patient is typically stabilized on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

Suitable agents for use in combination with the compounds of the inventions include for example:

- ACC inhibitors such as TOFA (5-(tetradecyloxy)-2-furoic acid), firsocostat (formerly known as GS 0976), PF-05221304 and ACC inhibitors as disclosed in WO 2016/112305,
- angiotensin II receptor antagonists,
- angiotensin converting enzyme (ACE) inhibitors, such as enalapril,
- ASK1 (Apoptosis signal-regulating kinase 1, MAP3K5) inhibitors such as selonsertib (formerly known as GS-4997) or SRT-015
- caspase inhibitors, such as emricasan,
- cathepsin B inhibitors, such as a mixed cathepsin B/hepatitis C virus NS3 protease inhibitor. like VBY-376,
- CCR2 chemokine antagonists, such as a mixed CCR2/CCR5 chemokine antagonist like cenicriviroc,
- CCR5 chemokine antagonists,
- chloride channel stimulators, such as cobiprostone,
- cholesterol solubilizers,
- copper amine oxidase 3 (AOC3) inhibitors, such as BI 1467335 (formerly known as PXS-4728A)
- diacylglycerol O-acyltransferase 1 (DGAT1) inhibitors, such as LCQ908 or GSK-3008356,
- diacylglycerol O-acyltransferase 2 (DGAT2) inhibitors, such as PF-06865571,
- dipeptidyl peptidase IV (DPPIV) inhibitors, such as linagliptin,
- farnesoid X receptor (FXR) agonists, such as INT-747 (obeticholic acid), cliofexor (formerly known as GS-9674 or PX-102), tropifexor (formerly known as LJN452), EDP-305 or LMB-763,
- Fibroblast growth factors (FGF) and analogues thereof, such long-acting analogues of FGF19 (e.g. aldafermin, formerly known as NGM-282) or long-acting analogues of FGF21 (e.g. TEV-47948, also denominated Bio89-100, or ARK01 or PF-05231023)
- FXR/TGR5 dual agonists, such as INT-767,
- galectin-3 inhibitors, such as GR-MD-02,
- glucagon-like peptide 1 (GLP1) agonists, such as liraglutide or exenatide,
- glucagon-like peptide 1 (GLP1)/glucagon dual agonists, such as cotadutide, dual glucose-dependent insulinotropic polypeptide (GIP) and glucagon-like peptide-1 (GLP-1) receptor agonists such as tirzepatide (formerly known as LY3298176)

glutathione precursors, hepatitis C virus NS3 protease inhibitors, such as a mixed cathepsin B/hepatitis C virus NS3 protease inhibitor like VBY-376, HMG CoA reductase inhibitors, such as a statin like atorvastatin, 11ß-hydroxysteroid dehydrogenase (11ß-HSD1) inhibitors, such as R05093151, IL-1ß antagonists, IL-6 antagonists, such as a mixed IL-6/IL-1ß/TNFα ligand inhibitor like BLX-1002, IL-10 agonists, such as peg-ilodecakin, anti-IL-11 antibodies or IL-11 antagonists IL-17 antagonists, such as KD-025, ileal sodium bile acid cotransporter inhibitors, such as volixibat (formerly known as SHP-626), integrin inhibitors, such as selective αvβ1-inhibitors (e.g. PLN-1474 or those reviewed in Wilkinson et al., Eur. J. Pharmacol., 842, 239-247 (2019)), ketohexokinase inhibitors such as PF-06835919 leptin analogs, such as metreleptin, 5-lipoxygenase inhibitors, such as a mixed 5-lipoxygenase/PDE3/PDE4/PLC inhibitor like tipelukast, LPL gene stimulators, such as alipogene tiparvovec, lysyl oxidase homolog 2 (LOXL2) inhibitors, such as an anti-LOXL2 antibody like simtuzumab (formerly known as GS-6624) or small molecule inhibitors such as those disclosed in WO 2017/136870, nod-like receptor family pyrin domain containing 3 (NLRP3) inflammasome small molecule inhibitors, such as MCC950, omega-3 polyunsaturated fatty acids and deriviatives thereof, such as icosabutate and examples disclosed in U.S. Pat. No. 8,735,436 B2, oxysterol sulfates, such as 25-hydroxycholesterol 3-sulfate and 25-hydroxy-cholesterol 3, 25-disulfate, PDE4 inhibitors, such as ASP-9831

PPARα agonists, such as a mixed PPARα/δ agonist elafibranor (formerly known as GFT-505), the mixed PPARα/γ/δ agonist lanifibranor or the mixed PPARα/γ agonist saroglitazar), PPARγ agonists, such as pioglitazone, PPARδ agonists such as seladelpar, Rho associated protein kinase 2 (ROCK2) inhibitors, such as KD-025, sodium glucose transporter-2 (SGLT2) inhibitors, such as remogliflozin etabonate, sodium glucose transporter-½ (SGLT½) inhibitors such as licogliflozin stearoyl CoA desaturase-1 inhibitors, such as aramchol or CVT-12805, thyroid hormone receptor ß agonists, such as MGL-3196 or VK2809, tumor necrosis factor α (TNFα) ligand inhibitors, transglutaminase inhibitors and transglutaminase inhibitor precursors, such as mercaptamine, PTPIb inhibitors, such as A119505, A220435, A321842, CPT633, ISIS-404173, JTT-551, MX-7014, MX-7091, MX-7102, NNC-521246, OTX-001, OTX-002, or TTP814, and Namacizumab, an antibody, which stabilizes the cannabinoid 1 receptor (CB1) in an inactive conformation.

In some embodiments, the one or more further therapeutic agents are selected from acetylsalicylic acid, alipogene tiparvovec, aramchol, atorvastatin, BLX-1002, cenicriviroc, cobiprostone, colesevelam, emricasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, GS-9674, remogliflozin etabonate, SHP-626, solithromycin, tipelukast, TRX-318, ursodeoxycholic acid, and VBY-376.

In some embodiments, one of the one or more further therapeutic agents is selected from acetylsalicylic acid, alipogene tiparvovec, aramchol, atorvastatin, BLX-1 002, and cenicriviroc.

In an embodiment the invention relates to a method of inhibiting protein kinase MKK4, selectively inhibiting protein kinase MKK4 over protein kinases JNK1 and MKK7, promoting liver regeneration or preventing hepatocyte death, treating acute, acute-on-chronic or chronic liver disease, treating acute and chronic or acute on chronic liver diseases such as acute and chronic viral hepatitis like hepatitis B, C, E, hepatitis caused by Epstein-Barr virus, cytomegalovirus, herpes simplex virus and other viruses, all types of autoimmune hepatitis, primary sclerosing hepatitis, alcoholic hepatitis;

treating metabolic liver diseases such as metabolic syndrome, fatty liver like non-alcoholic fatty liver (NAFL), non-alcoholic steatohepatitis (NASH), alcoholic steatohepatitis (ASH), Morbus Wilson, hemochromatosis, alpha1-antitrypsin deficiency, glycogen storage diseases;

treating all types of liver cirrhosis, such as primary biliary cirrhosis, ethyl toxic liver cirrhosis, cryptogenic cirrhosis;

treating acute (fulminant) or chronic liver failure such as toxic liver failure like acetaminophen (paracetamol) induced liver failure, alpha-amanitin induced liver failure, drug induced hepatotoxicity and liver failure caused, for example, by antibiotics, nonsteroidal anti-inflammatory drugs, anticonvulsants, acute liver failure induced by herbal supplements (kava, ephedra, skullcap, pennyroyal etc.), liver disease and failure due to vascular diseases such as Budd-Chiari syndrome, acute liver failure of unknown origin, chronic liver disease due to right heart failure;

treating galactosemia, cystic fibrosis, porphyria, hepatic ischemia perfusion injury, small for size syndrome after liver transplantation, primary sclerosing cholangitis or hepatic encephalopathy, treating osteoarthritis, rheumatoid arthritis, or CNS-related diseases such as Alzheimer disease and Parkinson disease, which comprises administering an effective amount of a compound or a composition as defined above to a subject in need thereof.

In an embodiment, the compounds of the invention are administered in a dosage of 0.2 to 15 mg/kg or 0.5 to 12 mg/kg of the subject being treated. The compounds can be administered once or several times a day. The compounds are administered over 4 to 12 weeks.

The following examples illustrate the invention without limiting it.

EXAMPLES

Abbreviations:

$Boc_2O$ di-tert.-butyloxycarbonate

CPME cyclopentylmethyl ether

DCM dichloromethane
4-DMAP 4-dimethylaminopyridine
DME dimethyl ether
DMF dimethylformamide
DMSO dimethylsulfoxide
EtOAc ethyl acetate
HPLC high performance liquid chromatography
KOH potassium hydroxide
LDA lithium diisopropylamide
MeCN acetonitrile
MeOH methanol
$NaHCO_3$ sodium bicarbonate
$NH_4Cl$ ammonium chloride
$Na_2SO_4$ sodium sulfate
O/N over night
$PdCl_2(PPh_3)_2$ bis(triphenylphosphine)palladium(II) dichloride
$Pd(dppf)Cl_2$ DCM 1,1'-bis(diphenylphosphino)ferrocene dichloropalladium(II), complex with DCM
$Pd_2(dba_3)$ tris(dibenzylideneacetone)dipalladium(0)
pTSA para-toluenesulfonic acid
PE petrolether
RT room temperature
TEA triethylamine
THF tetrahydrofurane
TLC thin layer chromatography
Xantphos 4,5-bis(diphenylphosphino)-9,9-dimethylxanthene

Example 1: Synthesis of N-(3-(5-(2-cyclopropylpyrimidin-5-yl)-1H-pyrazolo[3,4-b]pyridine-3-carbonyl)-2,4-difluorophenyl)-1-phenylmethanesulfonamide

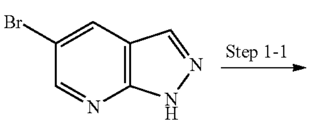

(I)

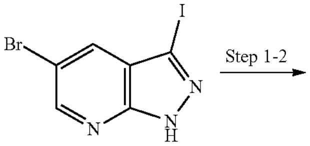

(II)

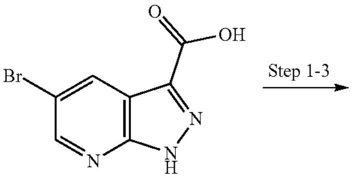

(III)

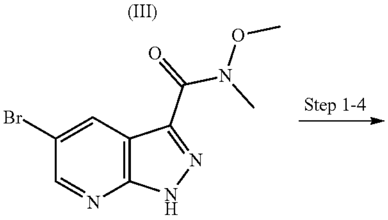

(IV)

-continued

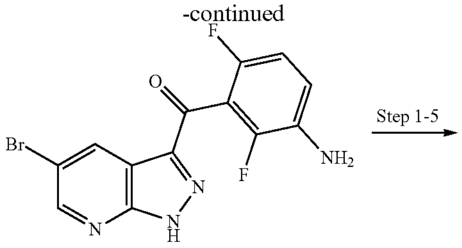

(V)

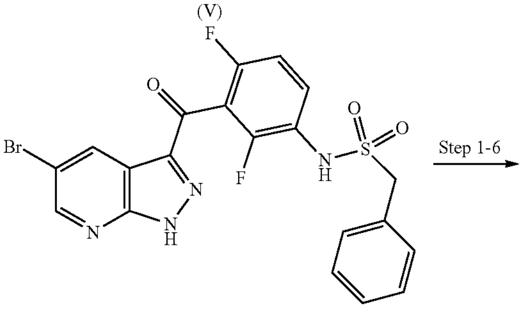

(VI)

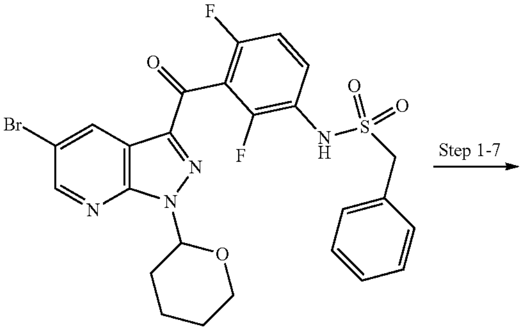

(VII)

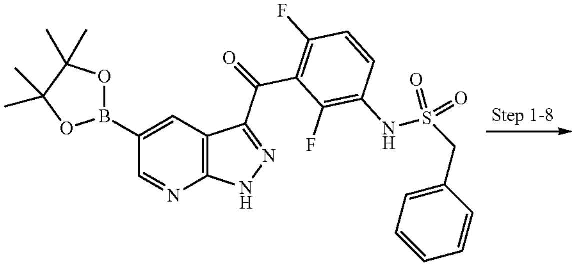

(VIII)

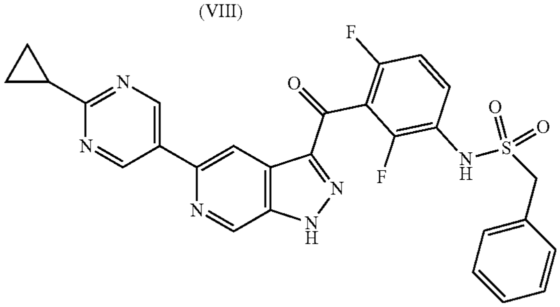
(IX)

Step 1-1: 5-Bromo-3-iodo-1H-pyrazolo[3,4-b]pyridine (II)

To a stirred mixture of 5-bromo-1H-pyrazolo[3,4-b]pyridine ((I), 6.81 g, 34.4 mmol) and potassium hydroxide (KOH, 6.75 g, 120.4 mmol) in DMF (45 mL) was added iodine (9.60 g, 37.8 mmol) in one portion at RT. After a short induction period the exothermic reaction began. After 1 h, an additional 1 g portion of iodine was added, and the mixture was stirred at 45° C. for 1 h. The mixture was poured into 300 mL of a dilute solution of $Na_2SO_3$ and acidified with 2N HCl. The solids were collected by suction filtration, washed with water and dried in an oven at 110° C. Yield: 10.92 g, Analytical Data:

HPLC purity: 95%, $^1$H NMR (200 MHz, DMSO) δ 14.29 (s, 1H), 8.62 (s, 1H), 8.17 (s, 1H); $^{13}$C NMR (50 MHz, DMSO) δ 150.53, 150.17, 131.86, 120.58, 112.43, 91.95;

MS(ESI$^-$): m/z 322.0/324.0 [M−H]$^-$.

Step 1-2: 5-Bromo-1H-pyrazolo[3,4-b]pyridine-3-carboxylic acid (III)

5-Bromo-3-iodo-1H-pyrazolo[3,4-b]pyridine ((II), 10.44 g, 32.2 mmol) was combined with DMF, MeOH and triethylamine (TEA, 75 mL each). The vessel was evacuated and flushed with argon (4×). XantPhos (1.12 g, 1.93 mmol) and $Pd(OAc)_2$ (217 mg, 0.97 mmol) were added and carbon monoxide (generated from formic acid and sulfuric acid) was bubbled through the solution while heating to 60° C. The mixture was stirred under an atmosphere of carbon monoxide (balloon) for 8 h. Every 1.5 h carbon monoxide was bubbled through the solution for 5 minutes. The mixture was concentrated under reduced pressure and the residue was triturated with 2N HCl. The solids were heated at 95° C. in about 100 mL 1N NaOH over night (O/N). After cooling to RT, the mixture was acidified with conc. HCl and the precipitate collected by suction filtration and washed with water. The solids were dried in an oven at 110° C. to constant mass. The solids were sonicated in 100 mL of toluene for 5 minutes and stirred for 30 minutes. The product was filtered, washed with an additional 20 mL of toluene and dried at 110° C. Yield: 7.92 g.

Analytical Data:

HPLC purity: >99%, $^1$H NMR (200 MHz, DMSO) δ 8.64 (d, J=7.9 Hz, 2H), 5.69 (bs, 1H); $^{13}$C NMR (50 MHz, DMSO) δ 163.27, 150.97, 149.67, 136.69, 132.65, 115.73, 113.6;

MS(ESI$^-$): m/z 239.9/241.9 [M−H]$^-$.

Step 1-3: 5-bromo-N-methoxy-N-methyl-1H-pyrazolo[3,4-b]pyridine-3-carboxamide (IV)

5-Bromo-1H-pyrazolo[3,4-b]pyridine-3-carboxylic acid ((III), 7.91 g, 32.7 mmol) and 1,1'-carbonyldiimidazole (5.83 g, 35.9 mmol) were stirred in 200 mL of DMF at 60° C. for 45 minutes. To the resulting suspension was added N,O-dimethylhydroxylamine hydrochloride (3.51 g, 35.9 mmol) and the mixture was stirred for 4 h at 65° C. Most of the solvent was removed under vacuum and to the residue half sat. $NaHCO_3$-solution was added. The solids were collected by suction filtration, washed with water and dried at 110° C. Yield: 7.94 g, Analytical Data:

HPLC purity: 96%, $^1$H NMR (200 MHz, DMSO) δ 14.46 (s, 1H), 8.62 (d, J=20.4 Hz, 2H), 3.76 (s, 3H), 3.44 (s, 3H), MS(ESI$^-$): m/z 283.0/285.0 [M−H]$^-$ Step 1-4: Synthesis of (3-amino-2,6-difluorophenyl)(5-bromo-1H-pyrazolo[3,4-b]pyridin-3-yl)methanone (V)

2,4-Difluoroaniline (6.25 g, 48.4 mmol) was dissolved in 50 mL dry THF and cooled to −78° C. under an atmosphere of argon. 2.5 M n-butyllithium in hexane (19.4 mL, 48.4 mmol) was added dropwise. After 15 minutes 1,2-bis(chlorodimethylsilyl)ethane (10.9 g, 49.5 mmol) in 15 mL dry THF was added dropwise and the mixture was stirred for 30 minutes. 2.5 M n-butyllithium in hexane (19.4 mL, 48.4 mmol) was added dropwise and the mixture was allowed to reach RT within 1 h. After cooling to −78° C. 2.5 M n-butyllithium in hexane (19.4 mL, 48.4 mmol) was added dropwise and stirred for 1 h at −78° C. (=solution A). 5-bromo-N-methoxy-N-methyl-1H-pyrazolo[3,4-b]pyridine-3-carboxamide ((IV), 6.00 g, 21.1 mmol) was suspended in 50 mL dry THF and cooled to 0° C. under an atmosphere of argon. NaH (60% in mineral oil, 0.88 g, 22.1 mmol) was added portionwise and the solution was stirred at RT for 1 h. (=solution B).

Solution B was added dropwise to solution A at −78° C. After complete addition, the mixture was warmed to RT within 30 minutes. 12 mL conc. HCl were added carefully and the mixture was stirred for 30 minutes. Solid $NaHCO_3$ was added to neutralize the solution, the solids were filtered off and washed with THF. The filtrate was evaporated and the residue triturated with MeOH and water and dried at 110° C. Yield: 4.03 g;

Analytical Data:

HPLC purity: 97%, $^1$H NMR (200 MHz, DMSO-$d_6$) δ 14.91 (s, 1H), 8.77 (dd, J=5.4, 2.1 Hz, 2H), 7.18-6.59 (m, 2H), 5.25 (s, 2H); $^{13}$C NMR (50 MHz, DMSO) δ 183.95, 151.04, 150.79, 150.27 (dd, J=161.0, 6.8 Hz), 145.50 (dd, J=167.3, 6.8 Hz), 141.34, 133.35 (dd, J=12.8, 2.6 Hz), 132.28, 117.45 (dd, J=8.4, 6.5 Hz), 116.24 (dd, J=22.7, 19.1 Hz), 115.55, 114.81, 111.26 (dd, J=21.7, 3.5 Hz); MS(ESI$^-$): m/z 351.1/353.1 [M−H]$^-$.

Step 1-5: N-(3-(5-bromo-1H-pyrazolo[3,4-b]pyridine-3-carbonyl)-2,4-difluorophenyl)propane-1-sulfonamide (VI)

(3-amino-2,6-difluorophenyl)-(5-bromo-1H-pyrazolo[3,4-b]pyridin-3-yl)methanone (579 mg, 1.64 mmol) and 4-dimethylaminopyridine (4-DMAP, 0.401 g, 3.28 mmol) were dissolved in pyridine (3.31 mL, 41.0 mmol) with heating. After cooling to −10° C. phenylmethanesulfonyl chloride (406 mg, 2.13 mmol) was added to the formed suspension. The mixture was stirred for 10 minutes at −10° C., for another 10 minutes at RT, followed by warming to 50° C. and stirring for 30 minutes. The mixture was concentrated under reduced pressure, reconstituted in 2N NaOH (2.46 mL, 4.92 mmol) and stirred at RT for 10 minutes. The mixture was diluted with water and slowly added to 25 mL 2N HCl with stirring. After 10 minutes, the formed solid was collected by suction filtration, washed with water and dried at 75° C. (0.590 g, 1.16 mmol, 71% yield).

Analytical Data:

$^1$H NMR (200 MHz, $CDCl_3$) δ 14.22 (s, 1H), 8.96 (s, 1H), 8.79 (d, J=2.2 Hz, 1H), 8.59 (d, J=2.1 Hz, 1H), 7.52-7.25 (m, 6H), 6.87 (td, J=9.1, 1.6 Hz, 1H), 4.32 (s, 2H);

MS(ESI$^-$): m/z 504.7 [M−1]$^-$.

Step 1-6: N-[3-[5-bromo-1-(oxan-2-yl)pyrazolo[3,4-b]pyridine-3-carbonyl]-2,4-difluorophenyl]-1-phenylmethanesulfonamide (VII)

N-[3-(5-bromo-1H-pyrazolo[3,4-b]pyridine-3-carbonyl)-2,4-difluorophenyl]-1-phenylmethanesulfonamide (0.419 g, 0.826 mmol), p-toluenesulfonic acid (p-TSA) monohydrate (15.7 mg, 0.0826 mmol) and dihydropyran (0.0904 mL, 0.991 mmol) were dissolved in 4.13 ml DCM and refluxed for 1.5 h. After cooling, the mixture was diluted with DCM, washed with saturated $NaHCO_3$-solution, dried and filtered. n-Heptane was added and DCM removed. After cooling in an ice bath, the product was collected by suction filtration. (0.393 g, 0.6650 mmol, 80% yield).

Analytical Data:

$^1$H NMR (200 MHz, $CDCl_3$) δ 8.88 (d, J=1.8 Hz, 1H), 8.68 (d, J=1.8 Hz, 1H), 7.62 (td, J=9.0, 5.6 Hz, 1H), 7.34 (s, 5H), 6.96 (t, J=8.1 Hz, 1H), 6.48 (s, 1H), 6.14 (dd, J=9.8, 2.0 Hz, 1H), 4.39 (s, 2H), 4.03 (d, J=11.1 Hz, 1H), 3.90-3.56 (m, 1H), 2.56-2.36 (m, 1H), 2.09-1.46 (m, 5H);

MS(ESI$^-$): m/z 591.3/589.4 [M−H]$^-$.

Step 1-7: N-[2,4-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]-1-phenylmethanesulfonamide (VIII)

A vessel was charged with N-[3-[5-bromo-1-(oxan-2-yl)pyrazolo[3,4-b]pyridine-3-carbonyl]-2,4-difluorophenyl]-1-phenylmethanesulfonamide (0.365 g, 0.617 mmol), bis(pinacolato)diboron (0.313 g, 1.23 mmol), potassium acetate (0.182 g, 1.85 mmol) and DMF (3.09 mL). The mixture was heated to 90° C. and the vessel was evacuated and filled with argon (3×). Bis(triphenylphosphine)palladium(II) dichloride ($PdCl_2(PPh)_3)_2$, 4.33 mg, 0.00617 mmol) was added and the reaction was stirred for 4 h at 90° C. After cooling, the reaction was concentrated, taken up in EtOAc and washed with water, half saturated brine and brine, dried and filtered. To the filtrate, activated charcoal was added and the mixture was refluxed for 15 minutes. After cooling, the mixture was filtered over celite and the solvent was removed. The residue was taken up in small amount of DCM, n-heptane was added, and DCM was removed under reduced pressure. The solids were collected by suction filtration and washed with n-hexane and dried the product as off-white solid (0.298 g, 0.4670 mmol, 76% yield), which was used without further purification.

Analytical Data:

$^1$H NMR (200 MHz, $CDCl_3$) δ 9.16 (s, 1H), 8.97 (s, 1H), 7.63 (td, J=9.1, 5.7 Hz, 1H), 7.34 (s, 5H), 6.96 (t, J=8.6 Hz, 1H), 6.45 (s, 1H), 6.23 (d, J=8.8 Hz, 1H), 4.39 (s, 2H), 4.12-3.94 (m, 1H), 3.80 (t, J=9.9 Hz, 1H), 2.60-2.31 (m, 1H), 2.09-1.55 (m, 5H), 1.39 (s, 12H).

Step 1-8: N-(3-(5-(2-cyclopropylpyrimidin-5-yl)-1H-pyrazolo[3,4-b]pyridine-3-carbonyl)-2,4-difluorophenyl)-1-phenylmethanesulfonamide (IX)

A vessel was charged with N-[2,4-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]-1-phenylmethanesulfonamide (0.275 g, 0.431 mmol), 5-bromo-2-cyclopropylpyrimidine (0.111 g, 0.560 mmol), $PdCl_2(PPh)_3)_2$ (3.02 mg, 0.00431 mmol) and 1,4-dioxane (1.44 mL). The vessel was evacuated and filled with argon (3×). Degassed 3M aqueous $K_2CO_3$ (0.431 mL, 1.29 mmol) was added and the mixture was stirred at 60° C. for 1 h. After cooling, the reaction was diluted with EtOAc and neutralized with $NH_4Cl$ solution. The organic phase was dried, evaporated and the main product was isolated by flash chromatography (DCM/EtOAc, 10 to 50%). To remove the THP protection group the isolated product was refluxed in 2.5N HCl (3 mL) for 1 h.

Analytical Data:

$^1$H NMR (200 MHz, DMSO-$d_6$) δ 15.01 (s, 1H), 9.86 (s, 1H), 9.12 (s, 2H), 9.08 (d, J=2.0 Hz, 1H), 8.90 (d, J=2.0 Hz, 1H), 7.60-7.16 (m, 7H), 4.54 (s, 2H), 2.39-2.19 (m, 1H), 1.27-1.04 (m, 4H).

MS(ESI$^-$): m/z 545.5 [M−H]$^-$.

Example 2: Synthesis of N-(3-(5-(4-chlorophenyl)-1H-pyrazolo[3,4-b]pyridine-3-carbonyl)-2,6-difluorophenyl)methanesulfonamide

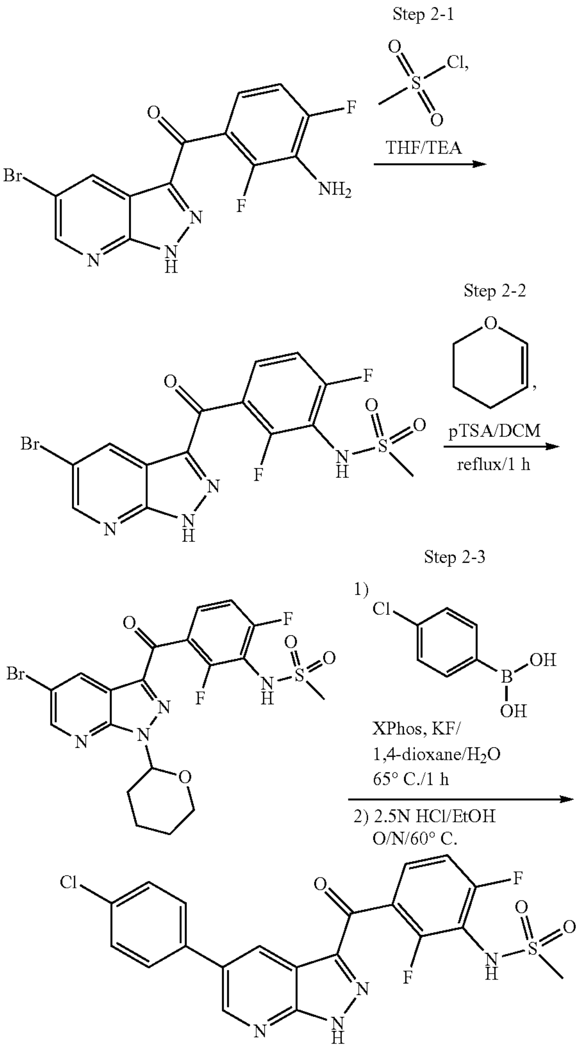

Step 2-1: N-[3-(5-bromo-1H-pyrazolo[3,4-b]pyridine-3-carbonyl)-2,6-difluorophenyl]methane-sulfonamide (3-amino-2,4-difluorophenyl)(5-bromo-1H-pyrazolo[3,4-b]pyridin-3-yl)methanone (1.29 g, 3.65 mmol) was dissolved in 18 ml THF and 5.09 ml TEA (36.5 mmol, 10 eq.). The mixture was warmed to achieve complete dissolution. Then, the solution was cooled to 0° C. followed by addition of 0.99 ml mesylchloride (12.8 mmol, 3.5 eq.). After 10 min., the mixture was allowed to warm to RT, 12 ml 2N KOH was added and the mixture was stirred for 10 min. After acidification with 3N HCl, THF was removed under reduced pressure, the solid was collected by suction filtration, washed with 3N HCl/MeOH (1+1) and dried (1.46 g, 93%).

Analytical Data:

$^1$H NMR (400 MHz, DMSO-$d_6$) δ 14.87 (s, 1H), 9.75 (s, 1H), 8.71 (d, J=13.9 Hz, 2H), 7.85 (d, J=6.6 Hz, 1H), 7.39 (t, J=8.5 Hz, 1H), 3.12 (s, 3H).

MS(ESI$^-$): m/z 431.1/429.1 [M−H]$^-$, 411.1/409.1 [M−H−HF]$^-$.

Step 2-2: N-[3-[5-bromo-1-(oxan-2-yl)pyrazolo[3,4-b]pyridine-3-carbonyl]-2,6-difluorophenyl]methanesulfonamide To a suspension of dihydropyran (0.614 mL, 6.73 mmol) and N-[3-(5-bromo-1H-pyrazolo[3,4-b]pyridine-3-carbonyl)-2,6-difluorophenyl]methanesulfonamide (1.45 g, 3.36 mmol) in 16.8 mL DCM was added p-TSA monohydrate (64.0 mg, 0.336 mmol) and the mixture was refluxed for 1 h. The mixture was diluted with DCM, washed with saturated $NaHCO_3$ solution, dried over $Na_2SO_4$ and concentrated. The residue was taken up in a small amount of acetone and transferred into diethyl ether with stirring. The product was collected by suction filtration and washed with diethyl ether to yield the product as white powder (1.07 g, 2.08 mmol, 62% yield).

Analytical Data:

$^1$H NMR (200 MHz, DMSO-$d_6$) δ 9.78 (s, 1H), 8.80 (dd, J=13.4, 1.6 Hz, 2H), 7.88 (dd, J=14.6, 7.8 Hz, 1H), 7.43 (t, J=9.0 Hz, 1H), 6.14 (d, J=8.6 Hz, 1H), 3.94 (d, J=11.6 Hz, 1H), 3.72 (dd, J=14.6, 9.1 Hz, 1H), 3.13 (s, 3H), 2.46-2.19 (m, 1H), 2.00-1.18 (m, 5H);

MS(ESI$^-$): m/z 515.2/513.2 [M−H]$^-$.

Step 2-3: N-[3-[5-(4-chlorophenyl)-1H-pyrazolo[3,4-b]pyridine-3-carbonyl]-2,6-difluorophenyl]methanesulfonamide A vessel was charged with N-[3-[5-bromo-1-(oxan-2-yl)pyrazolo[3,4-b]pyridine-3-carbonyl]-2,6-difluorophenyl]

methanesulfonamide (119 mg, 0.231 mmol), (4-chlorophenyl)boronic acid (36.1 mg, 0.231 mmol), $PdCl_2(PPh)_3)_2$ (3.24 mg, 0.00462 mmol) and purged with argon. Degassed 1,4-dioxane (0.770 mL) and degassed potassium fluoride (95.7 mg, 0.693 mmol) were added and the reaction was stirred at 60° C. for 15 minutes. After cooling, EtOAc and $NH_4Cl$ solution were added and the aqueous phase was discarded. The organic phase was dried over $Na_2SO_4$, concentrated and the residue taken up in 2.5 N HCl (3 mL) in EtOH and stirred at 60° C. O/N. 3 ml isopropanol was added, the solid was collected by centrifugation and the solvent discarded. The solid was taken up in THF/$NaHCO_3$-solution and shaken. The organic phase was dried, the solvent evaporated and the residue triturated with DCM (yield: 44.0 mg, 0.0941 mmol, 41%).

Analytical Data:

$^1$H NMR (400 MHz, DMSO-$d_6$) δ 14.82 (s, 1H), 9.75 (s, 1H), 9.00 (d, J=2.2 Hz, 1H), 8.76 (d, J=2.2 Hz, 1H), 7.90-7.81 (m, 3H), 7.61-7.57 (m, 2H), 7.40 (t, J=8.4 Hz, 1H), 3.11 (s, 3H);

Calculated exact mass: 462.04, MS(ESI$^-$): m/z: 461.0 [M−1]$^-$.

Example 3: Synthesis of N-(3-(5-(4-chlorophenyl)-1H-pyrazolo[3,4-b]pyridine-3-carbonyl)-2,6-difluorophenyl)ethanesulfonamide In analogy to Example 2, N-(3-(5-(4-chlorophenyl)-1H-pyrazolo[3,4-b]pyridine-3-carbonyl)-2,6-difluorophenyl)ethanesulfonamide was prepared.

Analytical Data:

$^1$H NMR (400 MHz, DMSO-$d_6$) δ 9.00 (d, J=2.2 Hz, 1H), 8.76 (d, J=2.2 Hz, 1H), 7.84 (dd, J=13.4, 8.4 Hz, 3H), 7.60 (d, J=8.6 Hz, 2H), 7.38 (t, J=8.6 Hz, 1H), 3.17 (q, J=7.3 Hz, 2H), 1.32 (t, J=7.3 Hz, 3H)

Calculated exact mass: 476.05, MS(ESI$^-$): m/z: 474.9 [M−1]$^-$.

Example 4: Synthesis of Ethyl 4-(3-(2,4-difluoro-3-(methylsulfonamido)benzoyl)-1H-pyrazolo[3,4-b]pyridin-5-yl)benzoate Step 4-1

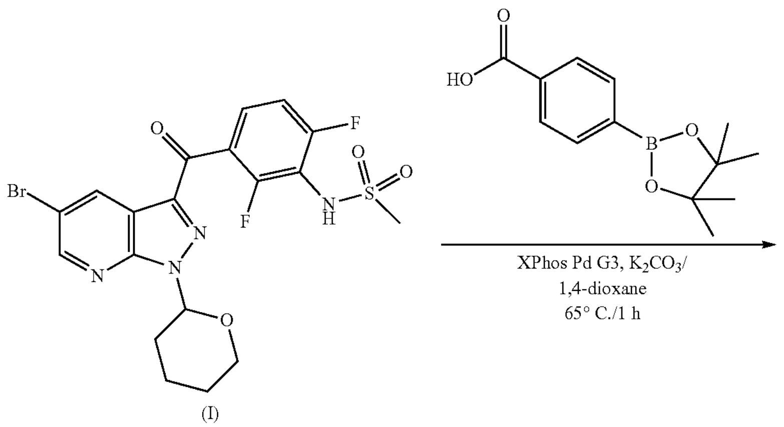

(I)

-continued

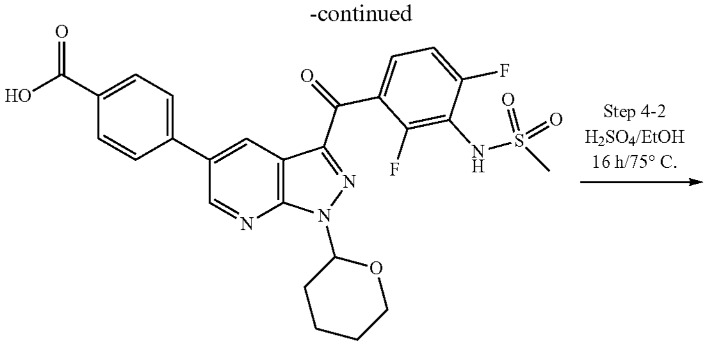

(II)

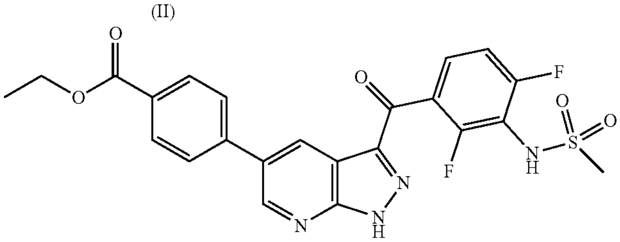

Example 4

Step 4-1: 4-[3-[2,4-difluoro-3-(methanesulfonamido)benzoyl]-1-(oxan-2-yl)pyrazolo[3,4-b]pyridin-5-yl]benzoic acid N-[3-[5-bromo-1-(oxan-2-yl)pyrazolo[3,4-b]pyridine-3-carbonyl]-2,6-difluorophenyl]methanesulfonamide ((I), 355 mg, 0.689 mmol) and 4-(4,4,5,5-tetramethyl-1,3,2-dioxaborolan-2-yl)benzoic acid (188 mg, 0.758 mmol) XPhos Pd G3 ((2-dicyclo-hexylphosphino-2',4',6'-triisopropyl-1,1'-biphenyl)[2-(2'-amino-1,1'-biphenyl)]palladium(II) methanesulfonate, commercially available from Aldrich; 17.5 mg, 0.0207 mmol) were combined in degassed 1,4-dioxane (2.30 mL) and 1.5 M potassium carbonate (2.07 mL, 3.10 mmol). The reaction was evacuated and flushed with argon (3×). XPhos Pd G3 (17.5 mg, 0.0207 mmol) was added and the reaction was stirred at 60° C. (oilbath temperature) for 3 h. After cooling the mixture was acidified with 2N HCl and extracted with EtOAc. The extract was washed with brine, dried over sodium sulfate ($Na_2SO_4$) and concentrated. The residue was purified by flash chromatography (DCM+MeOH 3% to 25%) and triturated with n-hexane (276 mg, 0.4960 mmol, 72% yield).

Step 4-2: Ethyl 5-(3-(2,4-Difluor-3-(methylsulfonamido)benzoyl)-1H-pyrazolo[3,4-b]pyridin-5-yl)benzoat 50 mg (II) (0.09 mmol) was dissolved in a mixture of 300 μl $H_2SO_4$ and 800 μl EtOH and stirred at 75° C. for 16 h. After the mixture was allowed to cool to RT, it was poured into aqueous $NaHCO_3$, the precipitate was collected by centrifugation and washed with water and diethylether (22 mg, 46%, chemical purity (HPLC/UV): 95%).

Analytical Data:

$^1$H NMR (400 MHz, DMSO) δ 14.86 (s, 1H), 9.76 (s, 1H), 9.06 (s, 1H), 8.83 (s, 1H), 8.10 (d, J=7.8 Hz, 2H), 8.04-7.94 (m, 2H), 7.87 (dd, J=14.5, 7.6 Hz, 1H), 7.40 (t, J=8.8 Hz, 1H), 4.35 (q, J=7.0 Hz, 2H), 3.11 (s, 3H), 1.35 (t, J=7.1 Hz, 3H);

Calculated exact mass: 500.10, MS(ESI$^-$): m/z: 499.4 $[M-1]^-$.

Example 5: Synthesis of Methyl 5-(3-(2,4-difluoro-3-(methylsulfonamido)benzoyl)-1H-pyrazolo[3,4-b]pyridin-5-yl)picolinate

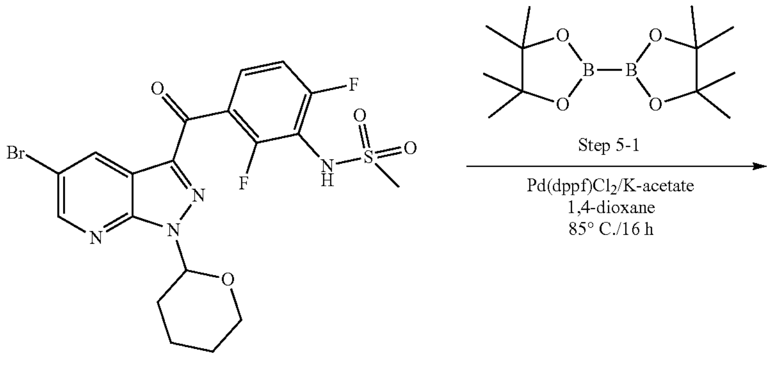

(I)

-continued

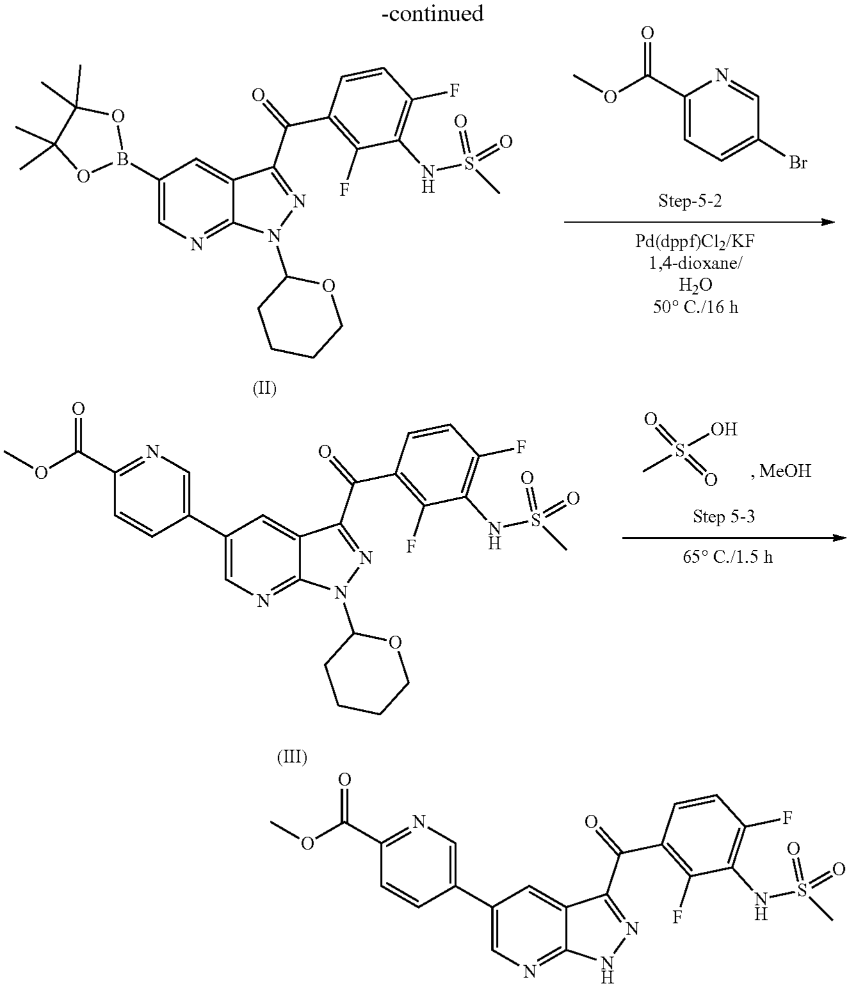

(II)

(III)

Example 5

Step 5-1: N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]methanesulfonamide A vessel was charged with N-[3-[5-bromo-1-(oxan-2-yl)pyrazolo[3,4-b]pyridine-3-carbonyl]-2,6-difluorophenyl]methanesulfonamide ((I), 0.630 g, 1.22 mmol), bis(pinacolato)diboron (341 mg, 1.34 mmol), anhydrous potassium acetate (360 mg, 3.67 mmol) and dry 1,4-dioxane (4.08 mL). The vessel was evacuated and filled with argon (3×). 1,1'-Bis(diphenylphosphino)-ferrocene-dichloropalladium (1:1 complex with DCM) (Pd(dppf)$Cl_2$, 17.9 mg, 0.0245 mmol) was added and the reaction was stirred at 80° C. O/N. After cooling, EtOAc was added, the suspension stirred for 30 minutes and filtered over Celite. The solvent was concentrated, n-heptane was added and the solids were collected by suction filtration, washed with hexane and dried (0.690 g, 1.23 mmol, 100% yield).

Step 5-2: Methyl 5-(3-(2,4-difluoro-3-(methylsulfonamido)benzoyl)-1-(tetrahydro-2H-pyran-2-yl)-1H-pyrazolo[3,4-b]pyridin-5-yl)picolinate A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]methanesulfonamide ((II), 116 mg, 0.206 mmol), methyl 5-bromopyridine-2-carboxylate (49.0 mg, 0.227 mmol), potassium fluoride (36.0 mg, 0.619 mmol), Pd(dppf)$Cl_2$ DCM (8.42 mg, 0.0103 mmol) and degassed 1,4-dioxane/water (4+1) (0.6 mL) and the vessel was evacuated and filled with argon (3×). The mixture was stirred O/N at 50° C., then diluted with EtOAc, washed with brine and the solvents were removed. The product was isolated via flash chromatography (DCM+EtOAc 0% to 20%); 81.0 mg white solid (0.1420 mmol, 69% yield).

Step 5-3: Methyl 5-(3-(2,4-difluoro-3-(methylsulfonamido)benzoyl)-1H-pyrazolo[3,4-b]pyridin-5-yl)picolinate To a solution of methyl 5-[3-[2,4-difluoro-3-(methanesulfonamido)benzoyl]-1-(oxan-2-yl)pyrazolo[3,4-b]pyridin-5-yl]pyridine-2-carboxylate ((III), 60.0 mg, 0.105 mmol) in methanol (0.525 mL) was added methanesulfonic acid (0.0273 mL, 0.420 mmol) and the mixture was stirred at 65° C. for 1.5 h. The mixture was cooled to RT and added slowly to diethyl ether (15 mL). The solid was collected by suction filtration, washed with diethyl ether and dried in vacuo; 36.0 mg white solid (0.0739 mmol, 70% yield).

Analytical Data:
$^1H$ NMR (200 MHz, $CDCl_3$) δ 14.90 (s, 1H), 9.74 (s, 1H), 9.16 (dd, J=12.4, 1.9 Hz, 2H), 8.93 (d, J=2.0 Hz, 1H), 8.47 (dd, J=8.2, 2.3 Hz, 1H), 8.19 (d, J=8.3 Hz, 1H), 7.88 (dd, J=14.8, 7.7 Hz, 1H), 7.41 (t, J=8.7 Hz, 1H), 3.93 (s, 3H), 3.12 (s, 3H);
Calculated exact mass: 487.08; MS($ESI^+$): m/z: 510.4 $[M+Na^+]^+$.
Example 6: Synthesis of N-(2,6-difluoro-3-(5-(pyrimidin-5-yl)-1H-pyrazolo[3,4-b]pyridine-3-carbonyl)phenyl)propane-1-sulfonamide
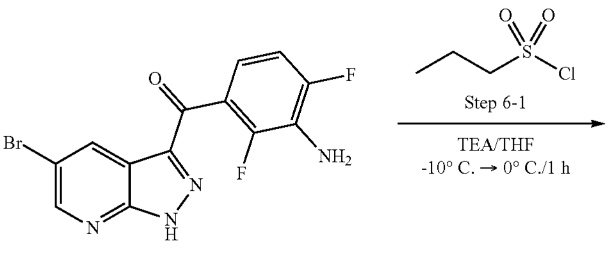
(I)
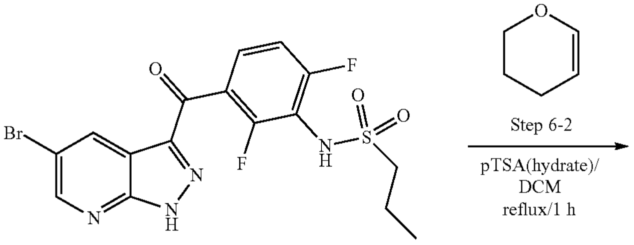
(II)
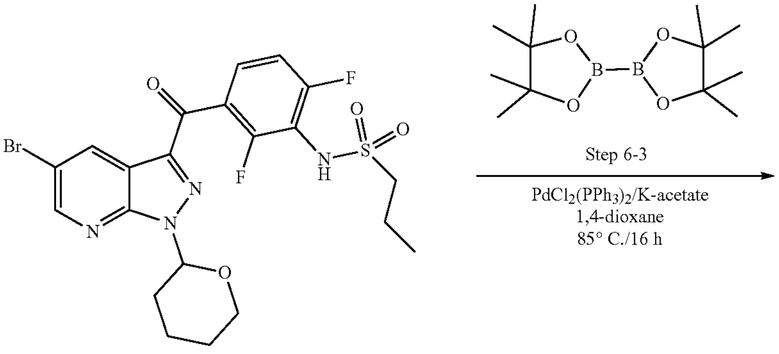
(III)
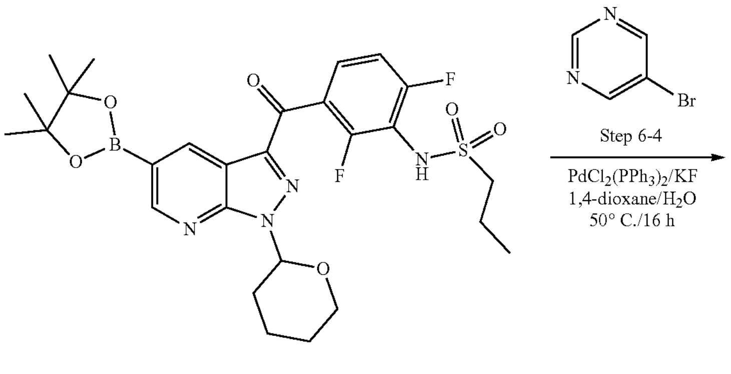
(IV)

-continued

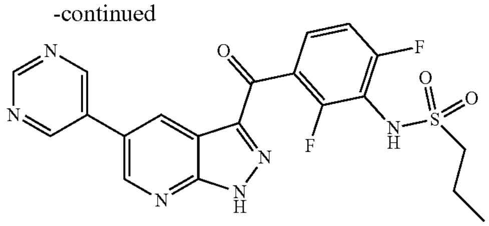

Example 6

Step 6-1: N-[3-(5-bromo-1H-pyrazolo[3,4-b]pyridine-3-carbonyl)-2,6-difluorophenyl]propane-1-sulfonamide To a suspension of (3-amino-2,4-difluorophenyl)-(5-bromo-1H-pyrazolo[3,4-b]pyridin-3-yl)methanone ((I), 65.0 g, 184 mmol) and TEA (282 mL, 2020 mmol) in THF (614 mL), a 1:1 (v/v) mixture of 1-propanesulfonyl chloride (68.4 mL, 607 mmol) and DCM was added dropwise at −10° C. keeping the temperature below −5° C. After complete addition, the mixture was stirred at 0° C. for 1 h. 2N NaOH (736 mL, 1470 mmol) was added and the mixture was stirred at RT for another 30 minutes. THF and TEA were evaporated from the mixture at 45° C. under reduced pressure. The solution was cooled to 20° C. and carefully washed with EtOAc (4×300 mL) with swirling (no shaking). Residual EtOAc was removed under reduced pressure and the solution was added slowly to 3N HCl (736 mL, 2210 mmol) with efficient stirring. The solids were collected by suction filtration, washed with copious amounts of water and dried at 100° C. to yield N-[3-(5-bromo-1H-pyrazolo[3,4-b]pyridine-3-carbonyl)-2,6-difluorophenyl]propane-1-sulfonamide (73.9 g, 161 mmol, 87% yield) as off white solid.

Step 6-2: N-[3-[5-bromo-1-(oxan-2-yl)pyrazolo[3,4-b]pyridine-3-carbonyl]-2,6-difluorophenyl]propane-1-sulfonamide To a suspension of (II) (70.7 g, 154 mmol) in DCM (440 mL) was added p-TSA monohydrate (2.93 g, 15.4 mmol) and dihydropyran (15.5 mL, 169 mmol) and the mixture was refluxed for 1 h. After cooling, the mixture was diluted with 200 mL DCM, washed with sat. $NaHCO_3$ solution and brine and dried over $Na_2SO_4$ and evaporated. The oily residue was taken up in warm (45° C.) MeOH (150 mL), a seeding crystal from a previous synthesis was added and the mixture was stirred at RT. After observed precipitation, the mixture was diluted with cold MeOH, the suspension was cooled to −20° C. for 2 h, the solid was collected by suction filtration and washed with 50 mL MeOH at −20° C. The product was dried at 50° C. in a vacuum oven to yield N-[3-[5-bromo-1-(oxan-2-yl)pyrazolo[3,4-b]pyridine-3-carbonyl]-2,6-difluorophenyl]propane-1-sulfonamide (73.4 g, 135 mmol, 88% yield).

Step 6-3: N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide A vessel was charged with N-[3-[5-bromo-1-(oxan-2-yl)pyrazolo[3,4-b]pyridine-3-carbonyl]-2,6-difluorophenyl]propane-1-sulfonamide ((III), 4.74 g, 8.72 mmol), bis(pinacolato)diboron (4.65 g, 18.3 mmol) and anhydrous potassium acetate (2.57 g, 26.2 mmol). The vessel was evacuated and filled with argon (3×). Dry DMF (29.1 mL) was added and the mixture heated to 90° C. The vessel was evacuated and filled with argon (3×) again. $PdCl_2(PPh_3)_2$ (30.6 mg, 0.0436 mmol) was added under a stream of argon, the vessel was sealed and the reaction stirred at 90° C. for 4 h. After cooling, the reaction was concentrated under reduced pressure, the residue was taken up in approx. 50 ml EtOAc and washed with water, half-saturated NaCl solution and brine. After drying, the extract was filtered, activated charcoal was added and the mixture was heated to reflux temperature for 15 minutes. After cooling, the mixture was filtered over celite, n-heptane (50 mL) was added to the filtrate and the solvents were removed. The solids were stirred in n-hexane (100 mL) for 30 minutes and the product collected by suction filtration. After drying N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (4.37 g, 7.4 mmol, 85% yield) was obtained as colorless solid.

Step 6-4: N-[2,6-difluoro-3-(5-pyrimidin-5-yl-1H-pyrazolo[3,4-b]pyridine-3-carbonyl)phenyl]propane-1-sulfonamide A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide ((IV), 120 mg, 0.203 mmol), 5-bromopyrimidine (35.5 mg, 0.224 mmol), potassium fluoride (35.4 mg, 0.610 mmol), $PdCl_2(PPh_3)_2$ (3.32 mg, 0.00406 mmol) and degassed 1,4-dioxane/water (0.5 mL, (4+1)). The vessel was evacuated and filled with argon (3×) and heated to 60° C. for 2 h. The reaction was acidified with conc. HCl (0.3 mL), diluted with MeOH (0.2 mL) and heated to 60° C. O/N. Another 0.3 mL conc. HCl was added and stirring continued for 4 h. After cooling, the mixture was diluted with water, neutralized with $NaHCO_3$ solution and extracted with THF. The organic phase was washed with brine, dried over $Na_2SO_4$ and evaporated. The residue was purified by flash chromatography (DCM/MeOH, 2% to 8%) and triturated with acetone to yield N-[2,6-difluoro-3-(5-pyrimidin-5-yl-1H-pyrazolo[3,4-b]pyridine-3-carbonyl)phenyl]propane-1-sulfonamide (35.0 mg, 0.0741 mmol, 36% yield).

Analytical Data:

$^1H$ NMR (400 MHz, DMSO-$d_6$) δ 14.87 (s, 1H), 9.71 (s, 1H), 9.28 (d, J=10.4 Hz, 3H), 9.10 (d, J=2.2 Hz, 1H), 8.94 (d, J=2.2 Hz, 1H), 7.87 (dd, J=14.7, 7.6 Hz, 1H), 7.40 (t, J=8.6 Hz, 1H), 3.20-3.07 (m, 2H), 1.89-1.71 (m, 2H), 0.99 (t, J=7.4 Hz, 3H);

Calculated exact mass: 458.10 for $C_{20}H_{16}F_2N_6O_3S$ (molecular weight: 458.44);

MS(ESI$^-$): m/z: 456.9 $[M-1]^-$.

Example 7: Synthesis of N-(2,6-difluoro-3-(5-(2-methylpyrimidin-5-yl)-1H-pyrazolo[3,4-b]pyridine-3-carbonyl)phenyl)propane-1-sulfonamide

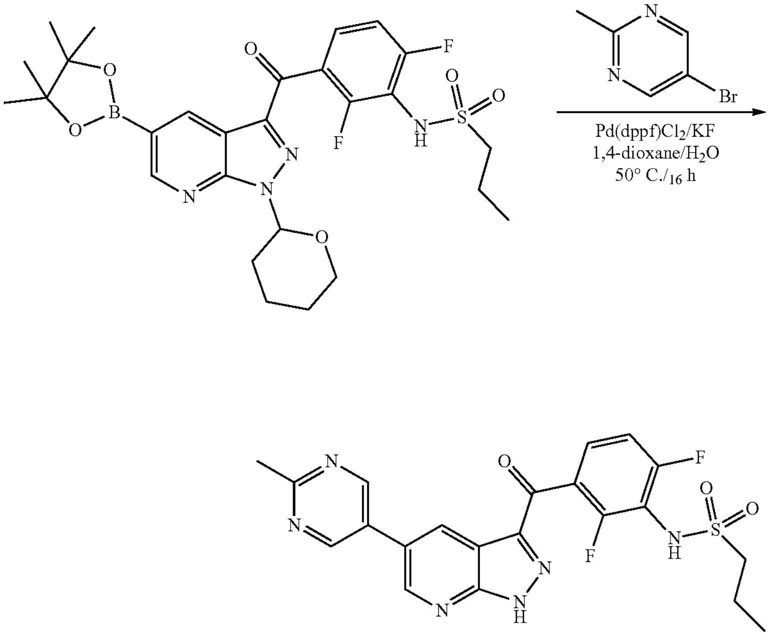

A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (120 mg, 0.203 mmol), 5-bromo-2-methylpyrimidine (38.7 mg, 0.224 mmol), potassium fluoride (35.4 mg, 0.610 mmol), $Pd(dppf)Cl_2$·DCM (3.32 mg, 0.00406 mmol) and degassed 1,4-dioxane/water (0.5 mL, (4+1)). The vessel was evacuated and filled with argon (3×) and heated to 60° C. for 2 h. The mixture was acidified with conc. HCl (0.3 mL), diluted with MeOH (0.2 mL) and heated to 60° C. O/N. Another 0.3 mL conc. HCl was added and stirring continued for 3 h. After cooling, the mixture was diluted with EtOAc and water. The organic phase was evaporated and the product was purified by flash chromatography.

Analytical Data:

$^1$H NMR (400 MHz, DMSO-$d_6$) δ 14.82 (s, 1H), 9.66 (s, 1H), 9.16 (s, 2H), 9.06 (d, J=2.1 Hz, 1H), 8.89 (d, J=2.2 Hz, 1H), 7.86 (dd, J=14.6, 7.6 Hz, 1H), 7.40 (t, J=8.7 Hz, 1H), 3.15 (dd, J=8.7, 6.5 Hz, 2H), 2.70 (s, 3H), 1.81 (dq, J=14.9, 7.4 Hz, 2H), 0.99 (t, J=7.5 Hz, 3H);

Calculated exact mass: 472.11 for $C_{21}H_{18}F_2N_6O_3S$ (molecular weight: 472.47);

MS(ESI$^-$): m/z: 471.0 $[M-1]^-$

Example 8: Synthesis of 5-(3-(2,4-difluoro-3-(propylsulfonamido)benzoyl)-1H-pyrazolo[3,4-b]pyridin-5-yl)pyrimidine-2-carboxylic acid

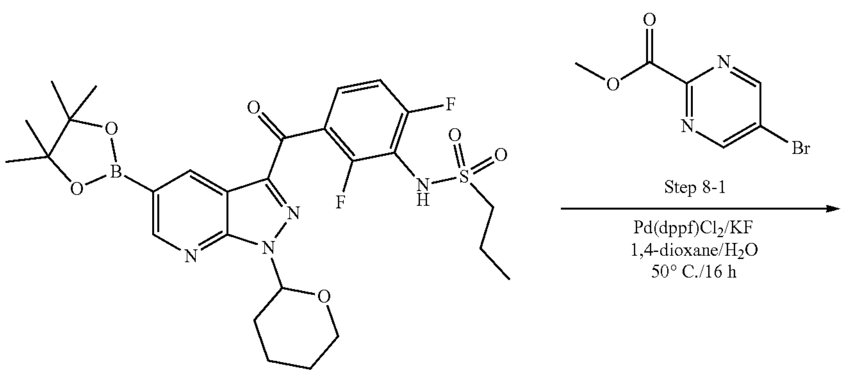

(I)

-continued

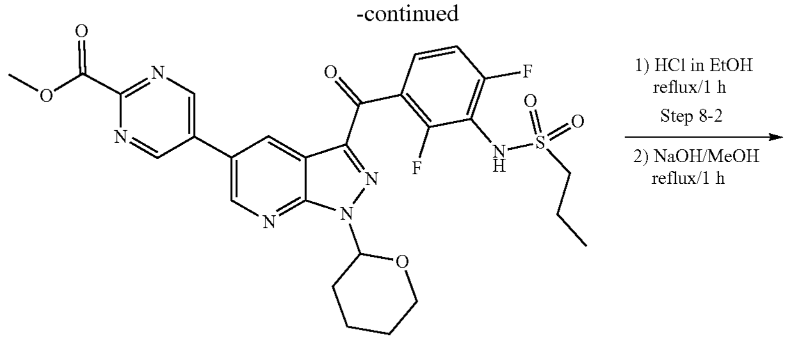

(II)

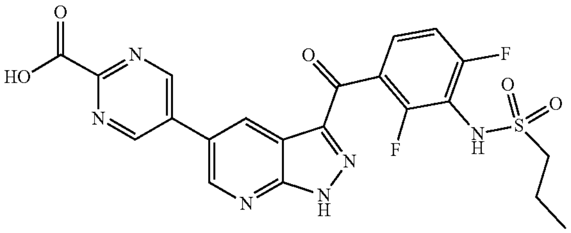

Example 8

Step 8-1: Methyl 5-(3-(2,4-difluoro-3-(propylsulfonamido)benzoyl)-1-(tetrahydro-2H-pyran-2-yl)-1H-pyrazolo[3,4-b]pyridin-5-yl)pyrimidine-2-carboxylate A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide ((I), 134 mg, 0.227 mmol), methyl 5-bromopyrimidine-2-carboxylate (54.2 mg, 0.250 mmol), potassium fluoride (39.6 mg, 0.681 mmol), Pd(dppf)$Cl_2$ DCM (3.71 mg, 0.00454 mmol) and degassed 1,4-dioxane/water (0.5 mL, (4+1)). The vessel was evacuated and filled with argon (3×) and heated to 60° C. for 2 h. $NH_4Cl$ solution and EtOAc were added and the mixture was evaporated over celite. The product was isolated by flash chromatography (DCM/EtOAc, 30% to 100%); 121 mg solid (0.2010 mmol, 89% yield).

Step 8-2: 5-(3-(2,4-difluoro-3-(propylsulfonamido)benzoyl)-1H-pyrazolo[3,4-b]pyridin-5-yl)pyrimidine-2-carboxylic acid Methyl 5-[3-[2,4-difluoro-3-(propylsulfonylamino)benzoyl]-1H-pyrazolo[3,4-b]pyridin-5-yl]pyrimidine-2-carboxylate ((II), 87.0 mg, 0.1640 mmol, 82% yield) was taken up 3 mL 2.5M HCl in EtOH and refluxed for 1 h. The solvent was removed in vacuo and the residue taken up in 2 mL MeOH and 2 mL 2N NaOH and refluxed for 1 h. After cooling, the mixture was acidified to pH 3 with 1N HCl, brine was added and the mixture was extracted with THF and THF/EtOAc (1:1). The extracts were washed with brine (acidified with some 1N HCl), dried over $Na_2SO_4$ and filtered. The solvent was removed to yield 5-[3-[2,4-difluoro-3-(propylsulfonylamino)benzoyl]-1H-pyrazolo[3,4-b]pyridin-5-yl]pyrimidine-2-carboxylic acid (87.0 mg, 0.1640 mmol, 82% yield).

Analytical Data:

$^1$H NMR (400 MHz, DMSO-$d_6$) δ 14.94 (s, 1H), 9.68 (d, J=4.6 Hz, 1H), 9.45 (s, 2H), 9.16 (d, J=1.7 Hz, 1H), 9.04 (s, 1H), 7.88 (dd, J=14.5, 7.9 Hz, 1H), 7.41 (t, J=8.9 Hz, 1H), 3.15 (dd, J=8.7, 6.6 Hz, 3H), 1.87-1.77 (m, 2H), 1.00 (t, J=7.5 Hz, 3H);

Calculated exact mass: 502.09 for $C_{21}H_{16}F_2N_6O_5S$ (molecular weight: 502.45);

MS(ESI$^-$): m/z: 501.0 [M−1]$^-$

Example 9: Synthesis of N-(3-(5-(2-cyanopyrimidin-5-yl)-1H-pyrazolo[3,4-b]pyridine-3-carbonyl)-2,6-difluorophenyl)propane-1-sulfonamide

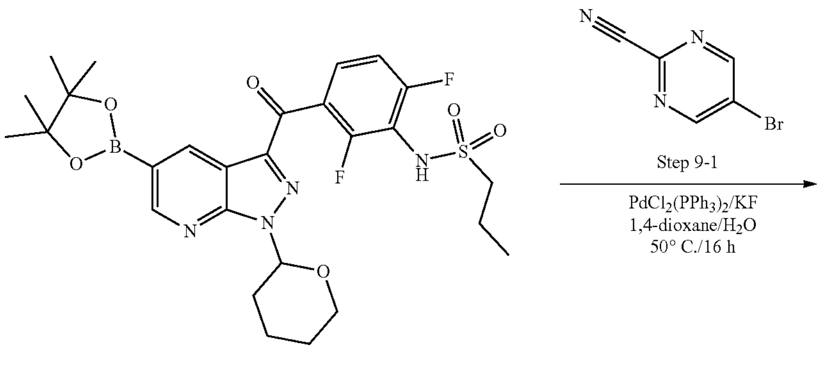

(I)

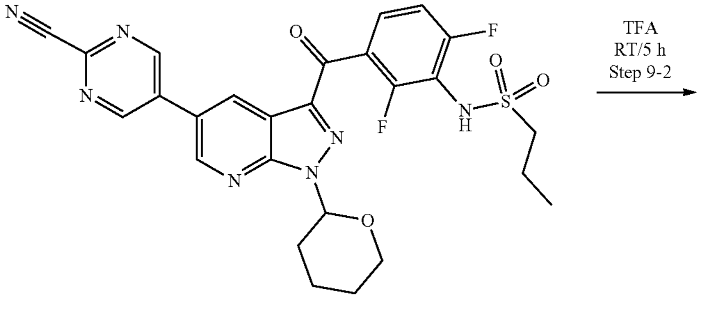

(II)

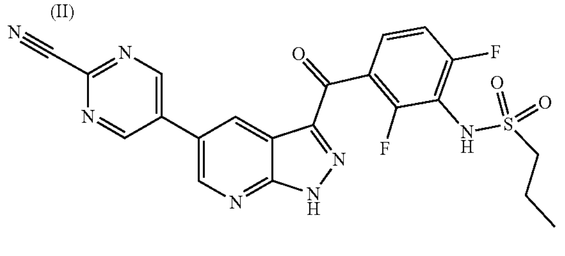

Example 9

Step 9-1: N-[3-[5-(2-cyanopyrimidin-5-yl)-1-(oxan-2-yl)pyrazolo[3,4-b]pyridine-3-carbonyl]-2,6-difluorophenyl]propane-1-sulfonamide A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide ((I), 398 mg, 0.674 mmol), 5-bromopyrimidine-2-carbonitrile (136 mg, 0.741 mmol), potassium fluoride (117 mg, 2.02 mmol), $PdCl_2(PPh_3)_2$ (11.8 mg, 0.0169 mmol) and degassed dioxane/water (4+1, 2.5 mL). The vessel was evacuated and filled with argon (3×) and heated to 60° C. for 2 h. After cooling, the reaction mixture was diluted with $NH_4Cl$ solution and extracted with EtOAc. The extract was washed with brine, dried over $Na_2SO_4$ and evaporated. The residue was purified by flash chromatography (DCM/EtOAc, 5% to 30%) to yield N-[3-[5-(2-cyanopyrimidin-5-yl)-1-(oxan-2-yl)pyrazolo[3,4-b]pyridine-3-carbonyl]-2,6-difluorophenyl]propane-1-sulfonamide (270 mg, 0.4760 mmol, 71% yield).

Step 9-2: N-[3-[5-(2-cyanopyrimidin-5-yl)-1H-pyrazolo[3,4-b]pyridine-3-carbonyl]-2,6-difluorophenyl]propane-1-sulfonamide N-[3-[5-(2-cyanopyrimidin-5-yl)-1-(oxan-2-yl)pyrazolo[3,4-b]pyridine-3-carbonyl]-2,6-difluorophenyl]propane-1-sulfonamide ((II), 50.0 mg, 0.0881 mmol) was stirred in 1 mL TFA at RT for 5 h. The mixture was concentrated, taken up in water and the pH was adjusted to 4 using 1N NaOH. The aqueous phase was extracted with EtOAc, the extract washed with brine, dried over $Na_2SO_4$ and evaporated. The residue was triturated with diethyl ether to yield N-[3-[5-(2-cyanopyrimidin-5-yl)-1H-pyrazolo[3,4-b]pyridine-3-carbonyl]-2,6-difluorophenyl]propane-1-sulfonamide (27.0 mg, 0.0542 mmol, 61% yield).

Analytical Data:

$^1$HNMR (400 MHz, DMSO-$d_6$) δ 14.98 (s, 1H), 9.68 (s, 1H), 9.55 (s, 2H), 9.31 (s, 1H), 9.17 (d, J=2.2 Hz, 1H), 9.08 (d, J=2.1 Hz, 1H), 7.88 (dd, J=14.5, 7.8 Hz, 1H), 7.41 (t, J=8.8 Hz, 1H), 3.19-3.10 (m, 2H), 1.86-1.74 (m, 2H), 1.00 (t, J=7.5 Hz, 3H);

Calculated exact mass: 483.09 for $C_{21}H_{15}F_2N_7O_3S$ (molecular weight: 483.45);

MS(ESI$^-$): m/z: 482.0 $[M-1]^-$.

Example 10: Synthesis of N-(3-(5-(2-(1H-tetrazol-5-yl)pyrimidin-5-yl)-1H-pyrazolo[3,4-b]pyridine-3-carbonyl)-2,6-difluorophenyl)propane-1-sulfonamide

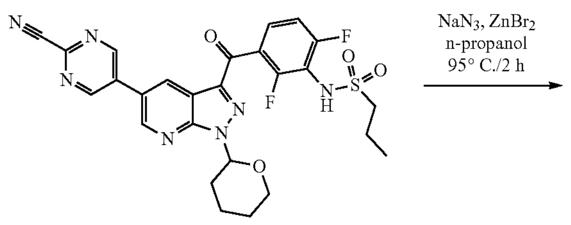

-continued

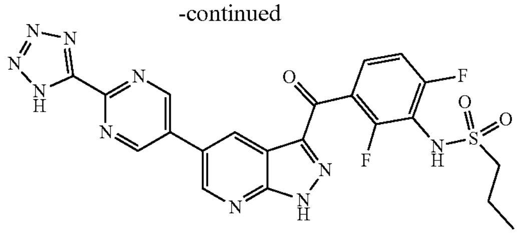

Modified from: Vorona, S., et al. (Synthesis-Stuttgart 46(6): 781-786 (2014)), N-[3-[5-(2-cyanopyrimidin-5-yl)-1-(oxan-2-yl)pyrazolo[3,4-b]pyridine-3-carbonyl]-2,6-difluorophenyl]-propane-1-sulfonamide (75.0 mg, 0.132 mmol), zinc bromide (29.8 mg, 0.132 mmol) and sodium azide (9.45 mg, 0.145 mmol) were heated to 95° C. in 1-propanol (0.661 mL) for 2 h. The reaction was cooled, 0.25 N NaOH (2.64 mL, 0.661 mmol) was added, n-propanol removed under reduced pressure and the suspension was stirred for 15 minutes at RT. The mixture was filtered and the filter washed with 0.25 N NaOH (2.64 mL, 0.661 mmol). The filtrate was acidified with 2N HCl and extracted with EtOAc. The extract was washed with brine, dried over $Na_2SO_4$ and evaporated. The residue was taken up in 2.5N HCl in EtOH (2 mL) and heated to 70° C. for 2 h. The reaction was concentrated, diluted with diethyl ether and the solids were collected by suction filtration to yield N-[2,6-difluoro-3-[5-[2-(1H-tetrazol-5-yl)pyrimidin-5-yl]-1H-pyrazolo[3,4-b]pyridine-3-carbonyl]phenyl]propane-1-sulfonamide hydrochloride (44.0 mg, 0.0782 mmol, 59% yield).

Analytical Data:

$^1$H NMR (400 MHz, DMSO-$d_6$) δ 14.96 (s, 1H), 9.68 (s, 1H), 9.57 (s, 2H), 9.22 (d, J=2.1 Hz, 1H), 9.08 (d, J=2.1 Hz, 1H), 7.88 (dd, J=14.8, 7.6 Hz, 1H), 7.41 (t, J=8.5 Hz, 1H), 3.21-3.09 (m, 2H), 1.89-1.72 (m, 2H), 1.00 (t, J=7.4 Hz, 3H); Calculated exact mass: 526.11 for $C_{21}H_{16}F_2N_{10}O_3S$ (molecular weight: 526.48);

MS(ESI−): m/z: 525.0 $[M-1]^-$.

Example 11: Synthesis of N-(3-(5-(2-cyclopropylpyrimidin-5-yl)-1H-pyrazolo[3,4-b]pyridine-3-carbonyl)-2,6-difluorophenyl)propane-1-sulfonamide

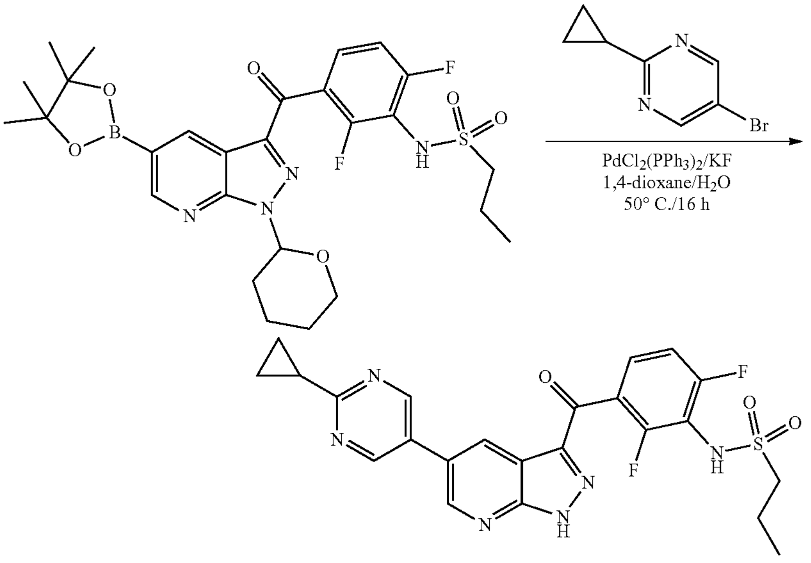

A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (176 mg, 0.298 mmol), 5-bromo-2-cyclopropylpyrimidine (65.3 mg, 0.328 mmol), potassium fluoride (52.0 mg, 0.894 mmol), $PdCl_2(PPh_3)_2$ (4.18 mg, 0.00596 mmol) and degassed 1,4-dioxane/water (1 mL, (4+1)). The vessel was evacuated and filled with argon (3×) and heated to 60° C. for 2 h. After cooling, the mixture was partitioned between sat. $NH_4Cl$ solution and EtOAc, the organic phase was dried over $Na_2SO_4$ and evaporated. The major product was isolated by flash chromatography (DCM/EtOAc, 20% to 80%) and taken up in 2 mL 2.5 N HCl in EtOH and refluxed for 2 h. The reaction mixture was concentrated and the solids triturated with EtOAc to yield N-[3-[5-(2-cyclopropylpyrimidin-5-yl)-1H-pyrazolo[3,4-b]pyridine-3-carbonyl]-2,6-difluorophenyl]propane-1-sulfonamide hydrochloride (55.0 mg, 0.1030 mmol, 34% yield).

Analytical Data:

$^1$H NMR (400 MHz, DMSO) δ 14.90 (s, 1H), 9.68 (s, 1H), 9.11 (s, 2H), 9.04 (d, J=2.2 Hz, 1H), 8.87 (d, J=2.2 Hz, 1H), 7.86 (dd, J=14.9, 7.6 Hz, 1H), 7.40 (t, J=8.5 Hz, 1H), 3.20-3.10 (m, 2H), 2.35-2.26 (m, 1H), 1.86-1.74 (m, 2H), 1.16-1.04 (m, 4H), 0.99 (t, J=7.5 Hz, 3H);

Calculated exact mass: 498.13; for $C_{23}H_{20}F_2N_6O_3S$ (molecular weight: 498.51);

MS($ESI^-$): m/z: 497.0 $[M-1]^-$.

Example 12: Synthesis of N-(3-(5-(2-chloropyrimidin-5-yl)-1H-pyrazolo[3,4-b]pyridine-3-carbonyl)-2,6-difluorophenyl)propane-1-sulfonamide

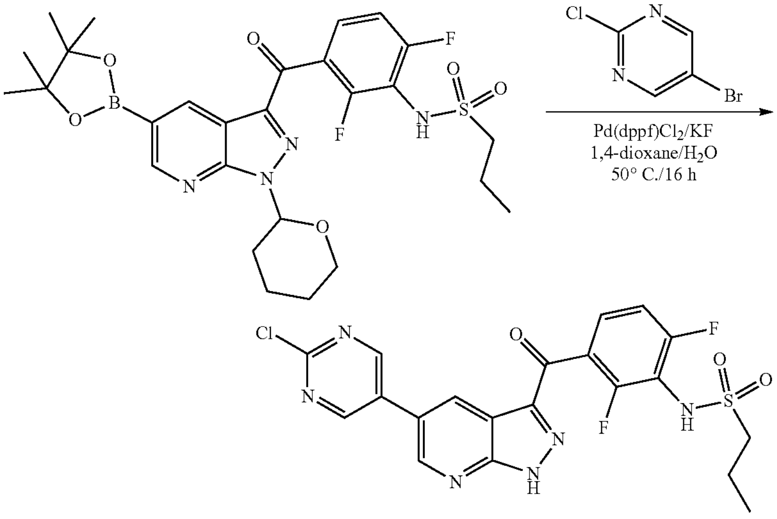

A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (120 mg, 0.203 mmol), 5-bromo-2-chloropyrimidine (43.2 mg, 0.224 mmol), potassium fluoride (35.4 mg, 0.610 mmol), Pd(dppf)$Cl_2$ DCM (3.32 mg, 0.00406 mmol) and degassed 1,4-dioxane/water (0.5 mL, (4+1)). The vessel was evacuated and filled with argon (3×) and heated to 60° C. for 2 h. After cooling, the mixture was partitioned between sat. $NH_4Cl$ solution and EtOAc, the organic phase was dried over $Na_2SO_4$ and evaporated. The residue was taken up in 1 mL DCM and 1 mL TFA and stirred O/N. The mixture was poured into water, extracted with EtOAc and the extract was washed with $NH_4Cl$ solution, dried over $Na_2SO_4$ and evaporated. The product was purified by flash chromatography (solvent: MeOH; with DCM/EtOAc, 20% to 80% as solvent system, the product did not elute from the column). Fractions containing product were evaporated to dryness and the residue triturated with toluene and MeOH. HPLC revealed only 87% purity. The solids were washed with DCM, MeCN and diethyl ether and dried (33.0 mg, 0.0596 mmol, 29% yield).

Analytical Data:

$^1$H NMR (400 MHz, DMSO-$d_6$) δ 14.92 (s, 1H), 9.67 (s, 1H), 9.28 (s, 2H), 9.09 (d, J=2.1 Hz, 1H), 8.98 (d, J=2.2 Hz, 1H), 7.87 (dd, J=14.9, 7.6 Hz, 1H), 7.40 (t, J=8.7 Hz, 1H), 3.22-3.10 (m, 2H), 1.86-1.74 (m, 2H), 1.00 (t, J=7.5 Hz, 3H);

Calculated exact mass: 492.06 for $C_{20}H_{15}ClF_2N_6O_3S$ (molecular weight: 492.89);

MS(ESI$^-$): m/z: 490.9 $[M-1]^-$.

Example 13: Synthesis of N-(3-(5-(4-chlorophenyl)-1H-pyrazolo[3,4-b]pyridine-3-carbonyl)-2,4,6-trifluorophenyl)propane-1-sulfonamide

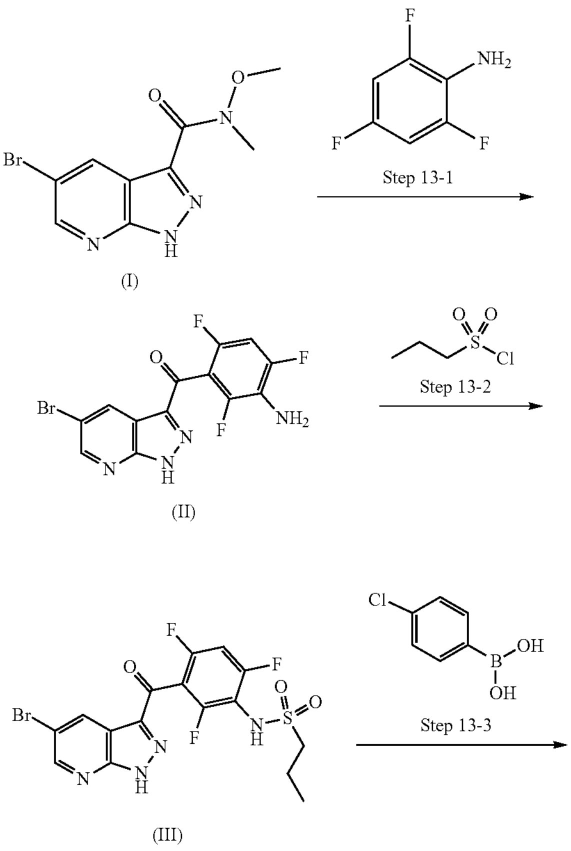

-continued

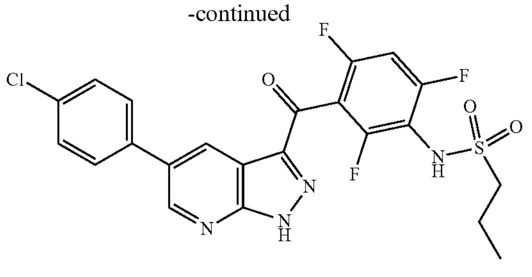

Example 13

Step 13-1: (3-amino-2,4,6-trifluorophenyl)-(5-bromo-1H-pyrazolo[3,4-b]pyridin-3-yl)methanone A solution of 2,4,6-trifluoroaniline (941 mg, 6.40 mmol) and chlorotrimethylsilane (1.62 mL, 12.8 mmol) in THF (5.82 mL) was cooled to −78° C. and 2M lithium diisopropylamide (6.40 mL, 12.8 mmol) in THF/heptane/ethylbenzene was added dropwise. The mixture was warmed to RT and stirred for 30 minutes. 5-bromo-N-methoxy-N-methyl-1H-pyrazolo[3,4-b]pyridine-3-carboxamide (829 mg, 2.91 mmol) was added and the mixture cooled to −30° C. Lithium diisopropylamide (4.65 mL, 9.30 mmol) in THF/heptane/ethylbenzene was added dropwise and the mixture was stirred at −15° C. for 20 minutes. Conc. HCl (3 mL) was added and the mixture was stirred for 10 minutes at RT. The reaction was neutralized with 2N NaOH, the aqueous phase was separated and extracted with THF. The combined organic phases were dried over $Na_2SO_4$, filtered and concentrated. The residue was purified by flash chromatography (DCM/EtOAc, 0%-25%) and triturated with a small amount of DCM to yield (3-amino-2,4,6-trifluorophenyl)-(5-bromo-1H-pyrazolo[3,4-b]pyridin-3-yl)methanone (0.423 g, 1.14 mmol, 39% yield) as bright yellow solid.

Analytical Data:

$^1$H-NMR (200 MHz, $CDCl_3$) δ 14.96 (s, 1H), 8.77 (d, J=2.8 Hz, 3H), 7.21 (t, J=10 Hz, 2H), 5.33 (s, 4H).

MS(ESI$^+$): m/z=370.8/368.8 [M−H]$^-$, 350.8/348.8 [M−H−HF]$^-$.

Step 13-2: N-[3-(5-bromo-1H-pyrazolo[3,4-b]pyridine-3-carbonyl)-2,4,6-trifluorophenyl] propane-1-sulfonamide To a solution of (3-amino-2,4,6-trifluorophenyl)-(5-bromo-1H-pyrazolo[3,4-b]pyridin-3-yl)methanone (0.378 g, 1.02 mmol) and TEA (1.56 mL, 11.2 mmol) in THF (5.09 mL) was added 1-propanesulfonyl chloride (0.378 mL, 3.36 mmol) in 1 mL THF slowly at −10° C. The reaction was stirred at 0° C. for 30 minutes and 2N NaOH (4.07 mL, 8.15 mmol) was added. After stirring at RT for 10 minutes, THF was evaporated from the mixture and the aqueous solution was washed with EtOAc. The solution was acidified with 2N HCl and extracted with EtOAc. The extract was dried over $Na_2SO_4$, evaporated and the residue was triturated with n-hexane to yield N-[3-(5-bromo-1H-pyrazolo[3,4-b]pyridine-3-carbonyl)-2,4,6-trifluorophenyl]propane-1-sulfonamide (0.344 g, 0.7210 mmol, 71% yield).

Analytical Data:

$^1$H NMR (200 MHz, DMSO-$d_6$) δ 8.78 (dd, J=5.7, 2.2 Hz, 2H), 7.57 (td, J=9.8, 2.0 Hz, 1H), 3.18-3.05 (m, 3H), 1.90-1.68 (m, 2H), 0.98 (t, J=7.4 Hz, 3H);

MS(ESI$^-$): 476.8/474.8 [M−H]$^-$, 456.9/454.9 [M−H−HF]$^-$.

Step 13-3: N-[3-[5-(4-chlorophenyl)-1H-pyrazolo[3,4-b]pyridine-3-carbonyl]-2,4,6-trifluorophenyl]propane-1-sulfonamide A microwave vessel was charged with N-[3-(5-bromo-1H-pyrazolo[3,4-b]pyridine-3-carbonyl)-2,4,6-trifluorophenyl]propane-1-sulfonamide (78.0 mg, 0.163 mmol), (4-chlorophenyl)boronic acid (26.8 mg, 0.172 mmol) and purged with argon. Degassed 1,4-dioxane (0.545 mL) and degassed 1.5 M aqueous potassium carbonate (0.327 mL, 0.490 mmol) were added and the reaction was heated to 110° C. under microwave irradiation for 1 h. The reaction was partitioned between $NH_4Cl$ solution and EtOAc and the organic phase was evaporated. The residue was purified by flash chromatography (DCM/EtOAc 5% to 35%) and triturated with a mixture of DCM and n-hexane to yield N-[3-[5-(4-chlorophenyl)-1H-pyrazolo[3,4-b]pyridine-3-carbonyl]-2,4,6-trifluorophenyl]propane-1-sulfonamide (44.0 mg, 0.0865 mmol, 53% yield).

Analytical Data:

$^1$H NMR (400 MHz, DMSO-$d_6$) δ 14.97 (s, 1H), 9.66 (s, 1H), 9.04 (d, J=2.2 Hz, 1H), 8.77 (d, J=2.2 Hz, 1H), 8.05-7.69 (m, 2H), 7.71-7.44 (m, 3H), 3.21-3.02 (m, 2H), 1.92-1.62 (m, 2H), 0.99 (t, J=7.4 Hz, 3H);

Calculated exact mass: 508.06 for $C_{22}H_{16}ClF_3N_4O_3S$ (molecular weight: 508.90);

MS(ESI$^-$): m/z: 507.0 [M−1]$^-$.

Example 14: Synthesis of N-(3-(5-(2-cyclopropylpyrimidin-5-yl)-1H-pyrazolo[3,4-b]pyridine-3-carbonyl)-2,6-difluorophenyl)-1-phenylmethanesulfonamide Example 14 was synthesized in analogy to Example 11.

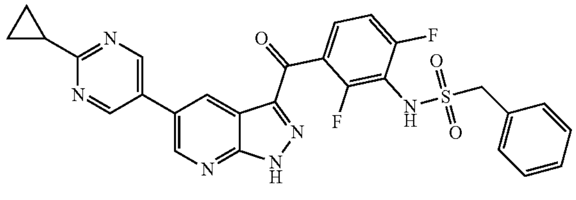 [SMILES: O=C(c1ccc(F)c(NS(=O)(=O)Cc2ccccc2)c1F)c1n[nH]c2ncc(-c3cnc(C4CC4)nc3)cc12]

Analytical Data:

$^1$H NMR (400 MHz, dmso) δ 15.02-14.46 (m, 1H), 9.77 (s, 1H), 9.10 (s, 2H), 9.05 (d, J=2.1 Hz, 1H), 8.88 (d, J=2.1 Hz, 1H), 7.86 (dd, J=14.3, 7.5 Hz, 1H), 7.46-7.34 (m, 6H), 4.51 (s, 2H), 2.35-2.24 (m, 1H), 1.15-1.06 (m, 4H).

Calculated exact mass: 546.13 for $C_{27}H_{20}F_2N_6O_3S$ (molecular weight: 546.55)

MS(ESI$^+$): m/z 546.0 [M+H]$^+$.

Example 15: Synthesis of N-(2,6-difluoro-3-(5-(2-methoxypyrimidin-5-yl)-1H-pyrazolo[3,4-b]pyridine-3-carbonyl)phenyl)propane-1-sulfonamide Example 15 was synthesized in analogy to Example 7.

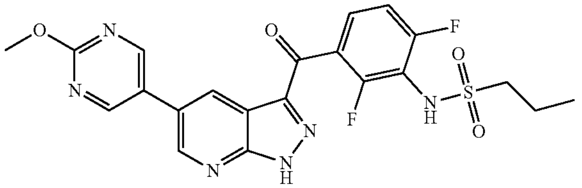 [SMILES: CCCS(=O)(=O)Nc1c(F)ccc(C(=O)c2n[nH]c3ncc(-c4cnc(OC)nc4)cc23)c1F]

Analytical Data:

$^1$H NMR (400 MHz, DMSO-$d_6$) δ 14.87 (s, 1H), 9.67 (s, 1H), 9.09 (s, 2H), 9.04 (d, J=1.7 Hz, 1H), 8.86 (d, J=1.6 Hz, 1H), 7.86 (dd, J=14.3, 7.6 Hz, 1H), 7.40 (t, J=8.8 Hz, 1H), 4.00 (s, 3H), 3.19-3.09 (m, 2H), 1.81 (td, J=14.8, 7.3 Hz, 2H), 0.99 (t, J=7.3 Hz, 3H).

Calculated exact mass: 488.11 for $C_{21}H_{18}F_2N_6O_4S$ (molecular weight: 488.47)

MS($ESI^+$): m/z 489.05 $[M+H]^+$.

Example 16: Synthesis of N-(2,6-difluoro-3-(5-(2-hydroxypyrimidin-5-yl)-1H-pyrazolo[3,4-b]pyridine-3-carbonyl)phenyl)propane-1-sulfonamide Example 16 was synthesized in analogy to Example 7.

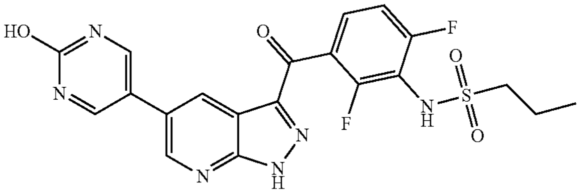 [SMILES: CCCS(=O)(=O)Nc1c(F)ccc(C(=O)c2n[nH]c3ncc(-c4cnc(O)nc4)cc23)c1F]

Analytical Data:

$^1$H NMR (400 MHz, DMSO-$d_6$) δ 14.78 (s, 1H), 12.38 (s, 1H), 9.66 (s, 1H), 8.95 (s, 1H), 8.77 (s, 1H), 8.49 (s, 2H), 7.85 (dd, J=14.7, 7.7 Hz, 1H), 7.39 (t, J=9.0 Hz, 1H), 3.18-3.11 (m, 2H), 1.81 (td, J=14.8, 7.3 Hz, 2H), 1.00 (t, J=7.4 Hz, 3H).

Calculated exact mass: 474.09 for $C_{20}H_{16}F_2N_6O_4S$ (molecular weight: 474.44)

MS($ESI^+$): m/z 475.00 $[M+H]^+$.

Example 17: Synthesis of N-(3-(5-(3-chloropyridin-4-yl)-1H-pyrazolo[3,4-b]pyridine-3-carbonyl)-2,6-difluorophenyl)propane-1-sulfonamide Example 17 was synthesized in analogy to Example 7.

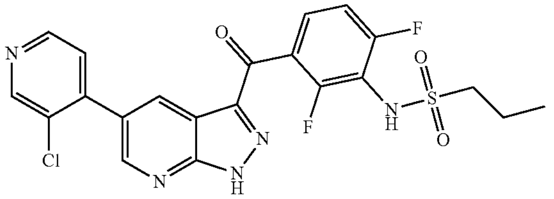

Analytical Data:

$^1$H NMR (400 MHz, DMSO-$d_6$) δ 15.05-14.58 (m, 1H), 9.66 (s, 1H), 8.83 (s, 2H), 8.76 (d, J=1.6 Hz, 1H), 8.68 (d, J=4.8 Hz, 1H), 7.87 (dd, J=14.3, 8.0 Hz, 1H), 7.70 (d, J=4.9 Hz, 1H), 7.40 (t, J=8.9 Hz, 1H), 3.19-3.10 (m, 2H), 1.81 (dq, J=14.8, 7.3 Hz, 2H), 1.00 (t, J=7.4 Hz, 3H).

Calculated exact mass: 491.06 for $C_{21}H_{16}ClF_2N_5O_3S$ (molecular weight: 491.90)

MS($ESI^+$): m/z 491.95 $[M+H]^+$.

Example 18: Synthesis of N-(2,6-difluoro-3-(5-(3-methylpyridin-4-yl)-1H-pyrazolo[3,4-b]pyridine-3-carbonyl)phenyl)propane-1-sulfonamide Example 18 was synthesized in analogy to Example 7.

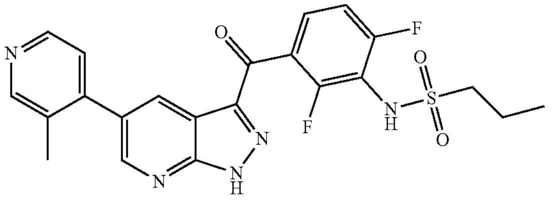 [SMILES: CCCS(=O)(=O)Nc1c(F)ccc(C(=O)c2n[nH]c3ncc(-c4ccncc4C)cc23)c1F]

Analytical Data:

$^1$H NMR (400 MHz, DMSO-$d_6$) δ 14.82 (s, 1H), 9.88-9.37 (m, 1H), 8.75 (d, J=1.9 Hz, 1H), 8.56 (d, J=1.6 Hz, 1H), 8.55 (d, J=0.9 Hz, 1H), 7.85 (dd, J=14.7, 7.5 Hz, 1H), 7.78 (d, J=7.6 Hz, 1H), 7.39 (dd, J=10.8, 5.9 Hz, 2H), 3.17-3.11 (m, 2H), 2.48 (s, 3H), 1.81 (dq, J=14.9, 7.4 Hz, 2H), 1.00 (t, J=7.4 Hz, 3H).

Calculated exact mass: 471.12 for $C_{22}H_{19}F_2N_5O_3S$ (molecular weight: 471.48)

MS($ESI^+$): m/z 471.9 $[M+H]^+$.

Example 19: Synthesis of N-(3-(5-(4-(tert-butyl)phenyl)-1H-pyrazolo[3,4-b]pyridine-3-carbonyl)-2,6-difluorophenyl)propane-1-sulfonamide Example 19 was synthesized in analogy to Example 7.

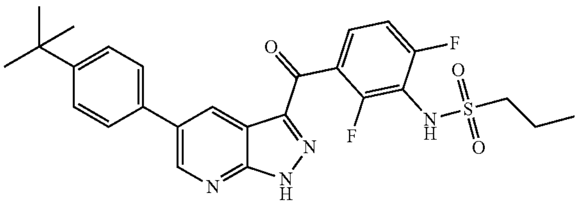 [SMILES: CCCS(=O)(=O)Nc1c(F)ccc(C(=O)c2n[nH]c3ncc(-c4ccc(C(C)(C)C)cc4)cc23)c1F]

Analytical Data:

$^1$H NMR (400 MHz, DMSO-$d_6$) δ 14.78 (s, 1H), 9.67 (s, 1H), 9.00 (d, J=2.1 Hz, 1H), 8.73 (d, J=2.1 Hz, 1H), 7.86 (dd, J=14.7, 7.6 Hz, 1H), 7.75 (d, J=8.3 Hz, 2H), 7.57 (d, J=8.4 Hz, 2H), 7.40 (t, J=8.8 Hz, 1H), 3.18-3.12 (m, 2H), 1.81 (td, J=15.0, 7.4 Hz, 2H), 1.34 (s, 9H), 1.00 (t, J=7.4 Hz, 3H).

Calculated exact mass: 512.17 for $C_{26}H_{26}F_2N_4O_3S$ (molecular weight: 512.56)

MS($ESI^+$): m/z 513.0 $[M+H]^+$.

Example 20: Synthesis of N-(3-(5-(2-chloro-4-methoxyphenyl)-1H-pyrazolo[3,4-b]pyridine-3-carbonyl)-2,6-difluorophenyl)propane-1-sulfonamide Example 20 was synthesized in analogy to Example 7.

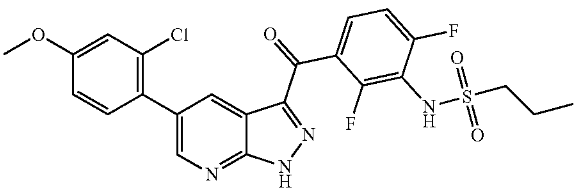 [SMILES: CCCS(=O)(=O)Nc1c(F)ccc(C(=O)c2n[nH]c3ncc(-c4ccc(OC)cc4Cl)cc23)c1F]

Analytical Data:

$^1$H NMR (400 MHz, DMSO-$d_6$) δ 14.82 (s, 1H), 9.66 (s, 1H), 8.72 (d, J=1.8 Hz, 1H), 8.57 (d, J=1.8 Hz, 1H), 7.86 (dd, J=15.0, 7.4 Hz, 1H), 7.53 (d, J=8.6 Hz, 1H), 7.39 (t, J=8.7 Hz, 1H), 7.25 (d, J=2.3 Hz, 1H), 7.10 (dd, J=8.6, 2.4 Hz, 1H), 3.86 (s, 3H), 3.15 (t, J=7.6 Hz, 2H), 1.81 (dq, J=15.0, 7.5 Hz, 2H), 1.00 (t, J=7.4 Hz, 3H).

Calculated exact mass: 520.08 for $C_{23}H_{19}ClF_2N_4O_4S$ (molecular weight: 520.94)

MS(ESI$^+$): m/z 521.0 [M+H]$^+$.

Example 21: Synthesis of N-(3-(5-(2-(tert-butyl)pyrimidin-5-yl)-1H-pyrazolo[3,4-b]pyridine-3-carbonyl)-2,6-difluorophenyl)propane-1-sulfonamide Example 21 was synthesized in analogy to Example 7.

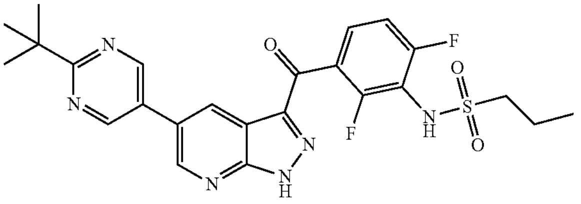 [SMILES: CCCS(=O)(=O)Nc1c(F)ccc(C(=O)c2n[nH]c3ncc(-c4cnc(C(C)(C)C)nc4)cc23)c1F]

Analytical Data:

$^1$H NMR (400 MHz, DMSO-$d_6$) δ 14.88 (s, 1H), 9.66 (s, 1H), 9.22 (s, 2H), 9.08 (s, 1H), 8.91 (s, 1H), 7.86 (dd, J=14.7, 7.3 Hz, 1H), 7.40 (t, J=8.7 Hz, 1H), 3.18-3.11 (m, 2H), 1.87-1.74 (m, 2H), 1.43 (s, 9H), 1.00 (t, J=7.2 Hz, 3H).

Calculated exact mass: 514.16 for $C_{24}H_{24}F_2N_6O_3S$ (molecular weight: 514.55)

MS(ESI$^+$): m/z 515.15 [M+H]$^+$.

Example 22: Synthesis of N-(2,6-difluoro-3-(5-(2-(methylthio)pyrimidin-5-yl)-1H-pyrazolo[3,4-b]pyridine-3-carbonyl)phenyl)propane-1-sulfonamide Example 22 was synthesized in analogy to Example 7.

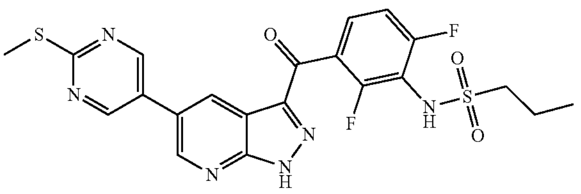

Analytical Data:

$^1$H NMR (400 MHz, DMSO-$d_6$) δ 14.87 (s, 1H), 9.67 (s, 1H), 9.13 (s, 2H), 9.06 (d, J=1.9 Hz, 1H), 8.90 (d, J=1.9 Hz, 1H), 7.86 (dd, J=14.3, 7.5 Hz, 1H), 7.40 (t, J=8.8 Hz, 1H), 3.19-3.12 (m, 2H), 2.60 (s, 3H), 1.87-1.75 (m, 2H), 1.00 (t, J=7.4 Hz, 3H).

Calculated exact mass: 504.08 for $C_{21}H_{18}F_2N_6O_3S_2$ (molecular weight: 504.53)

MS(ESI$^+$): m/z 505.05 [M+H]$^+$.

Example 23: Synthesis of N-(2,6-difluoro-3-(5-(2-isopropylpyrimidin-5-yl)-1H-pyrazolo[3,4-b]pyridine-3-carbonyl)phenyl)propane-1-sulfonamide Example 23 was synthesized in analogy to Example 7.

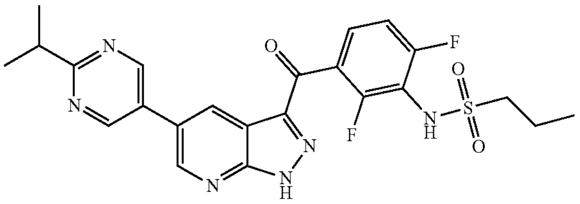 [SMILES: CCCS(=O)(=O)Nc1c(F)ccc(C(=O)c2n[nH]c3ncc(-c4cnc(C(C)C)nc4)cc23)c1F]

Analytical Data:

$^1$H NMR (400 MHz, DMSO-$d_6$) δ 14.87 (s, 1H), 9.67 (s, 1H), 9.13 (s, 2H), 9.06 (d, J=1.9 Hz, 1H), 8.90 (d, J=1.9 Hz, 1H), 7.86 (dd, J=14.3, 7.5 Hz, 1H), 7.40 (t, J=8.8 Hz, 1H), 3.19-3.12 (m, 2H), 2.60 (s, 3H), 1.87-1.75 (m, 2H), 1.00 (t, J=7.4 Hz, 3H).

Calculated exact mass: 500.14 for $C_{23}H_{22}F_2N_6O_3S$ (molecular weight: 500.52)

MS(ESI$^+$): m/z 501.05 [M+H]$^+$.

Example 24: Synthesis of N-(2,6-difluoro-3-(5-(4-fluoro-2-methylphenyl)-1H-pyrazolo[3,4-b]pyridine-3-carbonyl)phenyl)propane-1-sulfonamide Example 24 was synthesized in analogy to Example 7.

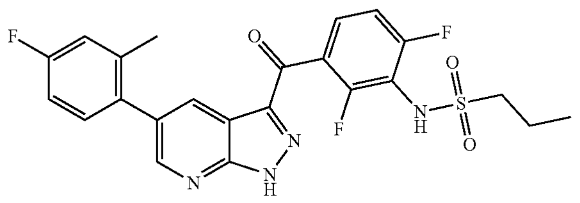 [SMILES: CCCS(=O)(=O)Nc1c(F)ccc(C(=O)c2n[nH]c3ncc(-c4ccc(F)cc4C)cc23)c1F]

Analytical Data:

$^1$H NMR (400 MHz, DMSO-$d_6$) δ 14.82 (s, 1H), 9.67 (s, 1H), 8.68 (d, J=2.1 Hz, 1H), 8.48 (d, J=2.1 Hz, 1H), 7.86 (dd, J=14.8, 7.6 Hz, 1H), 7.42-7.36 (m, 2H), 7.26 (dd, J=10.1, 2.5 Hz, 1H), 7.17 (td, J=8.5, 2.6 Hz, 1H), 3.18-3.11 (m, 2H), 2.28 (s, 3H), 1.81 (dq, J=15.0, 7.4 Hz, 2H), 1.00 (t, J=7.4 Hz, 3H).

Calculated exact mass: 488.11 for $C_{23}H_{19}F_3N_4O_3S$ (molecular weight: 488.49)

MS(ESI$^+$): m/z 489.05 [M+H]$^+$.

Example 25 and 26: Synthesis of N-(2,6-difluoro-3-(5-(4-methoxy-2-methylpyrimidin-5-yl)-1H-pyrazolo[3,4-b]pyridine-3-carbonyl)phenyl)propane-1-sulfonamide (Example 25) and N-(2,6-difluoro-3-(5-(4-hydroxy-2-methylpyrimidin-5-yl)-1H-pyrazolo[3,4-b]pyridine-3-carbonyl)phenyl)propane-1-sulfonamide (Example 26)

Step 1: The Conversion of N-(2,6-difluoro-3-(1-(tetrahydro-2H-pyran-2-yl)-5-(4,4,5,5-tetramethyl-1,3,2-dioxaborolan-2-yl)-1H-pyrazolo[3,4-b]pyridine-3-carbonyl)phenyl)propane-1-sulfonamide with 5-bromo-4-chloro-2-methylpyrimidine was Performed in Analogy to Example 9, Step 9-1

Two different procedures for deprotection led either to Example 25 or Example 26.

Analytical Data of N-(2,6-difluoro-3-(5-(4-methoxy-2-methylpyrimidin-5-yl)-1H-pyrazolo[3,4-b]pyridine-3-carbonyl)phenyl)propane-1-sulfonamide $^1$H NMR (400 MHz, DMSO-d$_6$) δ 14.84 (s, 1H), 9.66 (s, 1H), 8.86 (d, J=2.0 Hz, 1H), 8.75 (d, J=2.0 Hz, 1H), 8.64 (s, 1H), 7.85 (dd, J=15.4, 7.4 Hz, 1H), 7.39 (t, J=8.7 Hz, 1H), 3.99 (s, 3H), 3.18-3.10 (m, 2H), 2.62 (s, 3H), 1.81 (td, J=15.3, 7.7 Hz, 2H), 1.00 (t, J=7.5 Hz, 3H).

Calculated exact mass: 502.12 for $C_{22}H_{20}F_2N_6O_4S$ (molecular weight: 502.50)

MS(ESI$^+$): m/z 502.95 [M+H]$^+$.

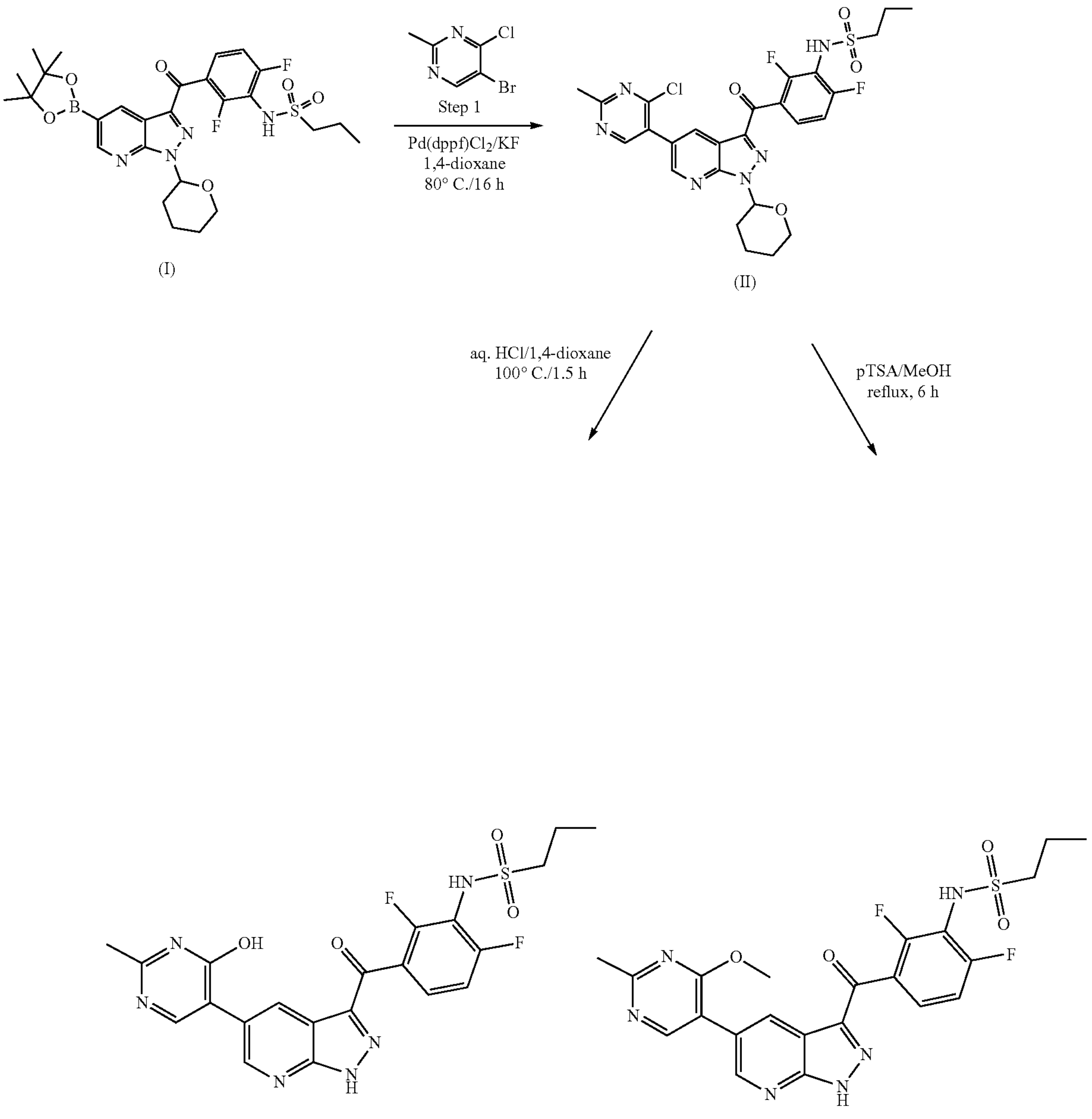

(I)

(II)

Example 26

Example 25

Analytical Data of N-(2,6-difluoro-3-(5-(4-hydroxy-2-methylpyrimidin-5-yl)-1H-pyrazolo[3,4-b]pyridine-3-carbonyl)phenyl)propane-1-sulfonamide $^1H$ NMR (400 MHz, DMSO-$d_6$) δ 14.84 (s, 1H), 9.66 (s, 1H), 8.86 (d, J=2.0 Hz, 1H), 8.75 (d, J=2.0 Hz, 1H), 8.64 (s, 1H), 7.85 (dd, J=15.4, 7.4 Hz, 1H), 7.39 (t, J=8.7 Hz, 1H), 3.99 (s, 3H), 3.18-3.10 (m, 2H), 2.62 (s, 3H), 1.81 (td, J=15.3, 7.7 Hz, 2H), 1.00 (t, J=7.5 Hz, 3H).

Calculated exact mass: 488.11 for $C_{21}H_{18}F_2N_6O_4S$ (molecular weight: 488.47)

MS(ESI$^+$): m/z 489.15 [M+H]$^+$.

Example 27: Synthesis of N-(2,6-difluoro-3-(5-(pyridin-3-yl)-1H-pyrazolo[3,4-b]pyridine-3-carbonyl)phenyl)propane-1-sulfonamide Example 27 was synthesized in analogy to Example 11.

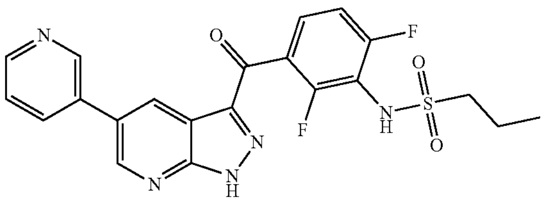 [SMILES: CCCS(=O)(=O)Nc1c(F)ccc(C(=O)c2n[nH]c3ncc(-c4cccnc4)cc23)c1F]

Analytical Data:

$^1H$ NMR (400 MHz, DMSO-$d_6$) δ 14.86 (s, 1H), 9.67 (s, 1H), 9.05 (dd, J=10.7, 2.0 Hz, 2H), 8.83 (d, J=2.2 Hz, 1H), 8.66 (dd, J=4.8, 1.5 Hz, 1H), 8.30-8.23 (m, 1H), 7.87 (dd, J=14.9, 7.5 Hz, 1H), 7.57 (dd, J=7.5, 4.8 Hz, 1H), 7.40 (t, J=8.5 Hz, 1H), 3.17-3.12 (m, 2H), 1.86-1.75 (m, 2H), 1.00 (t, J=7.5 Hz, 3H);

Calculated exact mass: 457.10 for $C_{21}H_{17}F_2N_5O_3S$ (molecular weight: 457.46)

MS(ESI$^-$): m/z: 455.9 [M−1]$^-$.

Example 28: Synthesis of 5-(3-(2,4-difluoro-3-(propylsulfonamido)benzoyl)-1H-pyrazolo[3,4-b]pyridin-5-yl)picolinic acid Example 28 was synthesized in analogy to Example 11.

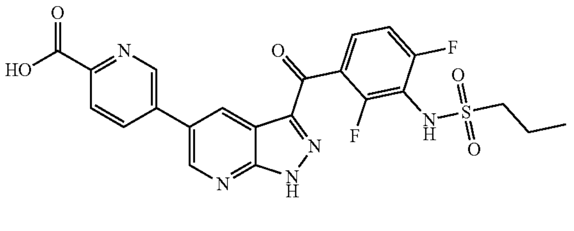 [SMILES: CCCS(=O)(=O)Nc1c(F)ccc(C(=O)c2n[nH]c3ncc(-c4ccc(C(=O)O)nc4)cc23)c1F]

Analytical Data:

$^1H$ NMR (400 MHz, DMSO-$d_6$) δ 14.92 (s, 1H), 9.68 (s, 1H), 9.15 (dd, J=16.8, 2.0 Hz, 2H), 8.93 (d, J=2.0 Hz, 1H), 8.45 (dd, J=8.1, 2.3 Hz, 1H), 8.18 (d, J=8.1 Hz, 1H), 7.88 (dd, J=14.5, 7.7 Hz, 1H), 7.41 (t, J=8.7 Hz, 1H), 3.19-3.10 (m, 2H), 1.86-1.75 (m, 2H), 1.00 (t, J=7.5 Hz, 3H);

Calculated exact mass: 501.09 for $C_{22}H_{17}F_2N_5O_5S$ (molecular weight: 501.46);

MS(ESI$^-$): m/z: 500.1 [M−1]$^-$

Example 29: Synthesis of N-[2,6-difluoro-3-[5-(4-methylpyrimidin-5-yl)-1H-pyrazolo[3,4-b]pyridine-3-carbonyl]phenyl]propane-1-sulfonamide Example 29 was synthesized in analogy to Example 7.

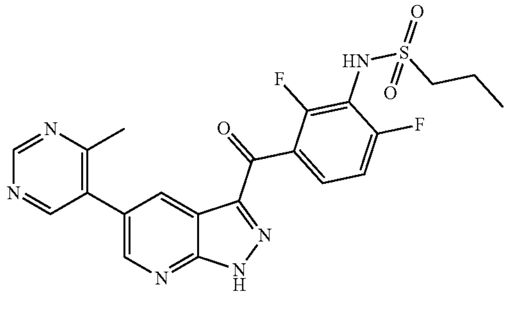 [SMILES: CCCS(=O)(=O)Nc1c(F)ccc(C(=O)c2n[nH]c3ncc(-c4cncnc4C)cc23)c1F]

Analytical Data:

$^1H$ NMR (400 MHz, DMSO-$d_6$) δ 14.90 (s, 1H), 9.66 (s, 1H), 9.12 (s, 1H), 8.80 (d, J=2.1 Hz, 1H), 8.76 (s, 1H), 8.68 (d, J=2.1 Hz, 1H), 7.90-7.82 (m, 1H), 7.43-7.36 (m, 1H), 3.30 (s, 3H), 3.19-3.11 (m, 3H), 1.88-1.73 (m, 3H), 1.00 (t, J=7.4 Hz, 3H).;

Calculated exact mass: 472.11 for $C_{21}H_{18}F_2N_6O_3S$ (molecular weight: 472.47);

MS(ESI$^+$): m/z: 473.55 [M+H]$^+$.

Example 30: Synthesis of N-[3-[5-(2,4-dimethylpyrimidin-5-yl)-1H-pyrazolo[3,4-b]pyridine-3-carbonyl]-2,6-difluoro-phenyl]propane-1-sulfonamide Example 30 was synthesized in analogy to Example 7.

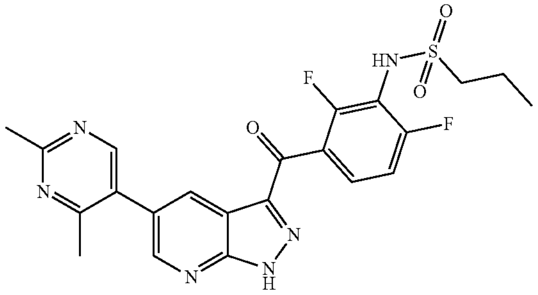 [SMILES: CCCS(=O)(=O)Nc1c(F)ccc(C(=O)c2n[nH]c3ncc(-c4cnc(C)nc4C)cc23)c1F]

Analytical Data:

$^1H$ NMR (400 MHz, DMSO-$d_6$) δ 14.88 (s, 1H), 9.67 (s, 1H), 8.77 (d, J=1.6 Hz, 1H), 8.67-8.59 (m, 2H), 7.86 (dd, J=14.6, 7.5 Hz, 1H), 7.40 (t, J=8.8 Hz, 1H), 3.20-3.10 (m, 2H), 2.66 (s, 3H), 2.45 (s, 3H), 1.87-1.74 (m, 2H), 0.99 (t, J=7.4 Hz, 3H).

Calculated exact mass: 486.13 for $C_{22}H_{20}F_2N_6O_3S$ (molecular weight: 486.49);

MS(ESI$^+$): m/z: 486.9 [M+H]$^+$.

Example 31: Synthesis of N-(3-(5-(2-cyclopropyl-4-methylpyrimidin-5-yl)-1H-pyrazolo[3,4-b]pyridine-3 carbonyl)-2,6-difluorophenyl)propane-1-sulfonamide

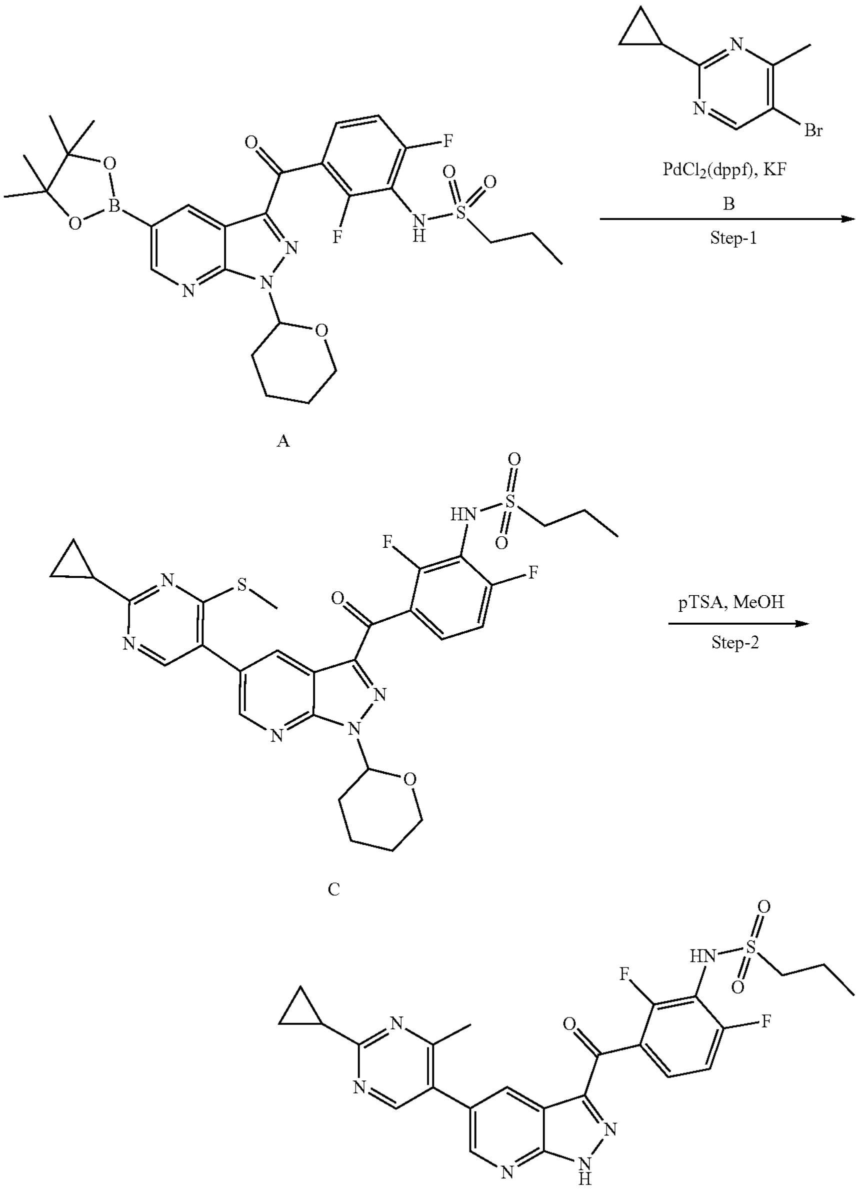

A

C

Step 1: Synthesis of N-(3-(5-(2-cyclopropyl-4-methylpyrimidin-5-yl)-1-(tetrahydro-2H-pyran-2-yl)-1H-pyrazolo[3,4-b]pyridine-3-carbonyl)-2,6-difluorophenyl)propane-1-sulfonamide (C)

N-(2,6-difluoro-3-(1-(tetrahydro-2H-pyran-2-yl)-5-(4,4,5,5-tetramethyl-1,3,2-dioxaborolan-2-yl)-1H-pyrazolo[3,4-b]pyridine-3-carbonyl)phenyl)propane-1-sulfonamide (300 mg, 0.51 mmol), compound B (119 mg, 0.56 mmol) and KF (144 mg, 1.53 mmol) in 1,4-dioxane/$H_2O$ (10 mL) were stirred at room temperature and then purged with argon for 5 min. $PdCl_2(dppf)\cdot CH_2Cl_2$ (42 mg, 0.051 mmol) was added and the mixture was again purged with argon for 5 min. The reaction was then heated to reflux for 8 h. The progress of the reaction was monitored by TLC using (20% EtOAc in Hexane v/v). After completion, the reaction mixture was gradually cooled to room temperature and diluted with ethyl acetate (20 mL), filtered through a pad of celite and concentrated under reduced pressure to afford the crude compound. The crude was finally purified by FCC to give 135 mg (45%) of desired compound C.

$^1H$ NMR (400 MHz, DMSO-$d_6$) δ: 9.69 (s, 1H), 8.81 (d, 1H, J=2.0 Hz), 8.64 (d, 1H, J=2.0 Hz), 8.56 (s, 1H), 7.93-7.85 (m, 1H), 7.43 (t, 1H, J=8.8 Hz), 6.21 (d, 1H, J=9.6 Hz), 3.93-3.97 (m, 1H), 3.71-3.80 (m, 1H), 3.14 (t, 2H, J=7.6 Hz), 2.43 (br s, 3H), 2.21-2.27 (m, 1H), 1.95-2.01 (m, 2H), 1.67-1.75 (m, 3H), 1.55-1.62 (m, 3H), 1.10-1.20 (m, 4H), 0.99 (t, 3H, J=7.2 Hz).

MS(ESI$^+$): m/z 597.1 (M+H$^+$)

Step-2: Synthesis of N-(3-(5-(2-cyclopropyl-4-methylpyrimidin-5-yl)-1H-pyrazolo[3,4-b]pyridine-3-carbonyl)-2,6-difluorophenyl)propane-1-sulfonamide To a solution of compound C (135 mg, 0.22 mmol) in MeOH (10 mL) at room temperature was added p-TSA (28 mg, 0.24 mmol), the reaction mixture was heated to 50° C. for 6 h. Progress of the reaction was monitored by TLC using (5% MeOH in DCM v/v). After, completion of reaction the solvent was evaporated in vacuum, water (5 mL) was added and mixture was neutralized using aq. sat. $NaHCO_3$ and extracted with EtOAc (3×20 mL). The combined organic layer was dried over anhydrous $Na_2SO_4$ and concentrated under reduced pressure to afford crude compound which on trituration gave 55 mg (48%) of desired compound as an off white solid.

$^1$H NMR (400 MHz, DMSO-$d_6$) δ: 9.67 (br s, 1H), 8.76 (d, 1H, J=2.0 Hz), 8.61 (d, 1H, J=2.0 Hz), 8.55 (s, 1H), 7.82-7.88 (m, 1H), 7.39 (t, 1H, J=8.80 Hz), 3.14 (t, 2H, J=7.60 Hz), 2.42 (s, 3H), 2.20-2.28 (m, 1H), 1.80 (q, 2H, J=7.60 Hz), 1.05-1.11 (m, 4H), 0.99 (t, 3H, J=7.20 Hz).

Calculated exact mass: 512.14 for $C_{24}H_{22}F_2N_6O_3S$ (molecular weight: 512.53);

MS(ESI$^+$): m/z 513.60 [M+H]$^+$.

Example 32: Synthesis of N-(3-(5-(2-cyclopropyl-4-(methylthio)pyrimidin-5-yl)-1H-pyrazolo[3,4-b]pyridine-3 carbonyl)-2,6-difluorophenyl)propane-1-sulfonamide Part A. Synthesis of 5-Bromo-2-cyclopropyl-4-(methylthio)pyrimidine (D)

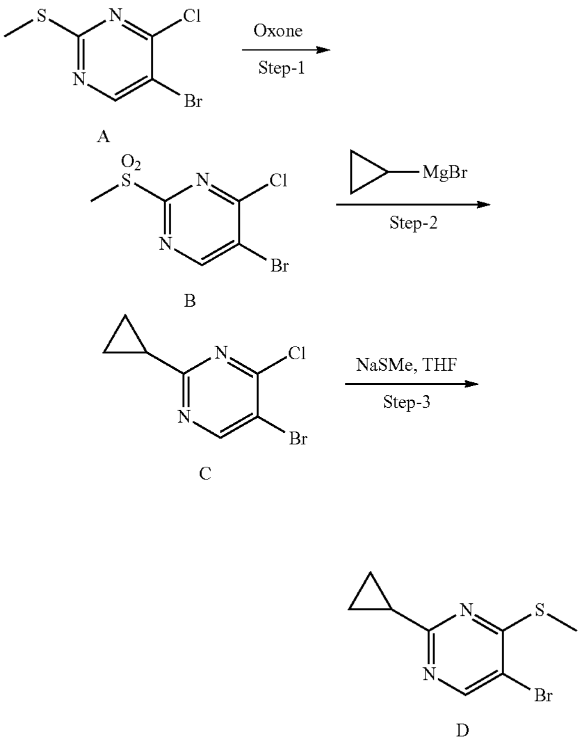

Step-1: 5-bromo-4-chloro-2-(methylsulfonyl)pyrimidine (B)

To a stirred solution of 5-bromo-4-chloro-2-(methylthio) pyrimidine (3 g, 12.6 mol) in THF (25 mL) at room temperature was added oxone (1.16 g, 37.8 mmol) dissolved in water (15 mL). The mixture was then allowed to stir for 4 h. After completion of the reaction as seen by TLC using EtOAc/n-hexane (30/70% v/v) as solvent, the reaction was diluted with water (50 mL) and extracted with EtOAc (3×25 mL). The combined separated organic layers were washed with brine, dried over anhydrous $Na_2SO_4$ and evaporated under reduced pressure to give 3.2 g (94%) of compound B as an off-white solid.

$^1$H NMR (400 MHz, DMSO-$d_6$) δ: 9.38 (s, 1H), 3.41 (s, 3H)

MS(ESI$^+$): m/z 272.80 [M+H]$^+$

Step-2: 5-bromo-4-chloro-2-cyclopropylpyrimidine (C)

To a stirred solution of compound B (1.5 g, 5.55 mmol) in dry THF (20 mL) at 0° C. was slowly added 1M cyclopropylmagnesium bromide (6.66 mL, 6.66 mmol). The mixture was then gradually warmed to RT and stirred for 2 h. After completion of the reaction as seen by TLC using EtOAc/n-hexane (20/80% v/v) as solvent, it was quenched by addition of aq. $NH_4Cl$ solution and extracted using EtOAc (2×25 mL). Separated combined organic layers were washed with brine (15 mL), dried over anhydrous $Na_2SO_4$ and evaporated under reduced pressure to give the crude compound. The crude was finally purified by FCC to give 600 mg (52%) of desired compound C as an off-white solid.

$^1$H NMR (400 MHz, DMSO-$d_6$) δ: 8.59 (s, 1H), 2.05-2.25 (m, 1H), 1.05-1.10 (m, 4H)

MS(ESI$^+$): m/z 234.8 [M+H]$^+$.

Step-3: 5-Bromo-2-cyclopropyl-4-(methylthio)pyrimidine (D)

To a stirred solution of compound C (1.2 g, 5.17 mmol) in DMF (10 mL) at RT was added NaSMe (544 mg, 7.75 mol) and the mixture was stirred for 16 h at RT. After, completion of reaction as seen by TLC using EtOAc/n-hexane (10/90% v/v), water (30 mL) was added and extracted with EtOAc (2×25 mL), the separated organic layer was washed with brine, dried over anhydrous $Na_2SO_4$ and evaporated under reduced pressure to give 800 mg (80%) of compound D as a yellow liquid.

$^1$H NMR (400 MHz, $CDCl_3$) δ: 8.25 (s, 1H), 2.52 (s, 3H), 4.10-4.23 (m, 1H), 1.10-1.20 (m, 4H)

MS(ESI$^+$): m/z 246.8 [M+H]$^+$.

Part B: Synthesis of N-(3-(5-(2-cyclopropyl-4-(methylthio)pyrimidin-5-yl)-1H-pyrazolo[3,4-b] pyridine-3 carbonyl)-2,6-difluorophenyl)propane-1-sulfonamide

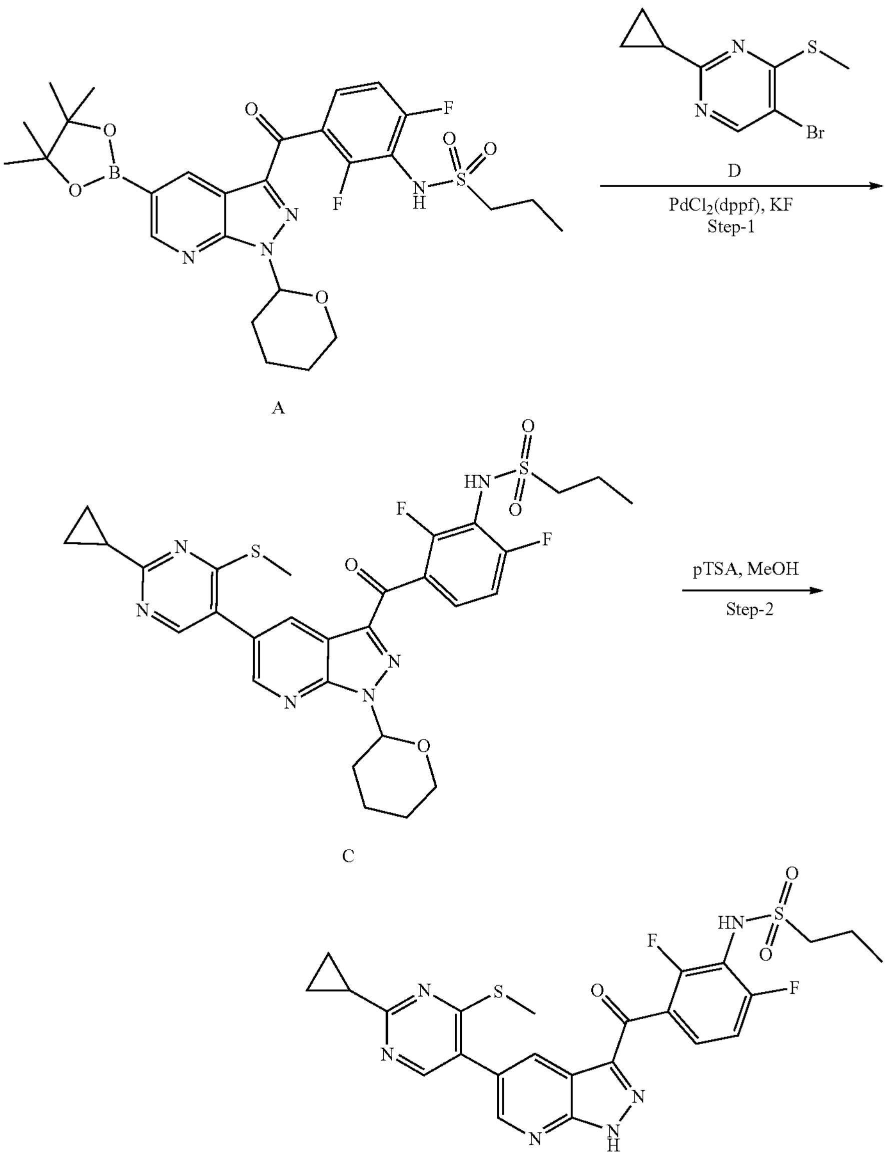

Step-1: N-(3-(5-(2-cyclopropyl-4-(methylthio)pyrimidin-5-yl)-1-(tetrahydro-2H-pyran-2-yl)-1H-pyrazolo[3,4-b]pyridine-3-carbonyl)-2,6-difluorophenyl) propane-1-sulfonamide (C)

To a stirred solution of N-(2,6-difluoro-3-(1-(tetrahydro-2H-pyran-2-yl)-5-(4,4,5,5-tetramethyl-1,3,2-dioxaborolan-2-yl)-1H-pyrazolo[3,4-b]pyridine-3-carbonyl)phenyl)propane-1-sulfon-amide (400 mg, 0.67 mmol) and compound D (182 mg, 0.74 mmol) in 5 ml 1,4-dioxane/$H_2O$ (75/25% v/v) was added 118 mg (2.03 mmol) KF, dissolved in 1 mL water. The resulting mixture was purged with argon for 5 min, then Pd(dppf)$Cl_2$ DCM (0.1 eq., 55 mg, 0.067 mmol) was added and the mixture was again purged with argon for 5 min. The reaction was then heated at 90° C. for 6 h. After completion of reaction, water (10 mL) was added and pH was adjusted to 6 with 1N HCl. The mixture was extracted with EtOAc (3×15 mL), the organic layer was separated, dried and concentrated to give the crude residue. The crude material was purified by reverse phase preparative HPLC to give 60 mg (14% yield) of compound C.

MS(ESI$^+$): m/z 629.20 $[M+H]^+$.

Step 2: N-(3-(5-(2-Cyclopropyl-4-(methylthio)pyrimidin-5-yl)-1H pyrazolo[3,4-b]pyridine-3 carbonyl)-2,6-difluorophenyl) propane-1-sulfonamide To a stirred solution of compound C (90 mg, 0.143 mmol) in MeOH (2 mL) was added pTSA (74 mg, 0.42 mmol) at RT and the reaction mixture was heated to 65° C. for 16 h.

Progress of reaction was monitored by TLC using EtOAc/n-hexane (70/30% v/v). After, completion of reaction the solvent was evaporated in vacuum, water (5 mL) was added, then neutralized (pH=7) with aq. $NaHCO_3$ solution and extracted with EtOAc (3×5 mL). The separated organic layer was dried over anhydrous $Na_2SO_4$ and concentrated under reduced pressure to afford the crude product which was purified by SFC to give 25 mg (32%) of desired compound.

$^1$H NMR (400 MHz, DMSO-$d_6$) δ: 9.66 (s, 1H), 8.72 (s, 1H), 8.69 (s, 1H), 8.37 (s, 1H), 7.86 (q, 1H, J=6.8 Hz), 7.39 (t, 1H, J=8.8 Hz), 3.14 (t, 2H, J=8.0 Hz), 2.20-2.30 (m, 1H), 1.70-1.86 (m, 2H), 1.10-1.15 (br s, 4H), 0.99 (t, 3H, J=7.2 Hz).

Calculated exact mass: 512.14 for $C_{24}H_{22}F_2N_6O_3S$ (molecular weight: 512.53);

MS(ESI$^+$): m/z 545.10 [M+H]$^+$.

Example 33: Synthesis of N-[2,6-difluoro-3-[5-(4-methyl-2-methylsulfanyl-pyrimidin-5-yl)-1H-pyrazolo[3,4-b]pyridine-3-carbonyl]phenyl]propane-1-sulfonamide Example 33 was synthesized in analogy to Example 7.

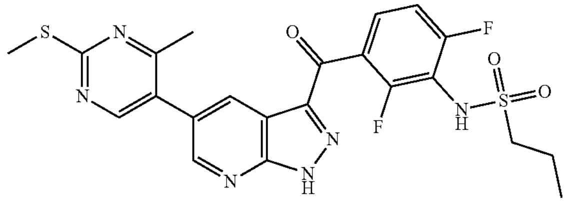 [SMILES: CCCS(=O)(=O)Nc1c(F)ccc(C(=O)c2n[nH]c3ncc(-c4cnc(SC)nc4C)cc23)c1F]

Analytical Data:

$^1$H NMR (400 MHz, DMSO-$d_6$) δ 14.79 (s, 1H), 9.73 (s, 1H), 8.77 (d, J=2.0 Hz, 1H), 8.65 (d, J=2.0 Hz, 1H), 8.58 (s, 1H), 7.86 (dd, J=14.6, 7.8 Hz, 1H), 7.39 (t, J=9.0 Hz, 1H), 3.21-3.05 (m, 2H), 2.57 (s, 3H), 2.44 (s, 3H), 1.91-1.68 (m, 2H), 0.99 (t, J=7.4 Hz, 3H).

Calculated exact mass: 518.10 for $C_{22}H_{20}F_2N_6O_3S_2$ (molecular weight: 518.56);

MS(ESI$^+$): m/z: 517.5 [M−1]$^+$.

Example 34: Synthesis of N-[3-[5-(2,4-dimethoxypyrimidin-5-yl)-1H-pyrazolo[3,4-b]pyridine-3-carbonyl]-2,6-difluoro-phenyl]propane-1-sulfonamide Example 34 was synthesized in analogy to Example 7.

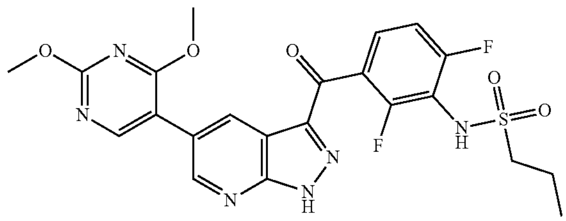 [SMILES: CCCS(=O)(=O)Nc1c(F)ccc(C(=O)c2n[nH]c3ncc(-c4cnc(OC)nc4OC)cc23)c1F]

Analytical Data:

$^1$H NMR (400 MHz, DMSO-$d_6$) δ 14.80 (s, 1H), 9.66 (s, 1H), 8.81 (d, J=2.1 Hz, 1H), 8.69 (d, J=2.1 Hz, 1H), 8.54 (s, 1H), 7.84 (dd, J=14.5, 7.7 Hz, 1H), 7.38 (t, J=8.8 Hz, 1H), 4.05-3.89 (m, 6H), 3.18-3.09 (m, 2H), 1.86-1.72 (m, 2H), 0.98 (t, J=7.4 Hz, 3H).

Calculated exact mass: 518.12 for $C_{22}H_{20}F_2N_6O_5S$ (molecular weight: 518.49);

MS(ESI$^+$): m/z 519.15 [M+H]$^+$

Example 35: Synthesis of N-(3-(5-(2-cyclopropylpyrimidin-5-yl)-1H-pyrazolo[3,4-b]pyridine-3-carbonyl)-2,4,6-trifluorophenyl)propane-1-sulfonamide

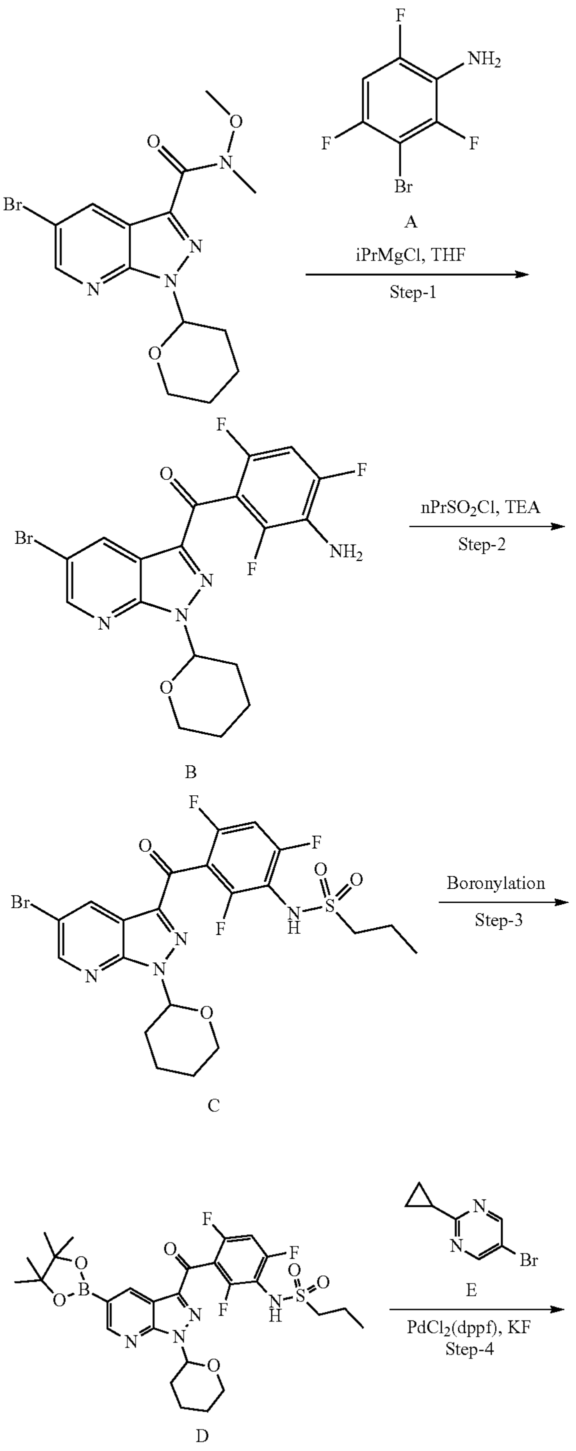

-continued

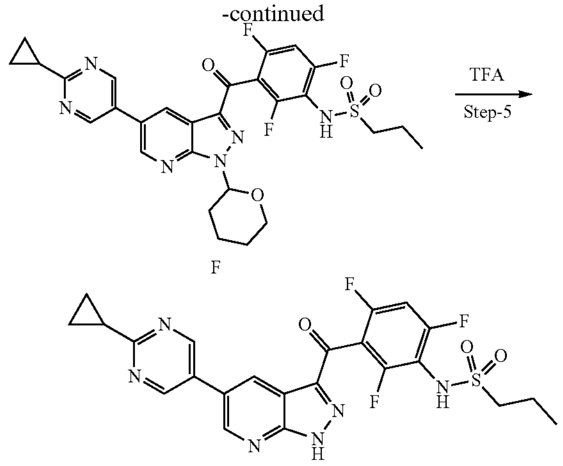

Step-1: Synthesis of (3-amino-2,4,6-trifluorophenyl)(5-bromo-1-(tetrahydro-2H-pyran-2-yl)-1H-pyrazolo[3,4-b]pyridin-3-yl)methanone (B)

Solution A: To compound A (4.22 g, 18.68 mmol) in dry THF (24 mL) was added 2M isopropylmagnesium chloride in THF (9.33 mL, 1 eq., 18.68 mmol) drop wise at −10° C., keeping the temperature below 10° C. After stirring for 20 minutes at 25° C. the reaction was cooled 0° C. and chlorotrimethylsilane (2.02 g, 1 eq., 18.68 mmol) was slowly added. The mixture was warmed to 25° C. and stirred for 30 minutes. The solution was again cooled to −10° C. and 2M isopropylmagnesium chloride in THF (9.33 mL, 1 eq., 18.68 mmol) was added drop wise, keeping the temperature below 10° C. After stirring for 20 minutes at 25° C., the reaction was cooled to 0° C. and chlorotrimethylsilane (2.02 g, 1 eq., 18.68 mmol) was added slowly. The mixture was warmed to 25° C. and stirred for 30 minutes. The reaction was cooled to −10° C. and 2M isopropylmagnesium chloride in THF (9.33 mL, 1 eq., 18.68 mmol) was added drop wise. After complete addition, the mixture was stirred at 0° C. for 20 minutes.

Solution B: In a second flask, 2M isopropylmagnesium chloride in THF (9.33 mL, 1 eq., 18.68 mmol) was added to a suspension of 5-bromo-N-methoxy-N-methyl-1-(tetrahydro-2H-pyran-2-yl)-1H-pyrazolo[3,4-b]pyridine-3-carboxamide (3 g, 8.12 mmol) in THF (30 mL) at −10° C. drop wise, keeping the temperature below 0° C. After complete addition, the mixture was stirred at 0° C. for 10 minutes.

Solution B was added to solution A and the reaction was stirred at 25° C. for 2 h. Then aq. 4N HCl was carefully added until all magnesium salts were dissolved. The aqueous solution was adjusted to pH 5 with 30% $NaOH_{aq}$, saturated with NaCl and the layers were separated. The aqueous layer was extracted with a mixture of THF and EtOAc (addition of EtOAc was necessary to separate the layers). The extract was evaporated, re-dissolved in THF and combined with the organic phase. Conc. $HCl_{aq}$ (5 mL) was added, and the mixture was stirred for 10 min. at RT. The mixture was neutralized with solid $NaHCO_3$, the lower aq. layer was discarded, and the organic layer was dried over $Na_2SO_4$. After evaporation of the solvent, the residue was suspended in diethyl ether (15 mL), triturated with DCM (20 mL) and the solids were collected by suction filtration. The filtrate was evaporated, the residue was taken up in (20 mL) diethyl ether and the solids were collected by suction filtration. The combined solids were purified by FCC using 0-5% MeOH in DCM to give 900 mg (38%) of desired as off-white solid.

$^1$H NMR (400 MHz, DMSO-$d_6$) δ: 8.86 (d, 1H, J=2.0 Hz), 8.80 (d, 1H, J=2.0 Hz), 7.25-7.35 (m, 1H), 6.14 (d, 1H, J=10 Hz), 5.36 (br s, 2H), 3.90-3.95 (m, 1H), 3.70-3.85 (m, 1H), 2.25-2.33 (m, 1H), 1.65-1.85 (m, 1H), 1.50-1.62 (m, 2H), 1.10-1.15 (m, 2H).

MS(ESI$^+$): m/z 455.18 [M+H]$^+$

Step 2: Synthesis of N-(3-(5-bromo-1-(tetrahydro-2H-pyran-2-yl)-1H-pyrazolo[3,4-b]pyridine-3-carbonyl)-2,4,6-trifluorophenyl)propane-1-sulfonamide (C)

To a solution of compound B (900 mg, 1.98 mmol) and triethylamine (13.7 mL, 10 mmol) in THF (20 mL) was added 1-propanesulfonyl chloride (0.8 mL, 7 mmol) in an equal volume of THF slowly at −10° C. and the reaction was stirred at −10° C. for 30 minutes. 2N NaOH (3.75 mL, 12 mmol) was added and THF was evaporated at 45° C. under reduced pressure. The aqueous solution was washed with EtOAc (2×20 mL) and diethyl ether. Residual organics were evaporated, the solution acidified with 2N HCl and vigorously stirred for 30 minutes to break larger lumps. The solid was collected by suction filtration, washed with water and dried at 100° C. to yield compound C as off-white solid (960 mg, 87% yield). $^1$H NMR revealed a mixture of mono and di sulphonamide which was used as such in the next step.

Step-3: Synthesis of N-(2,4,6-trifluoro-3-(1-(tetrahydro-2H-pyran-2-yl)-5-(4,4,5,5-tetramethyl-1,3,2-dioxaborolan-2-yl)-1H-pyrazolo[3,4-b]pyridine-3-carbonyl)phenyl)propane-1-sulfonamide (D)

To a stirred solution of compound C (900 mg, 1.60 mmol) in 1,4-dioxane (15 mL), bis(pinacolato)diboron (612 mg, 2.41 mmol) and KF (278 mg, 4.8 mmol) was added and the resulting mixture was degassed with argon for 10 min. Pd(dppf)$Cl_2$ DCM (65 mg, 0.08 mmol) was added, the mixture was further degassed with argon for 5 min and stirred at 85° C. for 8 h. The progress of the reaction was monitored by TLC using EtOAc/n-hexane (60/40% v/v) as solvent. After completion, the reaction mixture was cooled to RT, diluted with EtOAc (20 mL), filtered through a pad of celite and the organic layer was concentrated under reduced pressure to afford the crude compound, which was purified by FCC to give (960 mg, 87%) of compound D.

MS(ESI$^+$): m/z 609.0 [M+H]$^+$.

Step-4: Synthesis of N-(3-(5-(2-cyclopropylpyrimidin-5-yl)-1-(tetrahydro-2H-pyran-2-yl)-1H-pyrazolo[3,4-b]pyridine-3-carbonyl)-2,4,6-trifluorophenyl)propane-1-sulfonamide (F)

To a stirred solution of compound D (950 mg, 1.56 mmol) and compound E (342 mg, 1.71 mmol) in 1,4-dioxane/$H_2O$ (10 mL), KF (271 mg, 4.68 mmol) was added and the resulting mixture was degassed with argon for 10 min. Pd (dppf)$Cl_2$ DCM (64 mg, 0.078 mmol) was added, the reaction mixture was further degassed with argon for 5 min and stirred at 90° C. for 8 h. The progress of the reaction was monitored by TLC using EtOAc/n-hexane (40/60% v/v) as solvent. After completion, the reaction mixture was cooled to RT and diluted with EtOAc (20 mL), filtered through a pad of celite and the organic layer was concentrated under reduced pressure to afford the crude compound, which on trituration using diethyl ether gave (650 mg, 61%) of compound F.

$^1$H NMR (400 MHz, DMSO-$d_6$) δ: 9.10-9.15 (m, 3H), 8.89 (d, 1H, J=2.4 Hz), 7.80 (t, 1H, J=8.8 Hz), 6.66 (dd, 1H, J=2.4 & 10.4 Hz), 3.60-3.80 (m, 4H), 2.22-2.38 (m, 3H), 1.95-2.00 (m, 2H), 1.72-1.93 (m, 3H), 1.55-1.60 (m, 2H), 1.06-1.09 (m, 2H), 0.95-1.05 (m, 5H)

Step-5: Synthesis of N-(3-(5-(2-cyclopropylpyrimidin-5-yl)-1H-pyrazolo[3,4-b]pyridine-3-carbonyl)-2,4,6-trifluorophenyl)propane-1-sulfonamide To compound F (650 mg, 1.08 mmol) was added TFA (10 mL) at RT and the mixture was stirred overnight. After completion of the reaction as seen by TLC using (MeOH/DCM 5/95% v/v), the reaction mixture was evaporated using a stream of $N_2$ at RT to give the crude compound. This crude material was neutralized to pH 8 using aq. sat. $NaHCO_3$, followed by extraction with DCM (2×20 mL), the organic layer was separated and dried over anhydrous $Na_2SO_4$, evaporation of the solvent gave the crude material. The crude was finally purified by FCC using 0-5% MeOH in DCM (v/v) to give 175 mg (32%) of the desired compound as an off-white solid.

$^1$H NMR (400 MHz, DMSO-$d_6$): 13.05 (br s, 1H), 9.66 (br s, 1H), 9.11 (s, 2H), 9.07 (s, 1H), 8.88 (s, 1H), 7.59 (t, 1H, J=8.0 Hz), 3.13 (t, 1H, J=8.0 Hz), 2.25-3.35 (m, 1H), 1.70-1.85 (m, 2H), 1.05-1.15 (m, 4H), 0.98 (t, 3H, J=7.60 Hz)

MS(ESI$^+$): m/z 517.06 [M+H]$^+$.

Example 36: Synthesis of N-[3-[5-(3-ethyl-4-pyridyl)-1H-pyrazolo[3,4-b]pyridine-3-carbonyl]-2,6-difluoro-phenyl]propane-1-sulfonamide Example 36 was synthesized in analogy to Example 7.

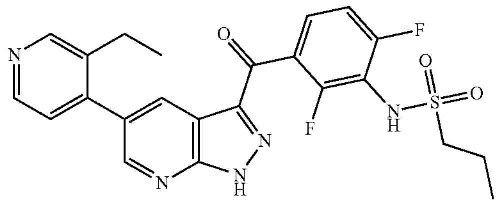 [SMILES: CCCS(=O)(=O)Nc1c(F)ccc(C(=O)c2n[nH]c3ncc(-c4ccncc4CC)cc23)c1F]

Analytical Data:

$^1$H NMR (400 MHz, DMSO-$d_6$) δ 14.90 (s, 1H), 9.67 (s, 1H), 8.72 (d, J=1.9 Hz, 1H), 8.64 (s, 1H), 8.59-8.50 (m, 2H), 7.87 (dd, J=14.7, 7.6 Hz, 1H), 7.39 (dd, J=14.1, 6.6 Hz, 2H), 3.21-3.06 (m, 2H), 2.66 (q, J=7.5 Hz, 2H), 1.88-1.73 (m, 2H), 1.06 (t, J=7.5 Hz, 3H), 1.00 (t, J=7.4 Hz, 3H).

Calculated exact mass: 485.13 for $C_{23}H_{21}F_2N_5O_3S$ (molecular weight: 485.51);

MS(ESI$^-$): m/z: 484.2 [M+H]$^-$.

Example 37: Synthesis of N-[3-[5-(3-cyano-4-pyridyl)-1H-pyrazolo[3,4-b]pyridine-3-carbonyl]-2,6-difluoro-phenyl]propane-1-sulfonamide Example 37 was synthesized in analogy to Example 7.

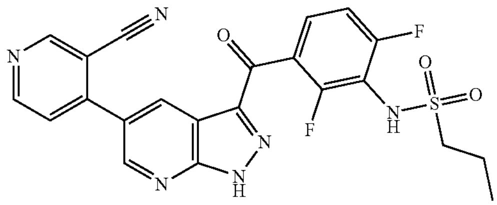

Analytical Data:

$^1$H NMR (400 MHz, DMSO-$d_6$) δ 9.19 (s, 1H), 9.04-8.91 (m, 3H), 7.95-7.84 (m, 2H), 7.41 (t, J=8.8 Hz, 1H), 3.19-3.10 (m, 2H), 1.81 (dq, J=15.0, 7.5 Hz, 2H), 1.00 (t, J=7.4 Hz, 3H).

Calculated exact mass: 482.10 for $C_{22}H_{16}F_2N_6O_3S$ (molecular weight: 482.47);

MS(ESI$^-$): m/z: 481.3 [M+H]$^-$.

Example 38: Biological Activity—Inhibition Potency and Selectivity in Functional Enzyme Assays The kinase activities of the compounds of the invention were measured using the 33PanQinase® Assay Service provided by ProQinase GmbH, Freiburg, Germany. Details of the assay conditions are disclosed on the website of ProQinase (https://www.proqinase.com/products-services-biochemical-assay-services/kinase-assays). In brief, all kinase assays were performed in 96-well FlashPlates™ from PerkinElmer (Boston, MA, USA) in a 50 μl reaction volume. The reaction cocktail was pipetted in four steps in the following order:

20 μl of assay buffer (standard buffer)
5 μl of ATP solution (in $H_2O$)
5 μl of test compound (in 10% DMSO)
20 μl enzyme/substrate mix The assay for all protein kinases contained 70 mM HEPES-NaOH pH7.5, 3 mM $MgCl_2$, 3 mM $MnCl_2$, 3 μM Na-orthovanadate, 1.2 mM DTT, 50 μg/ml PEG20000, ATP (variable concentrations, corresponding to the apparent ATP-Km of the respective kinase), [γ-33P]-ATP (approx. 8x1005 cpm per well), protein kinase and substrate.

The reaction cocktails were incubated at 30° C. for 60 minutes. The reaction is stopped with 50 μl of 2% (v/v) $H_3PO_4$, plates were aspirated and washed two times with 200 μl 0.9% (w/v) NaCl. Incorporation of $^{33}$Pi was determined with a microplate scintillation counter (Microbeta, Wallac).

All assays were performed with a BeckmanCoulter/SAGIAN™ Core System.

In case of single concentration assays, the potency of the test compound is expressed as % residual activity. For determination of IC50-values, serial dilutions in the final concentration range between 100 μM and 3 nM (10 concentrations) were tested. The fitting model for the IC50 determinations was "Sigmoidal response (variable slope)" with parameters "top" fixed at 100% and "bottom" at 0%. The fitting method used was a least-squares fit.

MKK4 Potency:

Inhibition potency against MKK4 is categorized as follows:

Assays with Determination of $IC_{50}$-Values:

| | category |
|---|---|
| $IC_{50}$ < 100 nM: | +++ |
| 100 nM < $IC_{50}$ < 1 μM: | ++ |
| 1 μM < $IC_{50}$ <10 μM: | + |
| $IC_{50}$ > 10 μM: | ○ |

Selectivity of test compounds against BRaf, JNK1 and MKK7, altogether denominated as off-targets was calculated by the ratio of IC50 (off-target)/IC50 (MKK4) and categorized as follows:

| | Category |
|---|---|
| $IC_{50}$(off-target)/$IC_{50}$(MKK4) > 100 | +++ |
| 100 ≥ $IC_{50}$(off-target)/$IC_{50}$(MKK4) > 10 | ++ |
| 10 ≥ $IC_{50}$(off-target)/$IC_{50}$(MKK4) > 3 | + |
| 3 ≥ $IC_{50}$(off-target)/$IC_{50}$(MKK4) | ○ |

TABLE 1

Biochemical potency of representative Examples to MKK4 and selectivity against BRaf, MKK7 and JNK1, based on $IC_{50}$-values.

| | Potency | Selectivity | | |
|---|---|---|---|---|
| Example | MKK4 | Braf | JNK1 | MKK7 |
| 1 | ++ | + | ○ | +++ |
| 2 | +++ | +++ | +++ | +++ |
| 3 | ++ | +++ | ++ | +++ |
| 4 | ++ | +++ | ++ | +++ |
| 5 | + | +++ | + | ++ |
| 6 | ++ | +++ | +++ | +++ |
| 7 | +++ | +++ | +++ | +++ |
| 8 | +++ | +++ | +++ | ++ |
| 9 | ++ | ++ | ++ | ++ |
| 10 | +++ | +++ | +++ | ++ |
| 11 | +++ | +++ | +++ | +++ |
| 12 | ++ | +++ | +++ | +++ |
| 13 | +++ | +++ | ++ | +++ |
| 15 | +++ | +++ | +++ | +++ |
| 16 | +++ | +++ | +++ | +++ |
| 17 | +++ | +++ | +++ | +++ |
| 18 | +++ | +++ | +++ | +++ |
| 19 | ++ | +++ | ++ | +++ |
| 20 | +++ | +++ | ++ | +++ |
| 21 | +++ | +++ | +++ | +++ |
| 22 | +++ | +++ | +++ | +++ |
| 23 | +++ | +++ | +++ | +++ |
| 27 | +++ | +++ | +++ | +++ |
| 28 | +++ | +++ | +++ | ++ |
| 29 | ++ | +++ | +++ | +++ |
| 30 | ++ | +++ | +++ | +++ |
| 31 | ++ | +++ | +++ | +++ |
| 32 | ++ | +++ | +++ | +++ |
| 33 | +++ | +++ | +++ | +++ |
| 34 | +++ | +++ | +++ | +++ |
| 35 | +++ | +++ | +++ | +++ |
| 36 | +++ | +++ | +++ | +++ |
| 37 | +++ | +++ | +++ | +++ |

The invention claimed is:

1. A compound having formula (Ic)

(Ic)

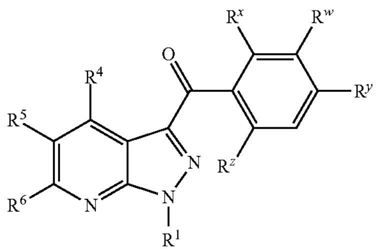

wherein the variables in formula (Ic) have the meanings as follows:

$R^1$ is H or alkyl $R^4$ is H or alkyl;

$R^5$ is selected from a) pyrimidinyl which is substituted with 1 or 2 substituents independently selected from cycloalkyl, alkyl, —$COOR^{10}$, —OH, alkylsulfanyl, tetrazolyl, CN, halogen, and alkoxy, and b) pyridyl which is substituted with 1 or 2 substituents independently selected from alkyl and halogen;

$R^6$ is H or alkyl;

$R^w$ is —$NR^{10}SO_2R^{12}$;

$R^x$ is F;

$R^y$ is F;

$R^z$ is H;

$R^{10}$ at each occurrence is independently H or alkyl;

$R^{12}$ is H, alkyl or phenylalkyl; and n is 1 or 2;

or a pharmaceutically acceptable salt, prodrug, solvate or stereoisomer thereof.

2. The compound or a pharmaceutically acceptable salt, prodrug, solvate or stereoisomer thereof, of claim 1, wherein $R^1$ is H.

3. The compound or a pharmaceutically acceptable salt, prodrug, solvate or stereoisomer thereof, of claim 1, wherein $R^4$ and $R^6$ are H.

4. The compound or a pharmaceutically acceptable salt, prodrug, solvate or stereoisomer thereof, of claim 1, wherein $R^5$ is pyrimidinyl substituted with 1 or 2 substituents independently selected from cycloalkyl, alkyl, alkoxy, —OH, alkylsulfanyl, halogen, CN, and tetrazolyl.

5. The compound or a pharmaceutically acceptable salt, prodrug, solvate or stereoisomer thereof, of claim 4, wherein $R^5$ is pyrimidinyl substituted with 1 or 2 substituents independently selected from cycloalkyl, alkyl, alkoxy, —OH, alkylsulfanyl, halogen, and CN.

6. The compound or a pharmaceutically acceptable salt, prodrug, solvate or stereoisomer thereof, of claim 5, wherein $R^5$ is pyrimidinyl substituted with a group selected from cycloalkyl, alkyl, alkoxy, —OH and alkylsulfanyl and further substituted with a group selected from alkyl, alkoxy, and alkylsulfanyl.

7. The compound or a pharmaceutically acceptable salt, prodrug, solvate or stereoisomer thereof, of claim 1, wherein $R^5$ is pyridyl-4-yl (bonded in 4-position to the pyrazolopyridine group) substituted with alkyl or halogen in 3-position.

8. The compound or a pharmaceutically acceptable salt, prodrug, solvate or stereoisomer thereof, of claim 1, wherein $R^{10}$ is H.

9. The compound or a pharmaceutically acceptable salt, prodrug, solvate or stereoisomer thereof, of claim 1, wherein $R^{12}$ is alkyl or phenylalkyl.

10. The compound or a pharmaceutically acceptable salt, prodrug, solvate or stereoisomer thereof, of claim 9, wherein $R^{12}$ is $C_1$-$C_3$-alkyl or benzyl.

11. The compound or a pharmaceutically acceptable salt, prodrug, solvate or stereoisomer thereof, of claim 1 having formula (Ib)

(Ib)

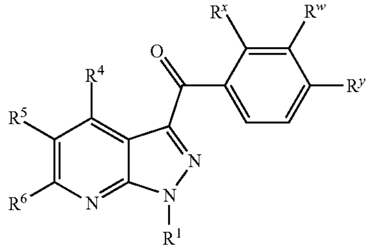

wherein $R^x$ is F;

$R^y$ is F; and $R^1$, $R^4$, $R^5$, $R^6$, and $R^w$ are as defined in claim 1.

12. The compound or a pharmaceutically acceptable salt, prodrug, solvate or stereoisomer thereof, of claim 1 having formula (Ic)

(Ic)

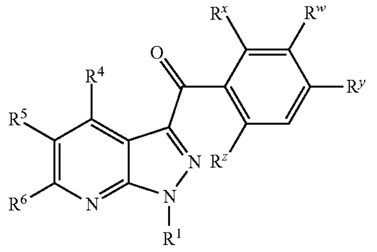

wherein $R^x$ is F;

$R^y$ is F;

$R^z$ is F; and $R^1$, $R^4$, $R^5$, $R^6$, and $R^w$ are as defined in claim 1.

13. A compound of claim 1, selected from

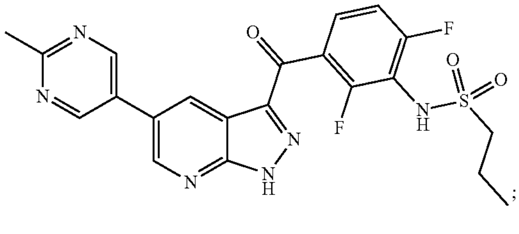
;

-continued

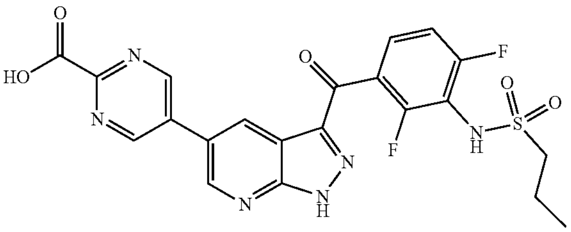

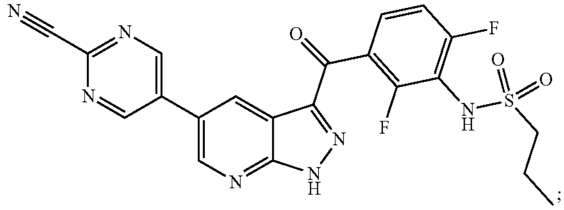
;

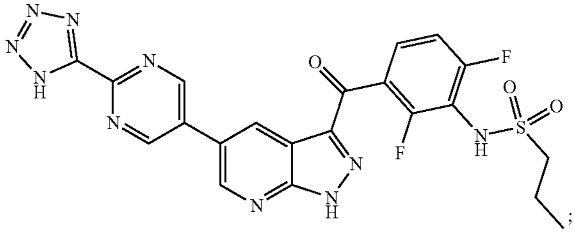
;

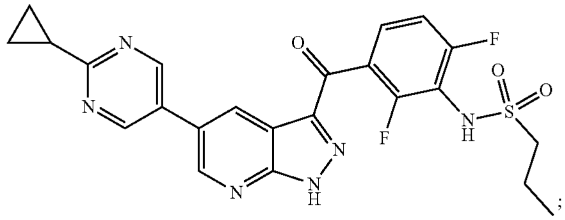
;

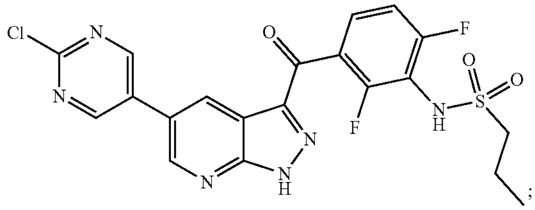
;

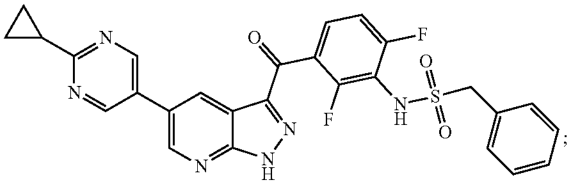
;

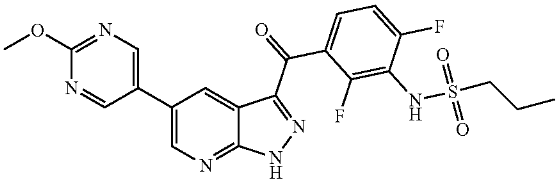
;

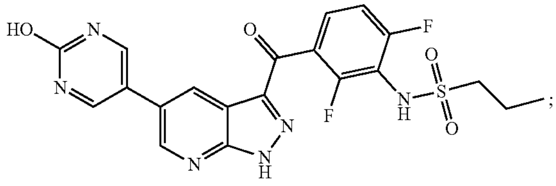
;

-continued
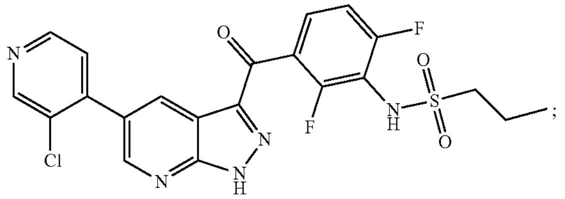
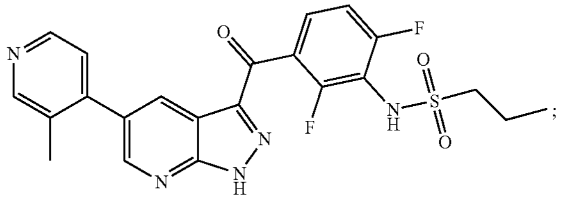
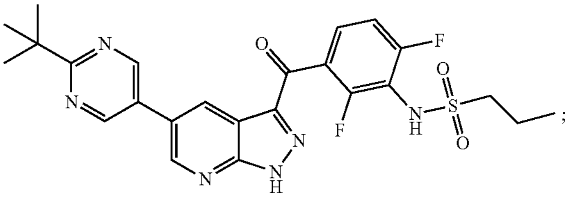
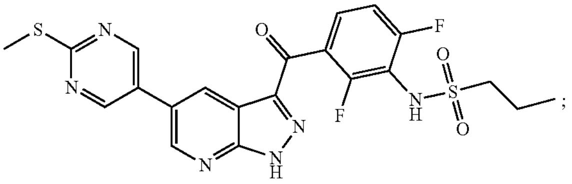
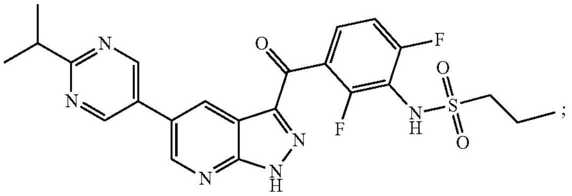
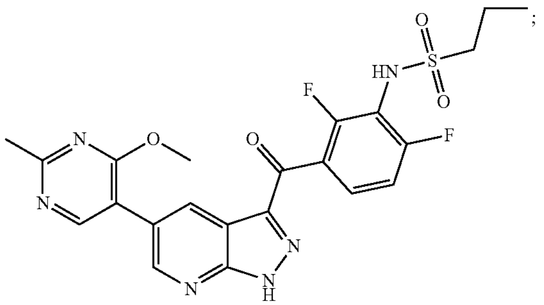
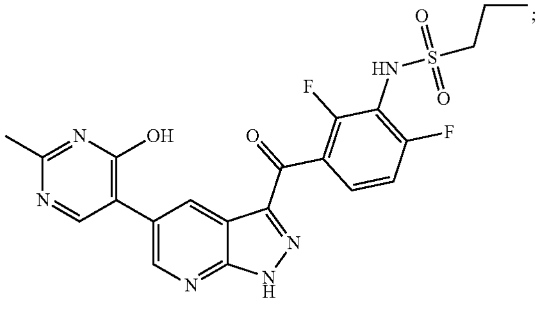
-continued
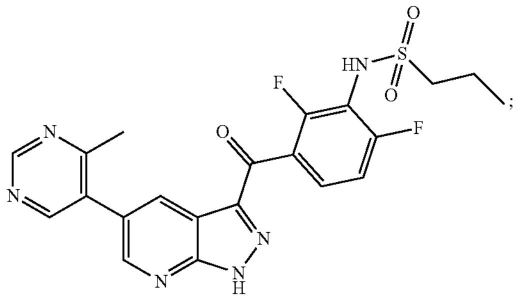
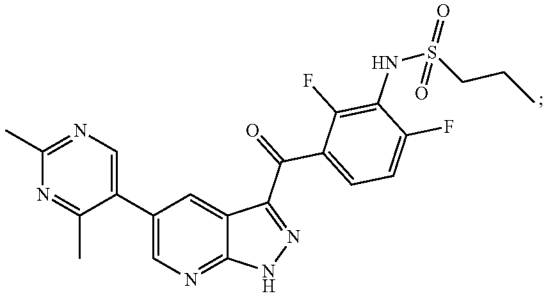
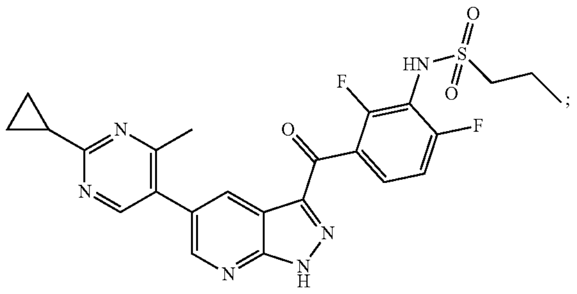
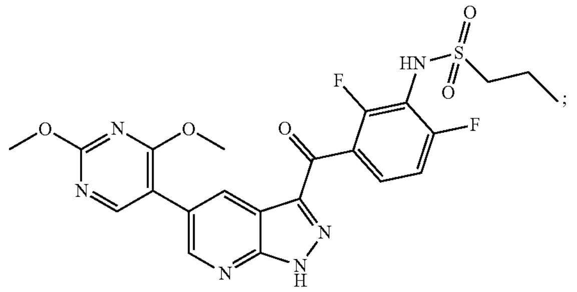
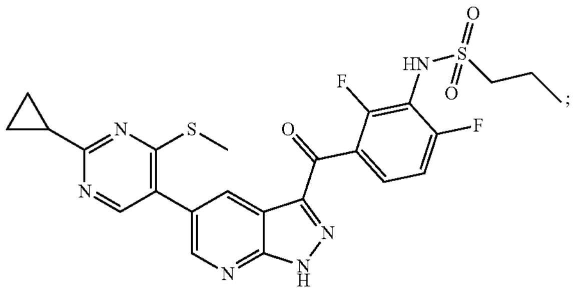

-continued

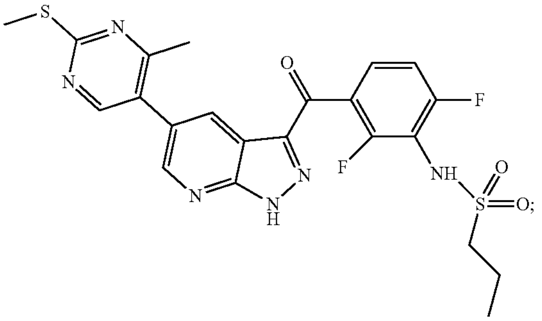

; and

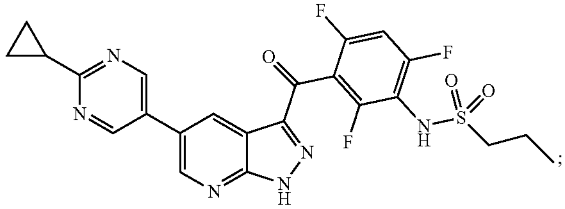

;

or a pharmaceutically acceptable salt, prodrug, solvate or stereoisomer thereof.

14. A compound selected from

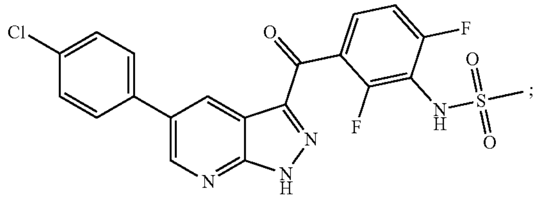

;

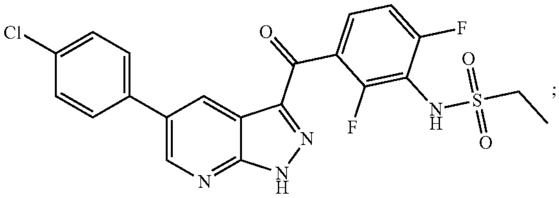

;

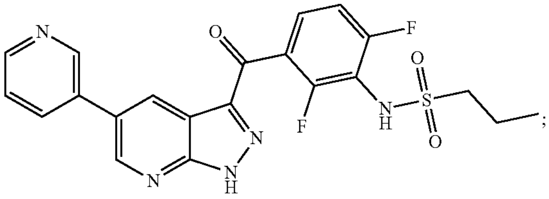

;

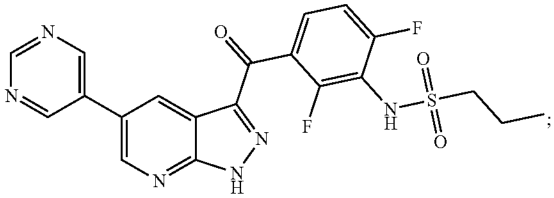

;

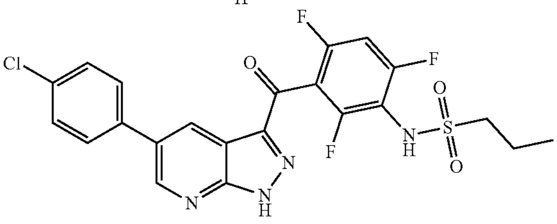

;

-continued

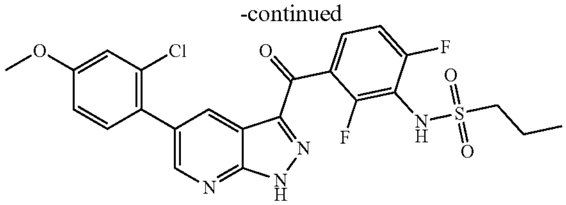

;

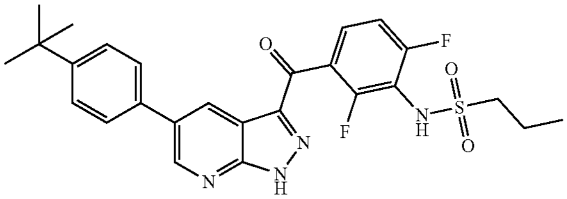

;

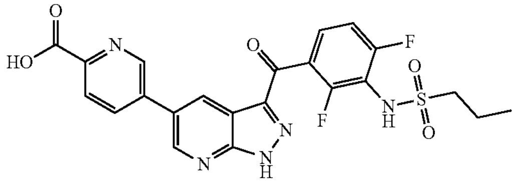

; and

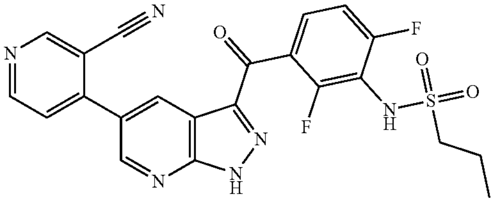 [SMILES: CCCS(=O)(=O)Nc1c(F)ccc(C(=O)c2n[nH]c3ncc(-c4ccncc4C#N)cc23)c1F]

or a pharmaceutically acceptable salt, prodrug, solvate or stereoisomer thereof.

15. A pharmaceutical composition comprising a compound of claim 1 or a pharmaceutically acceptable salt, prodrug, solvate or stereoisomer thereof.

16. A method of selectively inhibiting protein kinase MKK4 over protein kinases JNK1 and MKK7, which comprises administering an effective amount of a compound or a pharmaceutically acceptable salt, prodrug, solvate or stereoisomer thereof as defined in claim 1 to a subject in need thereof.

17. The method of claim 16, wherein the compound or the pharmaceutically acceptable salt, prodrug, solvate or stereoisomer thereof, is administered at a dosage of 0.2 to 15 mg/kg of the subject to be treated over 1 to 12 weeks.

18. A method of promoting liver regeneration or preventing hepatocyte death, which comprises administering an effective amount of a compound or a pharmaceutically acceptable salt, prodrug, solvate or stereoisomer thereof as defined in claim 1 to a subject in need thereof.

19. The method of claim 18, wherein the compound or the pharmaceutically acceptable salt, prodrug, solvate or stereoisomer thereof, is administered at a dosage of 0.2 to 15 mg/kg of the subject to be treated over 1 to 12 weeks.

20. A pharmaceutical composition comprising a compound of claim 14 or a pharmaceutically acceptable salt, prodrug, solvate or stereoisomer thereof.

21. A method of selectively inhibiting protein kinase MKK4 over protein kinases JNK1 and MKK7, which comprises administering an effective amount of a compound or a pharmaceutically acceptable salt, prodrug, solvate or stereoisomer thereof as defined in claim 14 to a subject in need thereof.

22. A method of promoting liver regeneration or preventing hepatocyte death, which comprises administering an effective amount of a compound or a pharmaceutically acceptable salt, prodrug, solvate or stereoisomer thereof as defined in claim 14 to a subject in need thereof.

* * * * *